(12) United States Patent
Angelsen et al.

(10) Patent No.: US 9,939,413 B2
(45) Date of Patent: *Apr. 10, 2018

(54) MEASUREMENT AND IMAGING OF SCATTERERS WITH MEMORY OF SCATTERER PARAMETERS USING AT LEAST TWO-FREQUENCY ELASTIC WAVE PULSE COMPLEXES

(71) Applicant: SURF Technology AS, Trondheim (NO)

(72) Inventors: Bjørn A. J. Angelsen, Trondheim (NO); Rune Hansen, Trondheim (NO); Tonni F. Johansen, Trondheim (NO); Svein-Erik Måsøy, Trondheim (NO); Sven Peter Nasholm, Oslo (NO); Thor Andreas Tangen, Trondheim (NO)

(73) Assignee: SURF Technology AS, Trondheim (NO)

( * ) Notice: Subject to any disclaimer, the term of this patent is extended or adjusted under 35 U.S.C. 154(b) by 269 days.

This patent is subject to a terminal disclaimer.

(21) Appl. No.: 14/044,334

(22) Filed: Oct. 2, 2013

(65) Prior Publication Data
US 2014/0150556 A1 Jun. 5, 2014

Related U.S. Application Data

(63) Continuation-in-part of application No. 12/500,518, filed on Jul. 9, 2009, now Pat. No. 8,550,998, which (Continued)

(51) Int. Cl.
*A61B 8/00* (2006.01)
*G01N 29/34* (2006.01)
(Continued)

(52) U.S. Cl.
CPC .............. *G01N 29/343* (2013.01); *A61B 8/08* (2013.01); *A61B 8/485* (2013.01);
(Continued)

(58) Field of Classification Search
CPC ....... A61B 8/08; A61B 8/485; G01S 7/52095; G01S 7/52077; G01S 7/52022;
(Continued)

(56) References Cited

U.S. PATENT DOCUMENTS 2,004,023 A 6/1935 Uffen
4,215,242 A 7/1980 Gross
(Continued)

FOREIGN PATENT DOCUMENTS

GB 2498519 7/2013

OTHER PUBLICATIONS

Sassaroli et al., "Resonance Frequency of Microbubbles in Small Blood Vessels: A Numerical Study", Institute of Physics Publishing, Phys. Med. Biol. 50, pp. 5293-5305, Nov. 2, 2005.
(Continued)

*Primary Examiner* — Long V Le
*Assistant Examiner* — Colin T Sakamoto
(74) *Attorney, Agent, or Firm* — Cozen O'Connor

(57) ABSTRACT

Measurement or imaging of elastic wave nonlinear scatterers with a memory of scattering parameters comprises selecting LF pulses having characteristics to change the scattering parameters of nonlinear scatterers. A transmit time relation is selected so that the incident HF pulse propagates sufficiently close to the LF pulse that the effect of the incident LF pulse on its scatterer parameters is observed by the HF pulse. At least two elastic wave pulse complexes comprising a high frequency (HF) pulse and a selected low frequency (LF) pulse are transmitted towards the region. Received HF signals are combined to form nonlinear HF signals repre-
(Continued)

senting the scatterers with memory, with suppression of received HF signals from other scatterers. At least one of the received HF signals may be corrected by time delay correction and/or speckle correction with a speckle correction filter, determined by movement of the scattering object. Systems are also disclosed.

26 Claims, 20 Drawing Sheets

Related U.S. Application Data is a continuation-in-part of application No. 12/351,766, filed on Jan. 9, 2009, now abandoned.

(60) Provisional application No. 61/127,898, filed on May 16, 2008, provisional application No. 61/010,486, filed on Jan. 9, 2008.

(51) Int. Cl.
 G01S 7/52 (2006.01)
 A61B 8/08 (2006.01)
 G01S 15/89 (2006.01)

(52) U.S. Cl.
 CPC ...... *G01S 7/52022* (2013.01); *G01S 7/52038* (2013.01); *G01S 7/52077* (2013.01); *G01S 7/52095* (2013.01); *G01S 15/8952* (2013.01); *G01S 7/52049* (2013.01); *G01S 15/8929* (2013.01)

(58) Field of Classification Search
 CPC ............ G01S 7/52038; G01S 7/52049; G01S 15/8952; G01S 15/8929; G01N 29/343
 USPC ............... 600/453–459, 437, 448, 440–447; 73/599, 602, 626; 702/2, 10, 16, 17
 See application file for complete search history.

(56) References Cited

U.S. PATENT DOCUMENTS

| | | | |
|---|---|---|---|
| 4,610,255 A | 9/1986 | Shimura et al. | |
| 5,961,464 A | 10/1999 | Poland | |
| 6,312,383 B1 | 11/2001 | Lizzi et al. | |
| 6,485,423 B2 | 11/2002 | Angelsen et al. | |
| 6,789,018 B1 | 9/2004 | Khan | |
| 6,845,423 B2 | 1/2005 | Park | |
| 6,905,465 B2 | 6/2005 | Angelsen et al. | |
| 7,273,455 B2 | 9/2007 | Angelsen et al. | |
| 7,641,613 B2* | 1/2010 | Angelsen | G01S 7/52022 600/458 |
| 7,727,156 B2 | 6/2010 | Angelsen et al. | |
| 8,038,616 B2* | 10/2011 | Angelsen | A61B 8/14 600/437 |
| 8,550,998 B2* | 10/2013 | Angelsen | A61B 8/08 600/437 |
| 2002/0042572 A1 | 4/2002 | Fukukita | |
| 2003/0114758 A1 | 6/2003 | Jensen et al. | |
| 2004/0006272 A1 | 1/2004 | Vortman et al. | |
| 2004/0236222 A1 | 11/2004 | Mao et al. | |
| 2005/0277835 A1 | 12/2005 | Angelsen et al. | |
| 2006/0052699 A1 | 3/2006 | Angelsen et al. | |
| 2009/0178483 A1 | 7/2009 | Angelsen et al. | |
| 2010/0249590 A1 | 9/2010 | Kanayama et al. | |

OTHER PUBLICATIONS

Angelesen et al., "SURF Imaging—A New Method for Ultrasound Contrast Agent Imaging", Ultrasonics Symposium 2007, IEEE, Oct. 30, 2007, pp. 531-541.
Deng et al., "Study of Ultrasonic Contrast Agents Using a Dual-Frequency Band Technique", World Federation for Ultrasound in Medicine & Biology, vol. 26, No. 5, Jun. 1, 2000, pp. 819-831.
Masoy et al., "SURF Imaging: In Vivo Demonstration of an Ultrasound Contrast Agent Detection Technique", Internet, Sep. 19, 2007, pp. 1-20.
Bouakaz et al., "Radial Modulation of Microbubbles for Ultrasound Contrast Imaging" Ultrasonics, Ferroelectrics & Frequency Control, IEEE vol. 54, No. 11, Nov. 1, 2007, pp. 2283-2290.
Cherin et al., "Radial Modulation Imaging of Microbubbles at High Frequency" Ultrasonics Symposium 2007, IEEE, Oct. 10, 2007, pp. 888-891.
Kaupang et al., "Second-Harmonic Aberration Correction", Ultrasonics Symposium, 2007, IEEE, Conference Oct. 28-31, 2007, Nov. 4, 2007, pp. 1-4.
Masoy et al., "SURF Imaging: In Vivo Demonstration of an Ultrasound Contrast Agent Detection Technique", Ultrasonics, Ferroelectrics and Frequency Control, IEEE vol. 55, No. 5, May 1, 2008, pp. 1112-1121.
Final Office Action dated Mar. 2, 2012 issued in the related U.S. Appl. No. 12/500,518.
Office Action dated Jun. 22, 2011 issued in the related U.S. Appl. No. 12/500,518.
Office Action dated Jan. 15, 2015 issued in the related U.S. Appl. No. 12/351,766.
Final Office Action dated Oct. 5, 2012 issued in the related U.S. Appl. No. 12/351,766.
Office Action dated Apr. 13, 2011 issued in the related U.S. Appl. No. 12/351,766.
Notice of Allowance dated Mar. 12, 2013 issued in the related U.S. Appl. No. 12/500,518.
Search Report and Written Opinion dated Jun. 7, 2009 issued in the corresponding International Patent Application No. PCT/NO2009/000013.
Extended Search Report dated May 21, 2013 issued in the corresponding European Patent Application No. 13 16 2029.

* cited by examiner

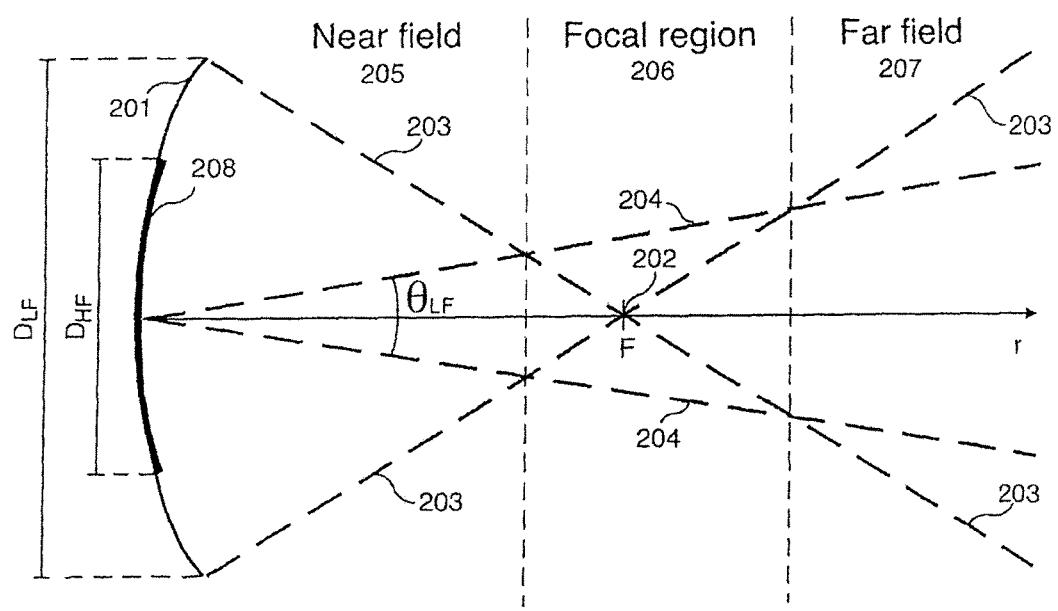
FIG. 2A
FIG. 2A(2) 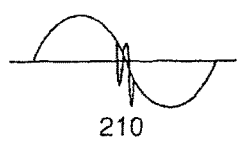 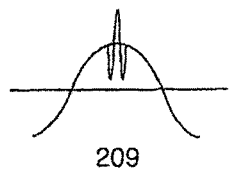 FIG. 2A(1)
FIG. 2A(4) 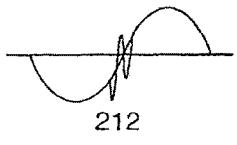 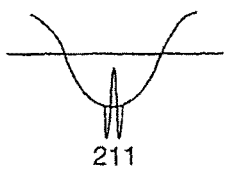 FIG. 2A(3)

MEASUREMENT AND IMAGING OF SCATTERERS WITH MEMORY OF SCATTERER PARAMETERS USING AT LEAST TWO-FREQUENCY ELASTIC WAVE PULSE COMPLEXES

1. CROSS REFERENCES TO RELATED APPLICATIONS

This application is a Continuation-in-Part of U.S. patent application Ser. No. 12/500,518, filed Jul. 9, 2009, which is a Continuation-in-Part of U.S. patent application Ser. No. 12/351,766, filed Jan. 9, 2009, which claims priority from U.S. Provisional Patent Application No. 61/127,898 filed in US on May 16, 2008 and U.S. Provisional Patent Application No. 61/010,486 filed in the US on Jan. 9, 2008. The disclosures of U.S. patent application Ser. No. 12/500,518 and U.S. patent application Ser. No. 12/351,766 are expressly incorporated by reference herein.

2. FIELD OF THE INVENTION

The present invention is directed to methods and instrumentation that utilizes nonlinear elasticity for measurements and imaging with elastic waves in materials, as for example, but not limited to medical ultrasound imaging, ultrasound nondestructive testing, sub sea SONAR applications, and geological applications.

3. BACKGROUND OF THE INVENTION

Nonlinear elasticity means that the material elastic stiffness changes with elastic deformation of the material. For example does the material volume compression stiffness increase with volume compression of the material with a subsequent increase in the volume compression wave propagation velocity. Similarly does volume expansion reduce the material volume compression stiffness with a subsequent reduction in volume compression wave propagation velocity.

In solids one also have a shear deformation elasticity which makes shear deformation waves possible in the solids. Gases and fluids are fully shape deformable, and hence do not have shear elasticity and shear waves. Soft biological tissues behave for pressure waves mainly as a fluid (water), but the solid constituents (cells) introduce a shear deformation elasticity with low shear modulus. The propagation velocity of pressure compression waves are for example ~1500 m/sec in soft tissues, while shear waves have propagation velocities ~1-10 m/sec only. Compared to volume compression, shear deformation of solid materials has a more complex nonlinear elasticity, where in general for isotropic materials any shear deformation increases the shear modulus with a subsequent increase in shear wave velocity. The shear modulus is also in general influenced by volume compression, where as for the bulk modulus a volume compression increases the shear modulus with a subsequent increase in shear wave velocity while volume expansion decreases the shear modulus with a subsequent decrease in shear wave velocity. For anisotropic materials the dependency of the shear modulus with shear deformation can be more complex, where shear deformation in certain directions can give a decrease in shear elastic modulus with a decrease in shear wave velocity.

As different materials have different nonlinear elasticity, compression/expansion/deformation of a spatially heterogeneous material will change the spatial variation of the elasticity and hence produce a scattering that depends on the material strain. The scattered signal can hence be separated into a linear scattering component produced by the heterogeneous elasticity at low strain, and a nonlinear scattering component of elastic waves from the modification of the heterogeneous elasticity produced by large strain in the material. Nonlinear elasticity hence influences both propagation and scattering of pressure waves in gases, fluids and solids, and also of shear waves in solids. The nonlinear volume elasticity effect is generally strongest with gases, intermediate with fluids, and weakest with solid materials.

Acoustic noise produced by multiple scattering and wave front aberrations, reduces the image quality and produces problems for extraction of the nonlinearly scattered signal and propagation and scattering parameters. Current ultrasound image reconstruction techniques take as an assumption that the wave propagation velocity do not have spatial variations, and that the ultrasound pulse is scattered only once from each scatterer within the beam ($1^{st}$ order scattering). In most situations, especially in difficult to image patients, the $1^{st}$ order scattered pulse will be rescattered by a $2^{nd}$ scatterer ($2^{nd}$ order scattered wave), which is rescattered by a $3^{rd}$ scatterer ($3^{rd}$ order scattered wave) etc. With backscatter measurements and imaging, odd orders of scattered waves will have an added propagation delay and show as acoustic noise in the image.

In U.S. patent application Ser. No. 11/189,350 (US Pat Pub 2005/0277835) and U.S. Pat. No. 8,036,616, methods are described where one transmits at least two elastic wave pulse complexes composed of a pulse in a high frequency (HF) band and a pulse in a low frequency (LF) band, both for suppression of acoustic pulse reverberation noise (multiple scattering noise) and for estimation of elastic wave nonlinear propagation properties and elastic wave nonlinear scattering in heterogeneous materials. The LF pulse is used to nonlinearly manipulate the material elasticity that is observed by the HF pulse along its propagation path, and hence nonlinearly manipulate the propagation velocity and/or the scattering for the HF pulse. The applications exemplify the method for ultrasound imaging of soft tissues, but it is clear that the method is applicable to all types of elastic wave imaging, as for example but not limited to, nondestructive testing of materials, sub sea SONAR applications, geological applications, etc. The methods are applicable with compression waves in gases, fluids, and solids, and also with shear waves in solids. Shear waves can for example be transmitted with special transducers, be generated by the radiation force from compression waves, or by skewed inclination of pressure waves at material interfaces. Similarly can pressure waves be generated both directly with transducers and with skewed inclination of shear waves at material interfaces.

When the LF pulse pressure varies along the HF pulse, the different parts of the HF pulse gets different propagation velocities that introduces a change of the pulse length and possibly also a distortion of the pulse form of the HF pulse that accumulates along the propagation path. Such a variation of the LF pulse pressure can be found when the HF pulse is located on a spatial gradient of the LF pulse, but also when a comparatively long HF pulse is found around the pressure maxima and minima of the LF pulse. We will in the following refer to these modifications of the HF pulse length and form by the LF pulse as HF pulse distortion.

With an LF aperture that is so wide that the whole HF imaging range is within the near field of the LF beam, one can obtain a close to defined phase relation between the HF and LF pulse on the beam axis, where the HF pulse can be close to the crest or through of the LF pulse for the whole imaging range. With diffraction limited, focused LF beams, the pressure in the focal zone is the time derivative of the pressure at the transducer surface. The phase relation between HF pulse and the LF pulse will hence in this case slide with depth. For the HF pulse to be at the crest (or trough) of the LF pulse in the LF focal region, the pulse must be transmitted at the negative (positive) spatial gradient of the LF pulse at the transducer. This produces an accumulative length compression of the HF pulse when it is located along a negative spatial gradient of the LF pulse, and an accumulative length stretching of the HF pulse when it is found along a positive spatial gradient of the LF pulse. In order to obtain adequately collimated LF beams, it is often advantageous to use a LF transmit aperture that is wider than the HF transmit aperture, and/or the LF transmit focus is different from the HF transmit focus. This gives an additional phase sliding with the propagation distance of the HF pulse relative to the LF pulse. To suppress multiple scattering noise, one often use a LF transmit aperture with an inactive region around its center. This gives increased phase sliding between the HF and LF pulses.

When the phase between the HF and LF pulses slides with propagation distance, the LF pulse can provide different modifications to the HF pulse at different depths. For example can the HF pulse be at the negative spatial gradient of the LF pulse at low depths and slide via an extremum with negligible spatial gradient of the LF pulse towards a positive spatial gradient of the LF pulse along the HF pulse at deep ranges. The HF pulse in this example observes accumulative pulse compression at shallow depths, via an intermediate region with limited pulse distortion, towards an accumulative pulse length expansion at deep ranges, where the deep range pulse length expansion counteracts the shallow range pulse length compression. Switching the polarity of the LF pulse changes the pulse compression to pulse expansion and vice versa. As the pulse distortion changes the frequency content of the HF pulse, the frequency varying diffraction and power absorption will also change the HF pulse amplitude with the distortion, and we include these phenomena in the concept of HF pulse distortion.

The HF pulse distortion will hence be different for different amplitudes, phases and polarities of the LF pulse, a phenomenon that limits the suppression of the linearly scattered signal to obtain the nonlinearly scattered signal with pure delay correction, for example as described in U.S. patent application Ser. No. 11/189,350 (US Pat Pub 2005/0277835) and (U.S. Pat. No. 8,036,616). The current invention presents methods that improve the suppression of the linear scattering for improved estimation of the nonlinear scattering, and also introduces improved methods of suppression of pulse reverberation noise.

4. SUMMARY OF THE INVENTION

This summary gives a brief overview of components of the invention and does not present any limitations as to the extent of the invention, where the invention is solely defined by the claims appended hereto. The methods are applicable both for backscatter and transmission tomographic image reconstruction methods. For aberration corrections, the methods can apply to individual element or sub-aperture signals as well as to the beam formed received signals.

At least two elastic wave pulse complexes composed of a pulse in a low frequency (LF) band and a pulse in a high frequency (HF) band, are transmitted into the object, where at least the transmitted LF pulses varies for the transmitted pulse complexes, for example in phase (relative to the transmitted HF pulse), and/or amplitude, and/or frequency. The LF transmit aperture and focus can also vary between pulses. The LF pulses are used to nonlinearly manipulate the material elasticity observed by the HF pulses along at least parts of the propagation path of the HF pulses. By the received HF signal we do in this description mean received signal from the transmitted HF pulses that are one or both of scattered from the object and transmitted through the object, and where signal components from the transmitted LF pulse with potential harmonic components thereof, are removed from the signal, for example through filtering of the received HF signal. Such filtering can be found in the ultrasound transducers themselves or in the receiver channel of an instrument. For adequately stationary objects, one can also suppress received components of the transmitted LF pulse by transmitting a LF pulse with zero HF pulse and subtracting the received HF signal from this LF pulse with zero transmitted HF pulse from the received HF signal with a transmitted LF/HF pulse complex. The received HF signal can contain harmonic components of the HF band produced by propagation and scattering deformation of the HF pulse, and in the processing one can filter the received HF signal so that the fundamental band, or any harmonic band, or any combination thereof, of the HF pulse is used for image reconstruction. The harmonic components of the HF pulse can also be extracted with the well-known pulse inversion (PI) method where the received HF signals from transmitted HF pulses with opposite polarity are added. By the received HF signal we hence mean at least one of the received HF radio frequency (RF) signal at the receiver transducer with any order of harmonic components thereof, and any demodulated form of the HF RF signal that contain the same information as the received HF RF signal, such as an I-Q demodulated version of the HF RF signal, or any shifting of the HF RF signal to another frequency band than that found at the receiver transducer. Such frequency shifting is known to anyone skilled in the art, and it is also known that processing on the RF signal can equivalently be done on any frequency shifted version of the RF signal.

For back-scatter imaging, the received HF signal will be picked up by a focused receive beam, usually dynamically focused, so that we will by large observe only the nonlinear manipulation of the object by the LF pulse for the HF pulse close to the axis of the receive beam. Variations of the LF pulse across the HF wave front can nonlinearly modify the focus of the transmitted HF beam, but this effect is small and can be compensated for by corrections of the received HF signal and/or modifications of the HF transmit focus delays. Diffraction also produces a transversal influence of the HF pulses across the HF wave front, but this effect is small and can also be compensated for in the fast time pulse distortion correction described below.

With tomographic image reconstruction methods the image reconstruction introduces a spatial resolution so that we in each pixel observe the nonlinear manipulation by the LF pulse for the HF pulse along the propagation path through said image pixel. The HF pulses from said at least two transmitted pulse complexes hence observe different propagation velocities and different nonlinear scattering from the object, the differences being produced by the differences in the transmitted LF pulses. The LF pulses often have opposite polarity for the said at least two different pulse complexes, but one also can vary the amplitude and/or phase and/or frequency and/or transmit aperture and/or transmit focus of the LF pulse for each transmitted pulse complex.

The HF pulse can be a simple narrowband pulse, or it can be a more complex pulse with frequencies in the HF band, for example Barker, Golay, or chirp code pulses which allows transmission of higher power with limited pulse amplitude, for example limited by the MI, where improved resolution is obtained with pulse compression in the receive processing, according to known methods.

In accordance with an embodiment of the invention, a method for measurement or imaging of elastic wave nonlinear scatterers with a memory of scattering parameters in a region of a scattering object is disclosed comprising selecting LF pulses having characteristics to change the scattering parameters of at least certain of the nonlinear scatterers with a memory that lasts for at least a time interval after the incident LF pulse has passed the nonlinear scatterer. A transmit time relation between the LF pulses and HF pulses is selected so that at least in the measurement or imaging depth range the incident HF pulse propagates spatially behind the incident LF pulse of the same pulse complex, but sufficiently close to the LF pulse that the HF pulse hits the nonlinear scatterers while the effect of the incident LF pulse on its scatterer parameters is observed by the HF pulse. At least two elastic wave pulse complexes are transmitted towards the region. The at least two pulse complex comprises a high frequency (HF) pulse in an HF band and a selected low frequency (LF) pulse in an LF band. At least the LF pulse varies for at least two transmitted pulse complexes, the LF pulse of a pulse complex can be zero, the LF pulse for at least one pulse complex is nonzero, and in the pulse complexes comprising an HF pulse and a non-zero LF pulse, the transmit time have the selected transmit time relation. Received HF signals are picked up from at least one of scattered and transmitted HF components from the at least two transmitted pulse complexes. The received HF signals from the at least two pulse complexes are combined to form nonlinear measurement HF signals representing the nonlinear scatterers with memory of scattering parameters, with suppression of received HF signals from other scatterers. The nonlinear scatterers may be micro-bubbles and/or micro-calcifications, for example. The nonlinear measurements or imaging signals may be processed to form an image display of said nonlinear scatterers with memory of scattering parameters, with suppression of image components from other scatterers.

The depth range may be divided into depth intervals and the scattering object may be moving. In this case, the method may further comprise correcting at least one of the received HF signals in at least one depth interval by at least one of a) time delay correction with a correction delay determined by movement of the scattering object; and b) speckle correction with a speckle correction filter determined by movement of the scattering object. A group of at least two intermediate HF signals are formed from the at least two transmitted pulse complexes in the at least one depth interval. The at least two intermediate HF signals are combined to suppress linear scattering components from the moving object to form nonlinear measurement HF signals representing the local nonlinear scatterers in the at least one depth interval with memory of scattering parameters. The correction delay and/or the speckle correction filter may be estimated from a combination of the received HF signals from at least two pulse complexes.

The at least two pulse complexes may include LF pulses having at least one common characteristic, such as center frequency, amplitude, polarity, and/or pulse length, for example. The at least two pulse complexes may include a pulse complex having a nonzero LF pulse and a pulse complex having a zero LF pulse. At least three pulse complexes may be transmitted, wherein at least two of the at least three pulse complexes have equal LF pulse and at least one of the at least three pulse complexes have a different pulse.

The nonlinear scatterers may have a resonance frequency and the method may further comprise selecting the center frequency of the LF pulse close enough to the scatterer resonance frequency, so that a variation in scattering parameters with memory are produced by the resonating oscillations of the nonlinear scatterers excited by the LF pulse. A resonance frequency may be not be known, in which case multiple groups of pulse complexes may be transmitted, wherein the center frequency of the LF pulse is the same within each group and varies between each of the groups. If the center frequency of the LF pulse for at least one of the groups is close enough to the nonlinear scatterer resonance frequencies of the nonlinear scatterers, so that a variation in scattering parameters with memory are produced by the resonating oscillations of nonlinear scatterers excited by the LF pulse for the at least one of the groups, then the presence of nonlinear scatterers may be detected from the received HF signals the presence of nonlinear scatterers with resonance frequencies close to the LF pulse center frequency for the at least one group.

In accordance with another embodiment of the invention, an instrument for measurement or imaging of elastic wave nonlinear scatterers with a memory of scattering parameters in a region of a scattering object is disclosed comprising at least one controller configured to: i) select LF pulses having characteristics to change the scattering parameters of the nonlinear scatterers with a memory that lasts for at least a time interval after the incident LF pulse has passed the nonlinear scatterer; and ii) determine transmit time relation between the LF and HF pulses so that at least in the measurement or imaging range the incident HF pulse propagates spatially behind the incident LF pulse and close enough to the incident LF pulse that the HF pulse hits the nonlinear scatterers while the effect of the incident LF pulse on its scatterer parameters is observed by the HF pulse.

The instrument further comprises a transmitter configured to transmit at least two elastic wave pulse complexes towards the region, each of the at least two elastic wave pulse complexes comprising a high frequency (HF) pulse in an HF band and a selected low frequency (LF) pulse in an LF band. At least the LF pulse varies for at least two transmitted pulse complexes, the LF pulse of a pulse complex can be zero, the LF pulse for at least one pulse complex is nonzero, and in the pulse complexes comprising an HF pulse and a nonzero LF pulse, the transmit time relations have the selected transmit time. A receiver is configured to pick received HF signals from at least one of scattered and transmitted HF components from the at least two transmitted pulse complexes. The at least one controller is further configured to combine the received HF signals from the at least two pulse complexes with different LF pulses to form nonlinear measurement or imaging HF signals that represent the local resonant scatterers, with suppression of received HF signals from other scatterers. The system may also be configured to implement the steps of the methods described above.

The instrument may further comprise a display unit to display an image, and the controller may be configured to process the nonlinear measurement signals to form image signals of the nonlinear scatterers with memory of scattering parameters, with suppression of image components from other scatterers.

The instrument may further comprise an HF receiver beam former configured to record the received HF signals from multiple HF receive beams, parallel in time. In this example, the at least one controller has sufficient processing capacity to process the received HF signals from the multiple HF receive beams, so that the image frame rate for 2D and 3D imaging is substantially increased as compared to a rate at which collected HF signals from single HF receive beam directions are received serially in time. The at least one controller may be further configured to select a processing method for best performance of the measurements or imaging under constraints that are preset or set by an operator. The controller may also be further configured to estimate wave front aberration corrections and correct the wave front aberrations.

The processed HF signals are further processed to form image signals such as scattering amplitude images, color images representing Doppler frequencies, object displacement, displacement velocities, displacement strain, displacement strain rate, computer tomographic image reconstruction for transmitted signals at different directions, etc., where many such methods are known in the prior art, and also discussed in U.S. patent application Ser. No. 11/189,350 (US Pat Pub 205/0277835) and U.S. Pat. No. 8,036,616.

The invention further includes instruments that incorporate the methods in practical elastic wave imaging of objects.

5. SUMMARY OF THE DRAWINGS

FIG. 2A shows propagation sliding in the phase between the HF and LF pulses and the effect on pulse form distortion;

FIG. 2A(1) shows an on-axis HF pulse found at the crest of the LF pulse in the focal region;

FIG. 2A(2) shows an HF pulse transmitted at the array surface at the zero crossing with the negative spatial of gradient of the LF pulse;

FIG. 2A(3) shows an on-axis HF pulse found at the trough of the LF pulse in the focal region;

FIG. 2A(4) shows an HF pulse transmitted at the array surface at the zero crossing with a positive spatial gradient of the LF pulse;

6. DETAILED DESCRIPTION OF THE INVENTION

Example embodiments according to the invention will now be described with reference to the drawings.

Figure 1A:
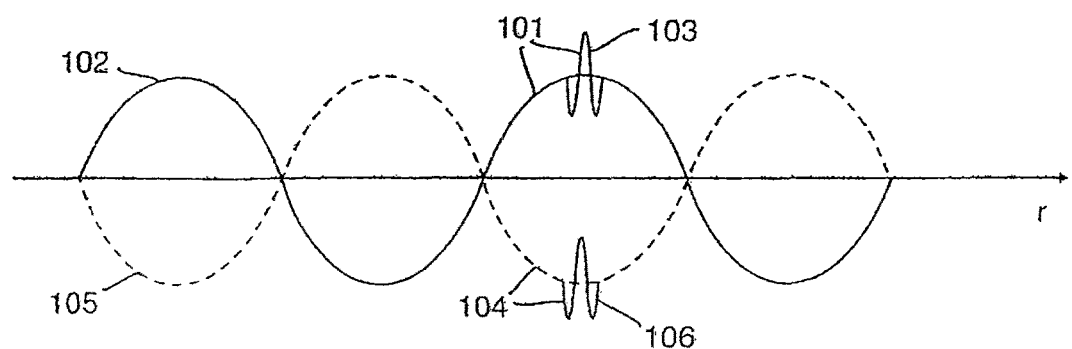
FIGS. 1A-1C show examples of pulse complexes with LF and HF pulses with different phase relationships that occur in the application of the methods.

FIG. 1A shows a $1^{st}$ example transmitted pulse complex 101 composed of a low frequency (LF) pulse 102 and a high frequency (HF) pulse 103, together with a $2^{nd}$ example pulse complex 104 composed of a LF pulse 105 and a HF pulse 106. The LF pulse 102 will compress the material at the location of the HF pulse 103, and nonlinear elasticity will then increase the material stiffness and also the propagation velocity observed by the HF pulse 103 along its propagation path. In the $2^{nd}$ pulse complex 104 the LF pulse 105 expands the material at the location of the HF pulse 106, with a subsequent reduction in material stiffness and reduction in propagation velocity of the HF pulse 106 due to the nonlinear elasticity of the material. The invention makes use of the nonlinear manipulation of the material properties by the LF pulse as observed by a co-propagating HF pulse, and one will generally make use of multiple transmit pulse complexes with variations in the LF pulse between the complexes so that the HF pulses observes different material properties with the variations in the LF pulse. One can also transmit pulse complexes with zero LF pulse. Example variations in the LF pulses can be such as, but not limited to, variations in the LF transmit amplitude, the polarity of the LF pulse, the phase relationship between the HF and LF pulses, variations in the frequency of the LF pulse, and also variations in the LF transmit aperture size and focus, and any combinations of these.

For fluids and solids, the elasticity can generally be approximated to the $2^{nd}$ order in the pressure, i.e. the volume compression $\delta V$ of a small volume $\Delta V$ is related to the pressure p as $$\frac{\delta V}{\Delta V} = K(\underline{r}; p) \approx (1 - \beta_n(\underline{r})\kappa(\underline{r})p)\kappa(\underline{r})p \qquad (1)$$

where $\underline{r}$ is the spatial position vector, $K(\underline{r}:p)$ is the nonlinear elasticity function of the general form and the expression to the right is the approximation to this function to the $2^{nd}$ order in the pressure, which holds in many situations, like in the soft tissue of medical imaging, and also in fluids and polymers. In this expression $\kappa(\underline{r})$ is the linear bulk compressibility of the material, and $\beta_n(\underline{r})=1+B(\underline{r})/2A(\underline{r})$ is a nonlinearity parameter of the bulk compressibility. The material parameters have a spatial variation due to heterogeneity in the material. Gases generally show stronger nonlinear elasticity, where higher order terms in the pressure often must be included. Micro gas-bubbles in fluids with diameter much less than the ultrasound wavelength, also shows a resonant compression response to an oscillating pressure, which is discussed below.

The propagation velocity for the HF pulse will then for a $2^{nd}$ order elastic material be affected by the LF pulse pressure $p_{LF}$ at the locations of the propagating HF pulse, and for approximation of the pressure dependency to the $1^{st}$ order in the pressure, we get $$c(\underline{r},p_{LF})=c_0(\underline{r})\{1+\beta_n(\underline{r})\kappa(\underline{r})p_{LF}\} \quad (2)$$

where $c_0(\underline{r})$ is the unmodified propagation velocity as a function of HF pulse location $\underline{r}$. For a dynamically focused HF receive beam one do with back-scatter imaging observe the object at a narrow region around the beam axis. The propagation lag of the HF pulse along the beam axis can then be approximated as $$t(r) = \int_{\Gamma(r)} \frac{ds}{c(s, p_{LF}(s))} = t_0(r) + \tau(r) \quad (3)$$

$$t_0(r) = \int_{\Gamma(r)} \frac{ds}{c_0(s)}$$

$$\tau(r) = -\int_{\Gamma(r)} \frac{ds}{c_0(s)} \beta_n(s)\kappa(s)p_{LF}(s)$$

$$\tau(t) = -\int_0^t dt_0 \beta_n(s(t_0))\kappa(s(t_0))p_{LF}(s(t_0))$$

where $\Gamma(r)$ is the propagation path of the HF pulse to depth r and the coordinate s denotes the ray location along the HF pulse at any time. The propagation lag without manipulation of the propagation velocity by the LF pulse is $t_0(r)$. For a homogeneous material $t_0(r)=$(propagation length)$/c_0$, where for backscatter imaging at a range r, we have propagation length=2r and $t_0(r)=2r/c_0$. $\tau(r)$ is the added nonlinear propagation delay produced by the nonlinear manipulation of the propagation velocity for the HF pulse by the LF pulse. We note that when a scattering/reflection occurs the LF pulse pressure $p_{LF}$ drops considerably at the location of the scattered HF pulse so that the LF modification of the propagation velocity is negligible for the scattered wave. This means that we only get contribution in the integral for $\tau(r)$ up to the $1^{st}$ scattering, an effect that we will use to suppress multiple scattered waves in the received signal.

We have here given a single coordinate r along the propagation path of the pulse. This is a good approximation with adequately focused beams for the received HF signal, so that one observes a limited cross section along the path of the HF pulse, and can also be obtained for angular scattering and transmission tomographic image reconstruction. The basic idea of the invention do however go beyond such a limited description, but the limited description is used for simplicity to illustrate basic aspects of the invention that also applies to situations where a full 3D description of the pulse propagation is required.

The variation of the propagation velocity with the pressure, will also produce a self distortion of both the LF and HF pulses, that introduces harmonic components of the fundamental bands of the pulses. The different harmonic components have different diffraction, which also influences the net self-distortion from the nonlinear propagation velocity. The LF beam is generally composed of a near-field region where the beam is mainly defined by geometric extension of the LF radiation aperture, and a diffraction limited region, which is the focal region for a focused aperture, and the far-field for an unfocused aperture, as discussed in relation to FIG. 2A below. In the near field region the nonlinear self distortion of the LF pulse is mainly a triangular distortion that do not change the amplitude of the LF pulse at the location of a co-propagating HF pulse. In the diffraction limited region of the LF pulse, the nonlinear self distortion of the positive (102) and negative (105) LF pulses (with same transmit amplitude) will be different so that the elasticity manipulation of the two pulses will be different in this region.

By the received HF signal we do in this description mean the received signal from the transmitted HF pulses that are either scattered from the object or transmitted through the object, and where signal components from the transmitted LF pulse with potential harmonic components thereof, are removed from the signal, for example through filtering of the received HF signal. Such filtering can be found in the ultrasound transducers themselves or in the receiver channel of an instrument. For adequately stationary objects, one can also suppress received components of the transmitted LF pulse by transmitting a LF pulse with zero HF pulse and subtracting the received signal from this LF pulse with zero transmitted HF pulse from the received HF signal with a transmitted LF/HF pulse complex. The received HF signal can contain harmonic components of the HF band produced by propagation and scattering deformation of the HF pulse, and in the processing one can filter the received HF signal so that the fundamental band, or any harmonic band, or any combination thereof, of the HF pulse is used for image reconstruction. The harmonic components of the HF pulse can also be extracted with the well known pulse inversion (PI) method where the received HF signals from transmitted HF pulses with opposite polarity are added. By the received HF signal we hence mean at least one of the received HF radio frequency (RF) signal at the receiver transducer and any order of harmonic components thereof, and any demodulated form of the HF RF signal that contain the same information as the received HF RF signal, such as an I-Q demodulated version of the HF RF signal, or any shifting of the HF RF signal to another frequency band than that found at the receiver transducer. Such frequency shifting is known to anyone skilled in the art, and it is also known that processing on the RF signal can equivalently be done on any frequency shifted version of the RF signal.

Different materials, as for example gas bubbles, micro calcifications, connective tissue, fat, polymers, wax, scales, concrete, geologic structures, metals, etc. have different nonlinear elastic parameters. The incident LF pulse will therefore in a nonlinearly heterogeneous material change the spatial variation of the local elasticity observed by the HF pulse, and hence produce a local scattering of the HF pulse that depends on the LF pressure at the HF pulse. The scattered HF pulse can therefore be separated into a linear component of the scattered signal that is found for zero LF pulse, and a nonlinear modification to the linear scattering obtained with the presence of a LF pulse. This nonlinear modification of the scattered signal is referred to as the nonlinear scattering component of elastic waves in the heterogeneous material, or the nonlinearly scattered wave or signal.

For materials where the elasticity can be approximated to the $2^{nd}$ order in the pressure, the elastic parameters and hence the nonlinearly scattered signal will be approximately linear in the amplitude of the LF pressure at the location of the HF pulse. For micro gas-bubbles in fluids with diameter much less than the acoustic wavelength, the elastic compression is more complex than the $2^{nd}$ order approximation to elasticity. For the first, do gases show a stronger nonlinear elasticity where higher order than the $2^{nd}$ order term in the pressure in Eq. (1) must be included. For the second, when the bubble diameter is much smaller than the acoustic wave length in the fluid, one obtains large shear deformation of the fluid around the bubble when the bubble diameter changes. This shear deforming fluid behaves as a co-oscillating mass that interacts with the bubble elasticity to form a resonant oscillation dynamics of the bubble diameter. The volume of this co-oscillating mass is approximately 3 times the bubble volume.

The scattering from such micro-bubbles will then depend on both the frequencies and the amplitudes of the LF and HF pulses. For frequencies well below the resonance frequency, the bubble compression is dominated by the nonlinear bubble elasticity, which for high pressure amplitudes requires higher than $2^{nd}$ order approximation in the pressure. For frequencies around the resonance, one gets a phase shift of around 90 deg between the pressure and the volume compression. For frequencies well above the resonance frequency the bubble compression is dominated by the co-oscillating mass with a phase shift of 180 deg to the incident pressure, which gives a negative compliance to the pressure.

Gas bubbles can be found naturally in an acoustic medium, such as the swim bladder of fish and sea creatures, gas bubbles that form spontaneously in divers and astronauts during decompression, etc. Micro-bubbles are used for ultrasound contrast agent in medicine, but their density in tissue is usually so low that their effect on the wave propagation can usually be neglected, where they are mainly observed as local, nonlinear point scatterers. The forward pulse propagation therefore usually observes a $2^{nd}$ order elasticity of the surrounding tissue that produces a nonlinear propagation lag according to Eq. (3). With high densities of bubbles in blood filled regions like the heart ventricles and blood vessels, the micro-bubbles can have marked nonlinear effect on the pressure variation of the wave propagation velocity, and also introduce a frequency dependent propagation velocity (dispersion) due to bubble resonances. With the method according to this invention, one can estimate the nonlinear propagation lag and pulse form distortion produced by the gas bubbles in the blood, and hence separate the accumulative, forward propagation effect of the bubbles and the local nonlinear scattering from the bubbles. Further details on the scattering from micro-bubbles are discussed in relation to Eqs. (35, 36, 40).

For this most general situation we can then model the received HF signal for the transmitted pulse complexes 101 and 104 as $$s_1(t) = p_{h1} x_l(t - \tau_1(t)) + x_{n1}(t - \tau_1(t); p_{h1}, p_{l1}) \quad a)$$

$$s_2(t) = p_{h2} x_l(t - \tau_2(t)) + x_{n2}(t - \tau_2(t); p_{h2}, p_{l2}) \quad b) \quad (4)$$

where $p_{h1,h2}(t)$ are the HF pulses (103/106) with amplitudes $p_{h1,h2}$, and $p_{l1,l2}(t)$ are the LF pressure pulses (102/106) with amplitudes $p_{l1,l2}$. A change of polarity of the HF and LF pulses is then represented by a change in sign of $p_{h1,h2}$ or $p_{l1,l2}$. $\tau_{1,2}(t)$ are the nonlinear propagation delays of the HF pulses 103/106 as a function of the fast time t, produced by the nonlinear manipulation of the wave propagation velocity for the HF pulses by the LF pulses 102/105 in FIG. 1A. We define $p_l = p_{l2}/p_{l1}$ as the ratio of the two LF pulses which gives $\tau_2(t) = p_l \tau_1(t)$ for $2^{nd}$ order propagation elasticity. The nonlinearly scattered HF signals from the two pulse complexes 101 and 104 are $x_{n1}(\ldots)$ and $x_{n2}(\ldots)$. The linearly scattered signal is proportional to the HF amplitude and is listed as $p_{h1} x_l(t)$ and $p_{h2} x_l(t)$ for the HF pulses 103 and 106, where $x_l(t)$ is the signature of the linearly scattered signal. For materials where the nonlinear elasticity can be approximated to the $2^{nd}$ order in the pressure, the nonlinearly scattered signal can be approximated as $$x_{n1}(t; p_{h1}, p_{l1}) \approx p_{h1} p_{l1} x_n(t)$$

$$x_{n2}(t; p_{h2}, p_{l2}) \approx p_{h2} p_{l2} x_n(t) \quad (5)$$

By estimation of the nonlinear propagation delay $\hat{\tau}(t)$ as an estimate $\tau_1(t)$, for example as described in U.S. patent application Ser. No. 11/189,350 (US Pat Pub 2005/0277835) and U.S. Pat. No. 8,038,616, we can eliminate the linearly scattered term from Eq. (4) to produce an estimate of the nonlinear scattering $$x_{ne}(t) = \frac{p_{h2} s_1(t + \hat{\tau}(t)) - p_{h1} s_2(t + p_l \hat{\tau}(t))}{p_{h2} p_{h1} p_{l1} - p_{h1} p_{h2} p_{l2}} \quad (6)$$

$$= \frac{p_{h2} x_{n1}(t; p_{h1}, p_{l1}) - p_{h1} x_{n2}(t; p_{h2}, p_{l2})}{p_{h2} p_{h1} p_{l1} - p_{h1} p_{h2} p_{l2}} = x_n(t)$$

where the last equality is found with the $2^{nd}$ order elasticity approximation for the nonlinear scattering in Eq. (5).

The Mechanical Index (MI) is given by the negative pressure swing of the pulse complex and is often limited by safety regulations to avoid cavitation and destruction of the object. In such situations the amplitude of both the LF pulse 105 and the HF pulse 106 of the pulse complex 104 can have stronger limitations than the amplitudes for the pulse complex 101. One then can have advantage of operating with lower amplitudes of the pulse complex 104 compared to pulse complex 101. This difference in amplitudes is then taken care of by $p_{h2}$ and $p_{l2}$. For practical reasons in the signal processing it can sometimes be interesting to invert the polarity of the second HF pulse 106 compared to the $1^{st}$ HF pulse 103, a modification that is taken care of by a negative value of $p_{h2}$. The subtraction of the signals $p_{h2} s_1$ and $p_{h1} s_2$ in Eq. (4) is then changed to a sum. The coefficients $p_{h1}/p_{h2}$ and $p_{l1}/p_{l2}$ also take care of inaccuracies in the transmit amplifiers and modifications of the pulse amplitudes due to nonlinear propagation and diffraction, this modification being different from the positive and negative pulses. In case of inaccuracies in the transmitters, and unknown nonlinear propagation modification of the amplitudes, one can for example estimate $p_{h1}/p_{h2}$ and $p_{l1}/p_{l2}$ from a minimization of the power in $x_{ne}$ as described in the U.S. patent application Ser. No. 11/189,350 (US Pat Pub 2005/0277835) and U.S. Pat. No. 8,038,616 and also in the combination with a minimization of the power in $x_{le}$ of Eq. (13) described below.

The nonlinearly scattered signal has shown to enhance the image contrast for:
  soft scatterers (high bulk compliance and nonlinear elasticity) as for example gas bubbles either found naturally or injected as contrast agent micro-bubbles, liposomes and other fatty structures, polymers, wax on the inside wall of oil & gas pipes, etc., and
  hard scatterers (low bulk compliance and nonlinear elasticity) as micro calcifications, gall- and kidney-stones, connective tissue, scales on the wall of oil and gas pipes, metal objects like mines buried in the sea bed, etc.

We see from Eq. (3) that the gradient in fast time (depth-time) of the estimated nonlinear propagation delay is $$\frac{d\tau(t)}{dt} = \beta_n(r(t))\kappa(r(t))p_{LF}(r(t)) \quad (7)$$

where r(t) is the integrated depth variable that for back scatter imaging is $$r(t) = \int_{\Gamma(r)} c(\tau)d\tau \approx \frac{c_0 t}{2} \quad (8)$$

where the approximation is done with approximately constant propagation velocity $c_0$ for back scattered (divide by 2) signals. The gradient in Eq. (7) hence represents the local nonlinear propagation parameters of the object. The low frequency is so low that one can most often neglect individual variations in power absorption and wave front aberrations, and measure or calculate in computer simulations the LF pressure at the location of the HF pulse at any position along the beam. Dividing said local nonlinear propagation parameter with this estimated local amplitude of the manipulating LF pressure, one obtains a quantitative local nonlinear propagation parameter that represents local quantitative elasticity parameters of the object, as $$np(r(t)) = \frac{1}{p_{LF}(r(t))}\frac{d\tau(t)}{dt} = \beta_n(r(t))\kappa(r(t)) \quad (9)$$

This parameter can be used to characterize the material, where for example in soft biological tissues fat or high fat content gives a high value of $\beta_n\kappa$.

The LF field simulation must however be done with defined parameters of the mass density $\rho$ and compressibility $\kappa$, and in the actual material one can have deviations from the parameters used for simulation, particularly in heterogeneous materials where the parameters have a spatial variation. When the load material has low characteristic impedance compared to the output mechanical impedance of the transducer elements, the vibration velocity of the element surface $u_{LF}(0)$ is close to independent of the load material characteristic impedance, and hence given by the electric drive voltage. Assume that we carry through the simulations with a characteristic impedance $Z_S = \sqrt{\rho_S/\kappa_S} = \rho_S c_S = 1/\kappa_S c_S$ where the subscript S denotes values used for simulation. When the surface characteristic impedance deviates from the simulation value we get the pressure at the transducer element surface as $p_{LF}(0)=(Z(0)/Z_S)p_S(0)$ where Z(0) is the characteristic impedance of the actual load material at the element surface. The intensity is related to the pressure as $I=p^2/2Z$, and when the characteristic impedance changes throughout the load material, the intensity is kept constant as scattering at the low frequencies is low and can be neglected, and one can then relate the actual pressure to the simulated pressure $p_S(r)$ as $$p_{LF}(r) = \sqrt{\frac{Z(r)}{Z(0)}}\frac{Z(0)}{Z_S}p_S(r) = \sqrt{\frac{Z(r)Z(0)}{Z_S}}p_S(r) \quad (10)$$

As one do not know the actual material parameters, and one normalizes with $p_S(r)$ in Eq. (9) the quantitative nonlinear propagation parameter is related to the material parameters as $$np(r) = \quad (11)$$

$$\frac{p_{LF}(r)}{p_S(r)}\beta_n(r)\kappa(r) = \frac{\sqrt{Z(r)Z(0)}}{Z_S}\beta_n(r)\kappa(r) = \beta_n(r)\frac{c_S\kappa_S}{\sqrt{c(0)c(r)}}\sqrt{\frac{\kappa(r)}{\kappa(0)}}$$

One hence see that quantitative estimates of elasticity parameters can be obtained from the fast time gradient of estimates of the nonlinear propagation time lag. As such estimates are noisy, the gradient must be obtained through band limited differentiation, but one can also use a model based estimation where an estimate of the nonlinear propagation delay is estimated from simulations of the composite LF/HF pulse fields with given local elasticity parameters, and the parameters are adjusted in an estimation algorithm that produces the same simulated nonlinear propagation lag as the estimated one, according to known methods.

One can also obtain a local nonlinear scattering parameter as follows: The envelope of the nonlinearly scattered signal as a function of range $r=c_0 t/2$ is proportional to $$a_{ne}(r) = Env\{x_{ne}(2r/c_0)\} \sim k_{HF}^2 v_n(r)p_{LF}(r)G(r)\exp\left\{-2f_{HF}\int_0^r ds\mu(s)\right\} \quad (12)$$

where $k_{HF}=\omega_{HF}/c_0$ is the wave vector for the center high frequency $\omega_{HF}=2\pi f_{HF}$, $v_n(r)$ is a nonlinear scattering parameter for the HF band laterally averaged across the receive beam, G(r) is a depth variable gain factor given by beam shape and receiver depth variable gain settings, and the exponential function represents ultrasound power absorption in the HF band. Under the assumption of a material with $2^{nd}$ order elasticity where Eq. (5) is valid, the linearly scattered component can be extracted from the received HF signals in Eq. (4) as $$x_{le}(t) = \frac{p_{h1}p_{l1}s_2(t+p_l\hat{\tau}(t)) - p_{h2}p_{l2}s_1(t+\hat{\tau}(t))}{p_{h1}p_{h2}(p_{l1}-p_{l2})} \quad (13)$$

When $x_{n1}$ and $x_{n2}$ are of the more general form in Eq. (4) as found for micro-bubbles, the nonlinear component is usually small compared to the linear scattering from the tissue and is found only at the discrete locations of the micro-bubbles and so that the expression in Eq. (13) is a good approximation also in these cases. In fact, any of Eq. (4a, b) with delay correction can often be used as an estimate of the linearly scattered signal because the nonlinearly scattered signal is found at local points and often has much less amplitude than the linearly scattered signal. The envelope of the linearly scattered signal as a function of range r is similarly proportional to $$a_{le}(r) = Env\{x_{le}(2r/c)\} \sim k_{HF}^2 v_l(r)G(r)\exp\left\{-2f_{HF}\int_0^r ds\mu(s)\right\} \quad (14)$$

where $v_l(r)$ is a linear scattering parameter for the HF band and the other variables are as in Eq. (12).

We note that the linearly and nonlinearly scattered signal components have the same amplitude variation due to beam divergence/convergence and power absorption, and one can obtain a local nonlinear scattering parameter by forming the ratio of the envelopes $a_{ne}(r)$ and $a_{le}(r)$ as $$\frac{a_{ne}(r)}{a_{le}(r)} = \frac{v_n(r)}{v_l(r)} p_{LF}(r) \quad (15)$$

further dividing by an estimate of the local LF pressure as in Eq. (9), one obtains a quantitative local nonlinear scattering parameter as $$ns(r) = \frac{a_{ne}(r)}{a_{le}(r) p_{LF}(r)} = \frac{v_n(r)}{v_l(r)} \quad (16)$$

and using a simulated LF pressure we get $$ns(r) = \frac{a_{ne}(r)}{a_{le}(r) p_S(r)} = \frac{p_{LF}(r)}{p_S(r)} \frac{v_n(r)}{v_l(r)} = \frac{\sqrt{Z(r)Z(0)}}{Z_S} \frac{v_n(r)}{v_l(r)} \quad (17)$$

Variations in both the quantitative local nonlinear propagation parameter and the local nonlinear scattering parameter of the object with heating or cooling of the object can then be used to assess local temperature changes of the object, for example with thermal treatment of the object. The temperature dependency of the propagation velocity (dc/dT) of soft tissue in medical ultrasound, depends on the tissue composition where for fat or large fat content one has dc/dT<0 while for other tissues, like liver parenchyma, one has dc/dT>0 and predictable. One or both of np~$\beta_n\kappa$ from Eqs. (9, 11) and ns~$v_n/v_l$ from Eqs. (16, 17) can then be used to estimate the fat content and hence dc/dT in the tissue, so that variations in the propagation lag with heating or cooling can be used to assess temperature.

The phase relation between the HF and LF pulses as shown in FIG. 1A, can only be achieved over the whole propagation path for the near field region of the LF beam, which in practice means that the HF image range must be within the near field of the LF aperture. This can be an unfocused LF aperture producing a close to plane LF wave, but also the near field region 203 of a focused beam as shown in FIG. 2A. For example could one use a slightly focused LF aperture to produce some LF beam convergence in the near field region to compensate for the weak absorption of the LF pulse often found. The HF transmit beam is generally focused, and for a plane wave or differently focused LF beam, there will be a sliding of the position of the HF pulse relative to the LF pulse across the focused HF beam wave front. The nonlinear propagation delay for the HF pulse will hence vary across the HF pulse wave front and hence produce a nonlinear focus modification of the HF beam, where the focus modification will depend on the polarity and amplitude of the LF pulse. For precise suppression of the linear scattering this focus modification can be accounted for in the corrected, preset HF transmit focus delays, or as a correction in the delay, pulse form, and amplitude of the received HF signal, or a combination of theses.

To maintain an adequate collimation of the LF beam, one do often have to focus the LF beam. For such practical, diffraction limited beams there will be a sliding between the relative position of the HF and LF pulses throughout the depth of the beam. This phenomenon is further described with reference to FIG. 2A, which shows typical LF and HF apertures 201 and 208 with diameters $D_{LF}$ and $D_{HF}$, respectively, both focused at 202. The lines 203 shows the geometric boundaries for a LF beam without diffraction, while 204 describes the LF beam diffraction cone with diffraction opening angle $\theta_{LF}=2\lambda_{LF}/D_{LF}$ where $\lambda_{LF}$ is the LF wave length and $D_{LF}$ is the LF aperture diameter. The LF beam is essentially determined by the outermost of these boundaries, where in the near field region 205 the beam width reduces with depth by the geometric cone as it is wider than the diffraction cone, while in the focal region 206 the beam is diffraction limited and the beam width expands with the diffraction cone where this is the widest, and further in the far field region 207 the beam expands again with the geometric cone which again is wider than the diffraction limited cone. The LF pressure pulse in the focal point 202 is the temporal derivative of the LF pressure pulse at the transducer array surface, and throughout the focal region the phase of the LF pulse slides $\pi$ radians, with $\pi/2$ radian in the focus to present a temporal differentiation. This provides a sliding of the position of the HF pulse relative to the LF pulse of $T_{LF}/4$ in the focus and further $T_{LF}/4$ in the far-field cone, where $T_{LF}$ is the temporal period of the LF pulse.

The field from a flat (unfocused) LF aperture is given by the modification of FIG. 2A where the focal point 202 is moved to infinite distance from the aperture, where again the LF pulse is the temporal derivative of the LF pulse on the array surface. The near field will then be a cylindrical extension of the LF aperture where the LF pulse is close to the same as on the array surface, and the diffraction limited far-field can be defined to start where the diffraction limited cone exceeds this cylindrical extension at $r=D_{LF}^2/2\lambda_{LF}$. Inside this limit the LF field is well approximated by a plane wave, where a fixed phase relation between the HF and LF pulses as in FIG. 1A is maintained for the whole range.

The HF pulse undergoes a similar differentiation from the transducer array surface to its own focal region, but as the HF pulse is much shorter than the LF pulse, it is the sliding of the LF pulse phase that affects the phase relationship between the HF and LF pulses. The receive HF beam do generally have dynamic focusing and aperture, where we mainly will observe the interaction between the HF and LF pulses close to the HF beam axis. Variations of the phase between the HF and LF pulse across the HF transmit beam will nonlinearly affect the focus of the transmitted HF beam and can be accounted for in the HF transmit focus delays, or as a correction of the received HF signal as discussed below. The on-axis HF beam will however with propagation distance be influenced by the off-axis HF pulse form due to the diffraction nature of wave propagation. However, this effect is small, and the following holds in a 1$^{st}$ approximation analysis that generally produce adequate results: For the on-axis HF pulse to be found at the crest of the LF pulse in the focal region, shown as 209, FIG. 2A(1) the HF pulse must due to the differentiation of the LF pulse in the LF focus be transmitted at the array surface at the zero crossing with the negative spatial gradient of the LF pulse, shown as 210, FIG. 2A(2). In the same way, for the on-axis HF pulse to be found at the trough of the LF pulse in the focal region, shown as 211, FIG. 2A(3) the HF pulse must at the array surface be transmitted at the zero crossing with the positive spatial gradient of the LF pulse, shown as 212, FIG. 2A(4). The position of the HF pulse within the LF pulse complex will hence slide $\lambda_{LF}/4$ from the array surface to the focus (or far field for unfocused LF beam).

Figure 1B:
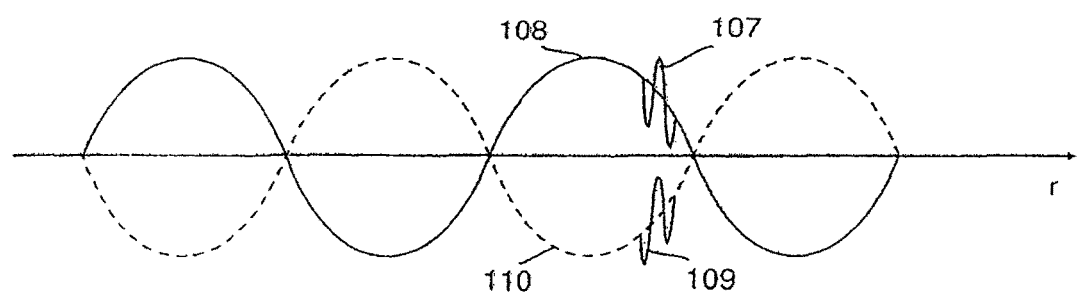

Hence, in the near field region where the HF pulse is found at a gradient of the LF pulse as illustrated in FIG. 1B, the different parts of the HF pulse will propagate with different velocities leading to a pulse compression for the HF pulse 107 that propagates on a negative spatial gradient of the LF pulse 108, because the tail of the pulse propagates faster than the front of the pulse. Similarly one gets a pulse stretching of the HF pulse 109 that propagates on a positive spatial gradient of the LF pulse 110, because the tail of the pulse propagates slower than the front of the pulse. With more complex variations of the LF pulse pressure within the HF pulse, one can get more complex distortions of the HF pulse shape. For example, if the HF pulse is long, or one have less difference between the high and low frequencies, one can get variable compression or stretching along the HF pulse, and even compression of one part and stretching of another part. One can then even get non-negligible distortion of the HF pulse when its center is located at a crest or trough of the LF pulse. As the pulse is distorted, the frequency content is changed which changes the diffraction. Absorption also increases with frequency and also produces a down-sliding of the pulse center frequency. The total pulse distortion is hence a combination of the spatial variation in the propagation velocity along the HF pulse produced by the nonlinear elasticity manipulation of the LF pulse, diffraction, and absorption.

We assume a dynamically focused receive beam that is so narrow that the variation of the transmitted, distorted HF pulse at a depth $r=ct_0/2$ is negligible across the receive beam (see comments after Eq. (3)). The effect of pulse form distortion on the received signal can then be modeled by a filter as $$s_k(t) = \int dt_0 v_k(t-t_0,t_0) x_k(t_0 - \tau_k(t_0)) = s_{lk}(t) + s_{nk}(t)$$

$$x_k(t_0) = x_{lk}(t_0) + x_{nk}(t_0) \qquad (18)$$

where $v_k(t,t_0)$ represents the change in frequency content of the received HF signal due to pulse form distortion. $x_k(t_0)$ represents the scattered signal that would have been obtained without pulse form distortion and nonlinear propagation delay at the fast time $t_0$ with a nonlinear propagation delay $\tau_k(t_0)$. $x_{lk}(t_0)$ is the linearly scattered signal that varies with k because the transmitted HF amplitude and polarity can vary, but also because diffraction and the power in harmonic components of the HF pulse can depend on the LF pulse. $x_{nk}(t_0)$ is the nonlinearly scattered signal for a transmitted LF pulse $p_{lk}(t_0)$, and it depends on the pulse number k because the LF pulse and potentially the HF pulse varies with k. For materials with $2^{nd}$ order elasticity $x_{nk}(t_0)$ is proportional to the LF and HF amplitudes as in Eq. (5), while for micro-bubbles the nonlinear dependency is more complex where even the scattered HF pulse form from the micro-bubble can depend on the LF pressure as discussed in relation to Eqs. (35, 36) below. The linear effect of variations in the amplitude and polarity of the HF pulse can be included in $v_k(t,t_0)$, while the nonlinear effect is included in the k variation of $x_{nk}(t_0)$.

Even if there is some variation of the transmitted, distorted HF pulse across the HF receive beam, Eq. (18) gives an adequate signal model where $v_k(t,t_0)$ now represents an average pulse distortion across the beam with the weight of the scattering density. This weighting of the scattering density introduces a rapidly varying component of $v_k(t,t_0)$ with the depth time $t_0$, that depends on the randomly varying scattering density. This component can introduce added noise in estimates of $v_k(t,t_0)$ from the received signal.

Figure 2B:
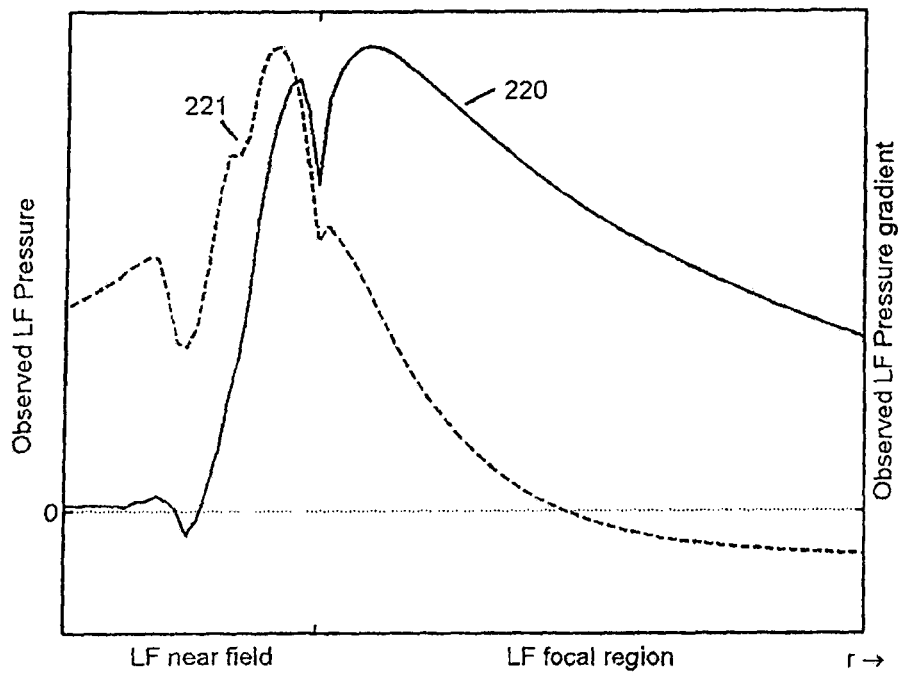
FIGS. 2B and 2C show the results of a simulation of the effect of the observed LF pressure gradient on the HF pulse as a function of depth.
Figure 2C:
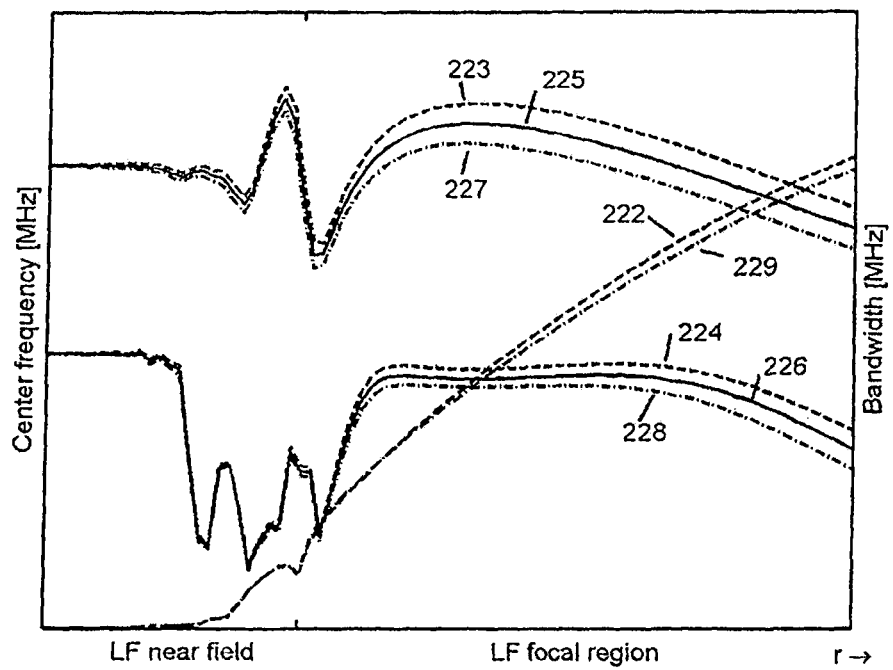

In FIG. 2B and FIG. 2C are shown results of a simulation of the effect of the observed LF pressure and LF pressure gradient on the HF pulse as a function of depth. The HF pulse is placed at the negative spatial gradient of the LF pulse at the array surface. 220 shows the observed LF pressure at the center of the HF pulse, while 221 shows the observed LF pressure gradient at the center of the HF pulse, both as a function of depth r. The observed LF pressure is given by the LF pressure amplitude as a function of depth, influenced by diffraction and absorption, and the local position of the HF pulse relative to the LF pulse. In the near field the HF pulse is near a zero crossing of the LF pulse and the observed LF pressure is hence low, while the observed LF pressure gradient is high. As the pulse complex propagates into the focal region, the LF pressure amplitude increases and the HF pulse slides towards the crest of the LF pulse, which increases the observed LF pressure while the observed LF pressure gradient drops.

The resulting nonlinear propagation delay of the HF pulse for the positive LF pulse is shown as 222 in FIG. 2C, together with the center frequency 223 and the bandwidth 224 of the HF pulse. The center frequency and the bandwidth of the HF pulse for zero LF pulse is shown as 225 and 226 for comparison. We note that in the near field the observed LF pressure gradient produces an increase of both the center frequency and the bandwidth of the HF pulse that accumulates with depth, compared to the HF pulse for zero LF pressure. The nonlinear propagation delay is low as the observed LF pressure is low. As the pulse complex enters the LF focal region, the increased observed LF pressure produces an accumulative increase in the nonlinear propagation delay, 222, while the drop in the pressure gradient along the pulse reduces the increase in the difference between the center frequency and bandwidth of the HF pulses. Moving into the far-field, the LF amplitude drops due to the geometric spread of the beam and both the observed LF pressure and pressure gradient at the HF pulse drops. The HF pulse also slides relative to the LF pulse to finally place the HF pulse at a zero crossing of the LF pulse, but this sliding is slower than in the near field.

The dash-dot curves 227 and 228 shows the mean frequency and the bandwidth of the HF pulse for opposite polarity (negative) of the LF pulse. The dash-dot curve 229 shows the negative nonlinear propagation delay, $-\tau_k(t)$, with opposite polarity of the LF pulse. In this example, the HF pulse is short compared to the LF wave length, so that the LF pulse gradient mainly produces a HF pulse length compression/expansion. The HF pulse bandwidth then follows the HF pulse center frequency as is clear in FIG. 2C. With longer HF pulses relative to the LF period there will be a more complex distortion of the HF pulse, where one needs more parameters than the center frequency and the bandwidth to describe the distortion, as discussed in relation to FIG. 1B above and in relation to Eq. (26).

Due to the relative sliding between the HF and LF pulses with depth, it is in many situations convenient to adjust the transmit phase relationship between the HF and LF pulses, to obtain best possible relative location in the actual image depth. Such adjustments can be manual or automatic, or a combination of both.

The nonlinear propagation delay, Eq. (3), changes accumulatively with depth, which implies that the fast time variation of $\tau_k(t)$ is fairly slow. This allows us to do the following approximation $$s_k(t) \approx z_{lk}(t-\tau_k(t)) + z_{nk}(t-\tau_k(t))$$

$$z_{lk}(t) = \int dt_0 v_k(t-t_0,t_0) x_{lk}(t_0) \quad z_{nk}(t) = \int dt_0 v_k(t-t_0,t_0) x_{nk}(t_0) \qquad (19)$$

With the same approximation we can select an interval $T_i=T(t_i)$ around $t_i$, and approximate $v_k(t,t_0) \approx v_k(t,t_i)$ in this interval. This allows us to do a Fourier transform of Eq. (19) as $$S_k(\omega,t_i) = V_k(\omega,t_i) X_k(\omega) e^{-i\omega\tau_k(t_i)} \quad (20)$$

where we have also approximated $\tau_k(t_0) \approx \tau_k(t_i)$ over the interval $T(t_i)$. We then can device a pulse distortion correction filter, for example as a Wiener filter approximation to the inverse filter given by the formula $$V_k(\omega, t_i)^{-1} \approx H_k(\omega, t_i) = \frac{1}{V_k(\omega, t_i)} \frac{1}{1 + N/|V_k(\omega, t_i)|^2} \quad (21)$$

where N is a noise power parameter to avoid noisy blow-up in $H_k(\omega,t_i)$ where the amplitude of $V_k(\omega,t_i)$ is low compared to noise in the measurement, while we get an inverse filter when the amplitude is sufficiently high above the noise, i.e.

$$H_k(\omega, t_i) \approx \begin{cases} \dfrac{1}{V_k(\omega, t_i)} & \text{for } |V_k(\omega, t_i)|^2 \gg N \\ \dfrac{1}{N} V_k^*(\omega, t_i) & \text{for } |V_k(\omega, t_i)|^2 \ll N \end{cases} \quad (22)$$

We hence can correct the received signal for the nonlinear propagation delay and pulse form distortion with the following filter $$\hat{X}_k(\omega,t_i) = H_k(\omega,t_i) S_k(\omega,t_i) e^{i\omega\tau_k(t_i)} \quad (23)$$

Inverse Fourier transform of $H_k(\omega,t_i)$ in Eq. (21) gives a filter impulse response as $h_k(t,t_i)$. Fourier inversion of Eq. (23) and interpolation between $t_i$ gives an impulse response that is continuous in $t_0$, and we can write the nonlinear delay and pulse distortion corrected signal in the time domain as $$\hat{x}_k(t) = \int dt_0 h_k(t-t_0,t_0) s_k(t_0 + \tau_k(t_0)) \quad (24)$$

The nonlinear delay correction can be included in the inverse filter impulse response $h_k(t-t_0,t_0)$, but for calculation efficiency it is advantageous to separate the correction for nonlinear propagation delay as a pure delay correction where the filter then corrects only for pulse form distortion, as the filter impulse response then becomes shorter. The signal is normally digitally sampled, and Eqs. (18-24) are then modified by the sampled formulas known to anyone skilled in the art. The length of $T(t_i)$ would typically be a couple of HF pulse lengths, and one would typically use intervals that overlap down to the density that $t_i$ represents each sample point of the received signal. When the pulse distortion can be approximated by a time compression-expansion, the received signal from a point scatterer can be written as $w_k(t,t_i;b_k) = u(b_k t, t_i) = \int dt_1 v_k(t-t_1,t_i) u(t_1,t_i)$ where $b_k = 1+a_k$ is the time compression factor and $u(t_1,t_i)$ is the undistorted received pulse from the point scatterer. We can then write $$V_k(\omega, t_i; b_k) = \frac{U(\omega/b_k, t_i)}{b_k U(\omega, t_i)} \frac{1}{1 + N_V/|U(\omega, t_i)|^2} \quad (25)$$

$$H_k(\omega, t_i; b_k) = \frac{U(\omega, t_i)}{U(\omega/b_k, t_i)} \frac{b_k}{1 + N_H/|U(\omega/b_k, t_i)|^2}$$

where $U(\omega,t_i)$ is the Fourier transform of the undistorted received pulse form from depth interval $T_i$ obtained with zero LF. The LF pulse is often at such a low frequency that individual variations of the acoustic LF pulse absorption between individuals in a specific type of measurement situation, can be neglected as discussed above. One can then use simulated or measured values of the LF pulse field at the location of the HF pulse, as a basis for estimation of the HF pulse form distortion $v_k(t,t_i)$. An uncertainty in this simulation is the actual nonlinear elasticity of the object. The invention devices several methods to assess the nonlinear elasticity, and also direct estimation of $H_k(\omega,t_i)$ from the signals as discussed following Eq. (52) below.

When the LF pressure gradient has larger variation along the HF pulse length so that the pure time compression/expansion is no longer an adequate approximation of the HF pulse distortion, we can do a polynomial modification of the time scale as $$w_k(t, t_i; \underline{a}_k) = u((1+a_{k1})t - a_{k2}t^2 + a_{k3}t^3 - \ldots, t_i) = \int dt_1 v_k(t-t_1, t_i; \underline{a}_k) u(t_1, t_i) \quad (26)$$

$$V_k(\omega, t_i; \underline{a}_k) = \frac{W(\omega, t_i; \underline{a}_k)}{U(\omega, t_i)} \frac{1}{1 + N_V/|U(\omega, t_i)|^2}$$

$$H_k(\omega, t_i; \underline{a}_k) = \frac{U(\omega, t_i)}{W(\omega, t_i; \underline{a}_k)} \frac{1}{1 + N_H/|W(\omega, t_i; \underline{a}_k)|^2}$$

where $\underline{a}_k = (a_{k1}, a_{k2}, a_{k3}, \ldots)$. After the correction for nonlinear propagation delay and pulse form distortion, the received signals from at least two pulse complexes can be combined as in Eqs. (6, 13) to extract the nonlinearly and linearly scattered signal from the object.

In another method according to the invention, one does a depth variable frequency mixing, as known to anyone skilled in the art, of the received HF signal with nonzero transmitted LF pulse so that the center frequency of the HF signal for example is moved to the vicinity of the received HF signal with zero LF pulse, 225 of FIG. 2C. This frequency shift do not change the bandwidth of the received HF signal, where the bandwidth can be modified with fast time filtering of the frequency mixed HF signal. We also note that this frequency mixing could be used to bring all received HF signals to the same, or approximately the same, center frequency of any value, for example zero center frequency which would be the well known IQ-demodulation. In the bandwidth filtering we could also reduce the bandwidth of all signals to that of the signal with lowest bandwidth, for example 228 of FIG. 2C, as bandwidth reduction is a robust operation and this operation would produce similar received HF pulse from point scatterers for all the signals. We note though that reducing the bandwidth also reduces the range resolution, but improved suppression of pulse reverberation noise and extraction of nonlinear scattering signal is often preferable relative the reduced range resolution.

We note that this situation is somewhat different from that where all the pulse form correction is done with a filter, as in Eqs. (21-26). In Eqs. (21-26) one wants to correct the HF pulse form of all the received signals to a signal with center frequency around the middle of the center frequencies of all received HF signals, which often is the received HF signal for zero LF pulse. We note that in the above methods one would generally correct for the nonlinear propagation delay separately as this allows for shorter fast time response of the correction filters, although in principle the delay correction could be included in the fast time correction filter.

Figure 2D:
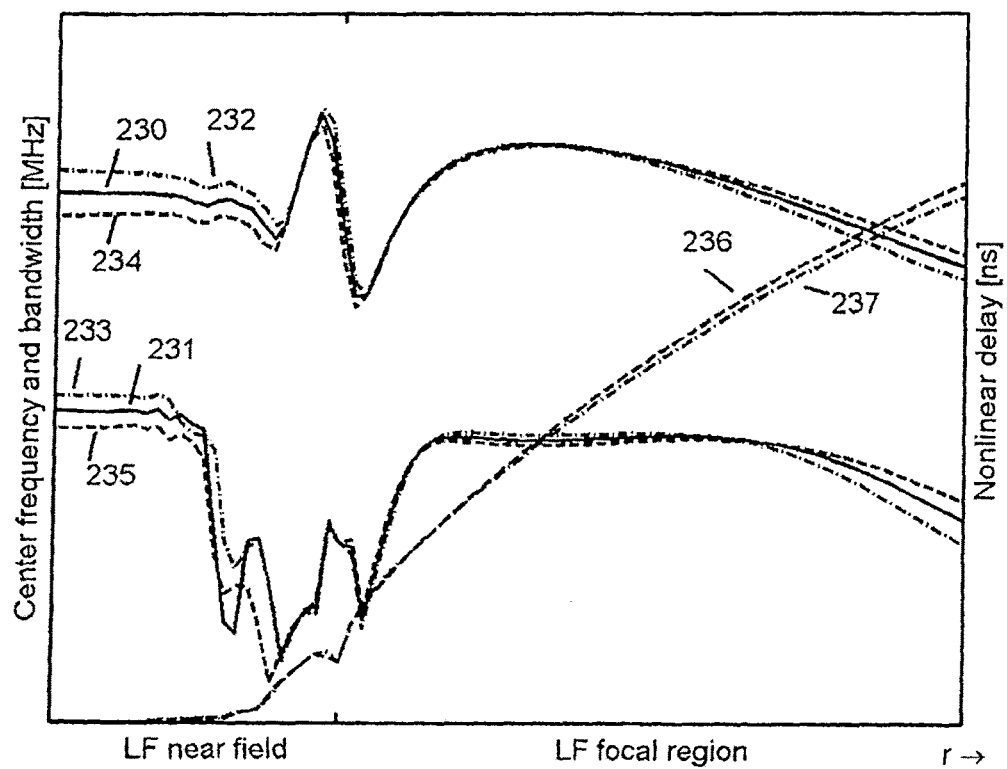
FIG. 2D shows the results of variations in the transmitted pulses.

In yet another method according to the invention, one modify (e.g. stretch or compress or more complex modification) the transmitted HF pulse, so that the pulse distortion in front of the interesting imaging range (for example the LF focal range) modifies the pulses to similar pulses for positive and negative polarity of the LF pulse within the interesting imaging range. In FIG. 2D is shown the results of such variation in the transmit pulses, where 230 and 231 shows the depth variation of the center frequency and the bandwidth of the original transmitted HF pulse with zero transmitted LF pulse, 232 and 233 shows the center frequency and the bandwidth of time expanded transmitted HF pulse and how they are modified by the co-propagating positive LF pulse, while 234 and 235 shows the center frequency and the bandwidth of time compressed transmitted HF pulse and how they are modified by the co-propagating negative LF pulse. The nonlinear propagation delay for the positive LF pulse is shown as 236 and the negative nonlinear propagation delay for the negative LF pulse is shown as 237. We note that both the center frequency and the bandwidth of the HF pulses are close to equal throughout the LF focal range. In the combination of the signals in Eq. (6) the linear scattering will then be highly suppressed for the interesting imaging range where the pulses for positive and negative polarity of the LF pulse have close to the same form. It is not possible to do a complete correction on transmit only, and a transmit correction combined with a receive correction composed of frequency mixing and/or filtering generally gives the best result. In the near field of FIG. 2D there is a difference in the HF pulses for positive and negative polarity of the LF pulse. If the signal in the near range is important, one can for example do a limited correction on transmit combined with a depth variable frequency mixing and/or fast time filter correction on receive so that the received pulse is independent on the transmitted LF pulse over the interesting image range. As for the frequency mixing, we note that we can in principle modify any of the transmitted HF pulses, also the HF pulse with zero LF pulse, so that all pulses are close in center frequency and bandwidth in a defined image range, for example that of the HF pulse with negative LF pulse.

For imaging of nonlinear scattering, it is important that the LF pressure at the HF pulse has limited variation throughout the image range. The range where the variation of the LF pressure at the HF pulse has limited variation can be extended by building up the image of multiple transmit regions, using transmit pulses with different focal depths for the different transmit regions of the image range. To obtain close to constant observed LF pressure with depth one can also use an unfocused or weakly focused LF beam with adequately wide transmit aperture so that the actual HF image range is within the LF beam near field.

In yet another method according to the invention, pulse distortion correction for pulse compression can for a limited fast time (depth-time) interval approximately be obtained by fast time expansion (stretching) of the received HF signal over that interval, and correction for pulse expansion can for a limited fast time (depth-time) interval approximately be obtained by fast time compression of the received HF signal over the limited interval. The reason why this pulse distortion correction is approximate is that it also changes the depth-time distance between scatterers over the given interval, so that the form of the signal determined by interference between scatterers at different depths becomes incorrect. We therefore can apply the time expansion/compression correction only to a limited fast time interval. For approximate pulse distortion correction over a longer fast time interval, this longer interval can be divided into shorter fast time intervals where different fast time expansion/compression is done on each interval. The corrected signals from different intervals can then be spliced to each other for example by a fade-in/fade-out windowing technique of the signals from neighboring intervals across the interval borders. There exist in the literature several methods for fast time expansion/compression of a signal, for example reading the signal in and out of a FIFO (First In First Out) memory structure at different read in and read out rates, interpolation of the signal and selecting different samples for the corrected output signal compared to the input signal, etc. We note that by the filter pulse distortion correction in Eqs. (23, 24), the interference between the scatterers is modified by the correction because we modify the scattered pulse and not the distance between the scatterers. This modifies the envelope of the distorted signal to that obtained with no pulse distortion. The frequency mixing also changes the center frequency of the received HF signal without changing the distance between the scatterers, but the signal bandwidth is unmodified which means that the pulse form from point scatterers is unmodified. Additional fast time filtering will change this pulse form as described above.

The fast time expansion/compression method is particularly interesting for low pulse distortion where it is a good approximation and a simple and fast method. For larger pulse distortions, it can be advantageous to combine the above methods of transmit pulse correction, filter correction of the received signal, frequency mixing, and fast time expansion/compression of the received signal. This specially relates to regions of very high pulse distortion, where the frequency spectrum of the distorted pulse deviates much from the frequency spectrum of the undistorted pulse, which can make filtering correction only, less robust. A limited fast time expansion/compressions of the received signal and/or frequency mixing and/or approximate correction of the transmitted HF pulse can then be used to bring the frequency spectrum of the limited corrected pulse closer to the frequency spectrum of the undistorted pulse, so that the filtering correction becomes more robust.

The LF wavelength is typically ~5-15 times longer than the HF wavelength, and to keep the LF beam adequately collimated to maintain the LF pulse pressure at deep ranges, the LF transmit aperture is preferably larger than the outer dimension of the HF transmit aperture. For the HF pulse one wants adequately long transmit focus, which limits the width of the HF transmit aperture. For further detailed analysis of this phase sliding it is convenient to study circular apertures where one have analytic expressions for the continuous wave fields (CW) along the beam axis. However, the basic ideas are also applicable to other shapes of the apertures, such as rectangular or elliptical shapes. We analyze the situation in FIG. 3A that shows a cross section of the HF (301) and LF (302) transducer arrays with indications of the boundaries of the HF beam 304 and LF beam 303. For generality of the illustration we have chosen both an LF and HF aperture where the central part is removed, so that the inner and outer diameters of the LF aperture is $D_{li}=2a_{li}$ and $D_{lo}=2a_{lo}$ respectively, and the same for the HF aperture are $D_{hi}=2a_{hi}$ and $D_{ho}=2a_{ho}$ as shown in the Figure. The removed central part of the LF radiation aperture reduces the overlap between the LF and the HF beam in the near range, indicated as the near range region 305 where the LF field has low amplitude. The nonlinear elasticity manipulation by the LF pulse is therefore very low close to the beam axis in the near range region 305, which reduces the near range nonlinear LF manipulation of the observed (close to the beam axis) transmitted HF pulse.

The continuous wave axial LF pressure field $P_l(r,\omega)$ with angular frequency $\omega=c_0 k$, is from a circular aperture at the point 306 (depth r) on the beam axis $$P_l(r, \omega) = \frac{F}{r} \frac{e^{-ikR_{li}(r)} - e^{-ikR_{lo}(r)}}{F/r - 1} P_{lt}(\omega) \quad (27)$$

$$= i2 e^{-ik(R_{lo}(r)+R_{li}(r))/2} \frac{F}{r} \frac{\sin k(R_{lo}(r) - R_{li}(r))/2}{F/r - 1} P_{lt}(\omega)$$

$$k = \omega/c_0$$

where $P_{lt}$ is the LF transmit pressure on the array surface, $R_{lo}(r)$ is the distance 307 from the outer edge of the LF array to 306 on the z-axis and $R_{li}(r)$ is the distance 308 from the inner edge of the LF array to 306. Similarly do we get the axial HF pressure field $P_h(r,\omega)$ at 306 as $$P_h(r, \omega) = \frac{F}{r} \frac{e^{-ikR_{hi}(r)} - e^{-ikR_{ho}(r)}}{F/r - 1} P_{ht}(\omega) \quad (28)$$

$$= i2 e^{-ik(R_{ho}(r)+R_{hi}(r))/2} \frac{F}{r} \frac{\sin k(R_{ho}(r) - R_{hi}(r))/2}{F/r - 1} P_{ht}(\omega)$$

$$k = \omega/c_0$$

where $P_{ht}$ is the HF transmit pressure on the array surface, $R_{ho}(r)$ is the distance 309 from the outer edge of the HF array to 306 on the beam axis-axis and $R_{hi}(r)$ is the distance 310 from the inner edge of the low frequency array to 306.

We note from the $1^{st}$ lines of the expressions in Eqs. (27, 28) that the pressure do in the near field break up into two pulses from the inner and outer edge of the apertures with delays $R_{li}(r)/c_0$ and $R_{lo}(r)/c_0$ for the LF pulse, and $R_{hi}(r)/c_0$ and $R_{ho}(r)/c_0$ for the HF pulse. This is illustrated in the upper panel of FIG. 3B where 311 shows the HF pulse and 312 shows the LF pulse at time point $t_1$ where the pulses are in the near field. The HF pulse has a center frequency of 10 MHz and the LF pulse has a center frequency of 1 MHz, both in biological tissue with assumed propagation velocity of 1540 m/sec. In the near field, absorption will reduce the pulse from the outer edge as this has the longest propagation distance to the axis. The same is found with apodization where the excitation amplitude reduces with distance from the axis.

Figure 3A:
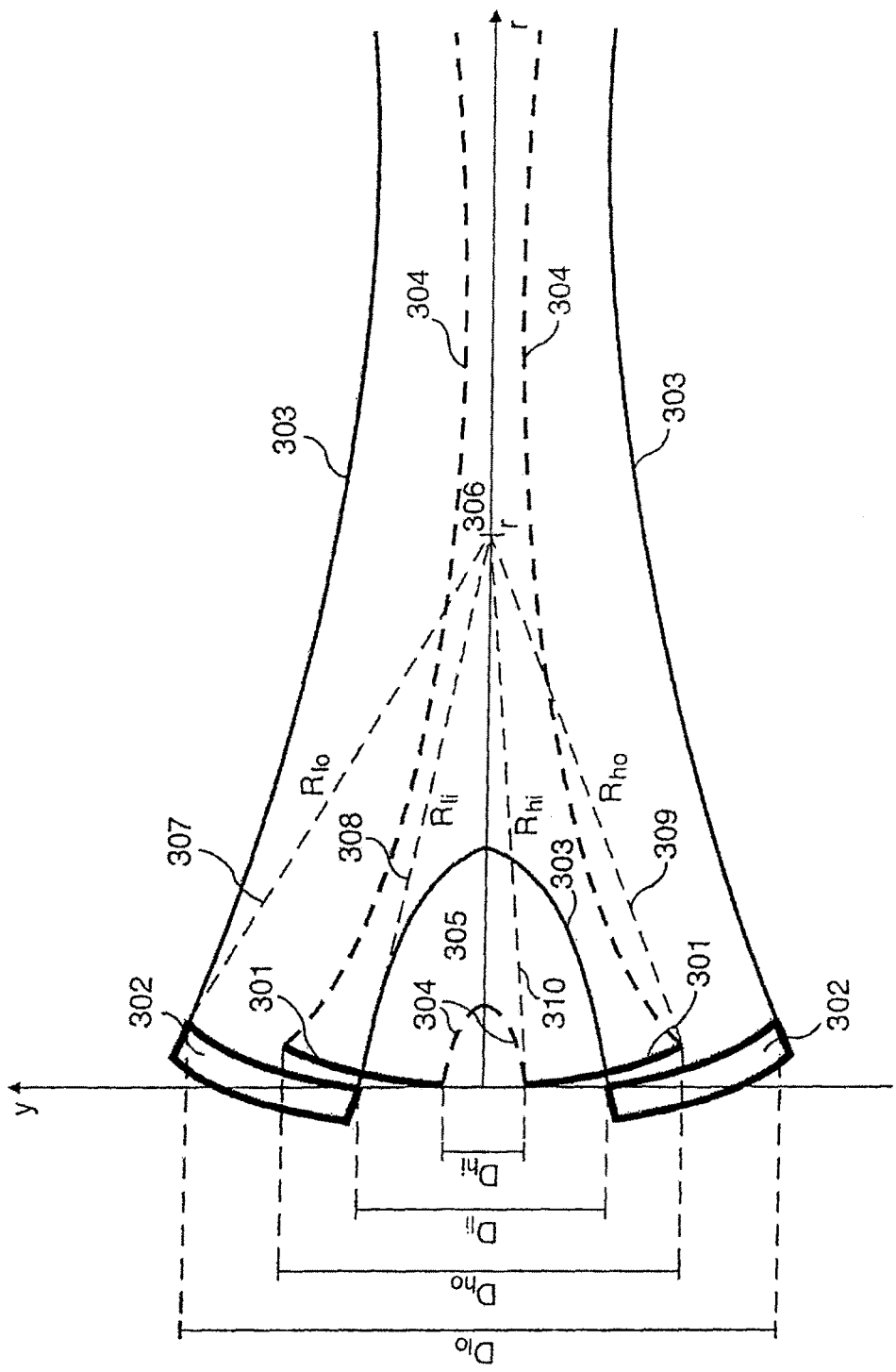
FIG. 3A shows a cross-section of the HF and LF transducer arrays with the boundaries of the HF beam and LF beam indicated.
Figure 3B:
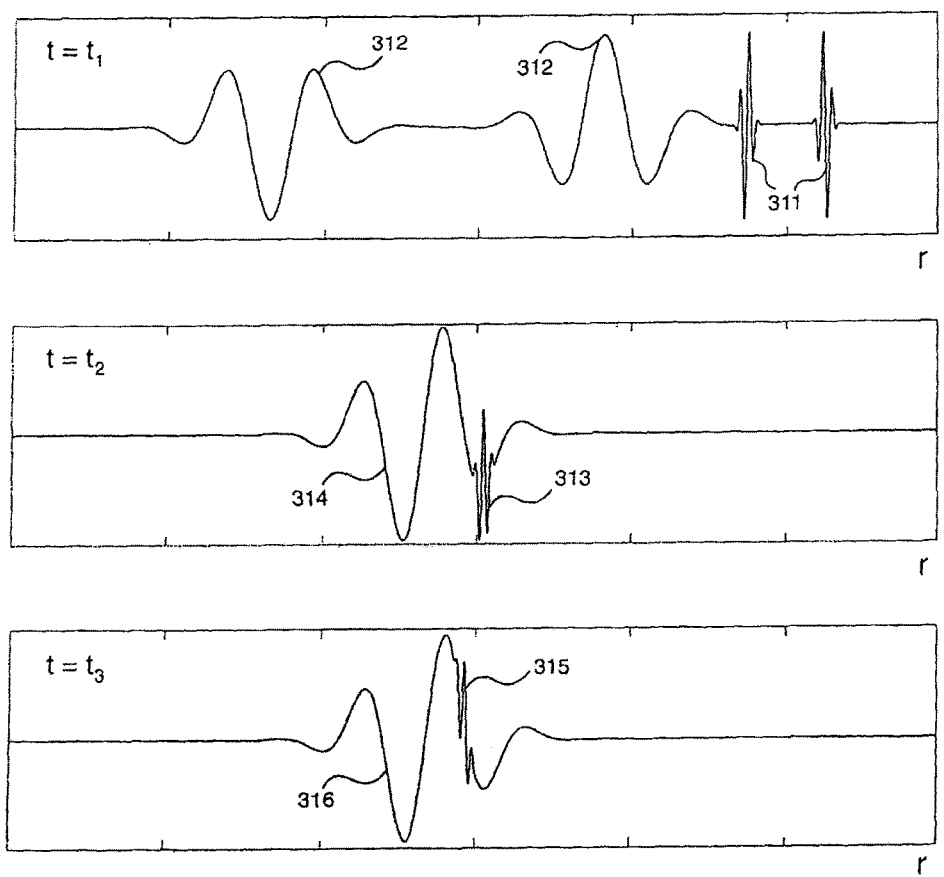
FIG. 3B shows the HF pulse and the LF pulse at times t1, t2, and t3.

As r increases, the delay difference between these pulses reduces, so that the two pulses start to overlap and form a single pulse as illustrated in the two lower panels of FIG. 3B, where 313 and 315 shows the HF pulses and 314 and 316 shows the LF pulses. In the overlap region the edge pulses interfere, both for the LF and HF waves. The interference can be both destructive, that reduces the amplitude, or constructive, that increases the amplitude in the overlap region. We hence get a pulse longer than the transmit pulses on the array surface $P_{lt}(\omega)$ and $P_{ht}(\omega)$ and with a complex internal shape that varies with the depth due to both constructive and destructive interference. In the focal zone, Taylor expansion of the second lines of Eqs. (27, 28) shows that interference between the two pulses produces a pulse which approximates the time derivative ($ik=i\omega/c$) of the transmitted pressure pulses $P_{lt}(\omega)$ and $P_{ht}(\omega)$ at the transducer surface, as discussed above. The reason for the differentiation is the diffraction, which defines the focal region.

As the LF wavelength is longer than the HF wavelength (typically ~5:1-15:1), the focal region where the differentiation of the transmitted pulse is found is typically longer for the LF than the HF pulse.

The pulse centers observe propagation lags from the transmit apertures to 306 for the LF and HF pulses as $$\tau_l(r) = \frac{1}{2c_0}(R_{lo}(r) + R_{li}(r)) \quad (29)$$

$$\tau_h(r) = \frac{1}{2c_0}(R_{ho}(r) + R_{hi}(r))$$

where $\tau_l(r)$ is the propagation lag from the low frequency array to 306 and $\tau_h(r)$ is the propagation lag from the high frequency array to 306. We hence see that for equal LF and HF transmit apertures with the same focus we have $R_{lo}(r)=R_{ho}(r)$ and $R_{li}(r)=R_{hi}(r)$ so that relative propagation lag between the HF and LF pulse centers becomes zero and do not vary with depth, i.e.

$$\Delta\tau(r)=\tau_l(r)-\tau_h(r)=0 \quad (30)$$

The differentiation of the transmitted LF pressure pulse $P_{lt}(\omega)$ towards the focus produces an added time advancement of the LF oscillation of $T_{LF}/4$, where $T_{LF}$ is the temporal period of the LF pulse center frequency. With absorption and/or apodization, the pressure close to the array surface is a replica of the transmitted pulse complex with a propagation delay given by the phase propagation of the LF wave front. We hence see that if we want a specific phase relationship between the LF and the HF pulse in the focal region of the LF beam, we must transmit the HF pulse a time $T_{LF}/4$ earlier in relation to the LF pulse than the relation we want in the LF focal zone, as discussed in relation to FIGS. 2A-D. With adequately wide LF aperture, the LF pulse will in the near field be close to a replica of the LF pulse at the transmit surface, and we can design the LF aperture so that the phase relationship between the HF and LF pulses is close to the same throughout the whole LF near field region.

One can also design the LF transmit aperture so much larger than the HF transmit aperture that in the near field $\tau_h(r)$ is sufficiently less than $\tau_l(r)$ so that by adequate timing between the transmit of the HF and LF pulses, the HF pulse is spatially in front of (i.e. deeper than) the LF pulse with no overlap in a near range. An example of such a situation illustrated in FIG. 3B. For this location of the pulses the near range LF manipulation pressure observed by the HF pulse is efficiently zero.

Figure 3C:
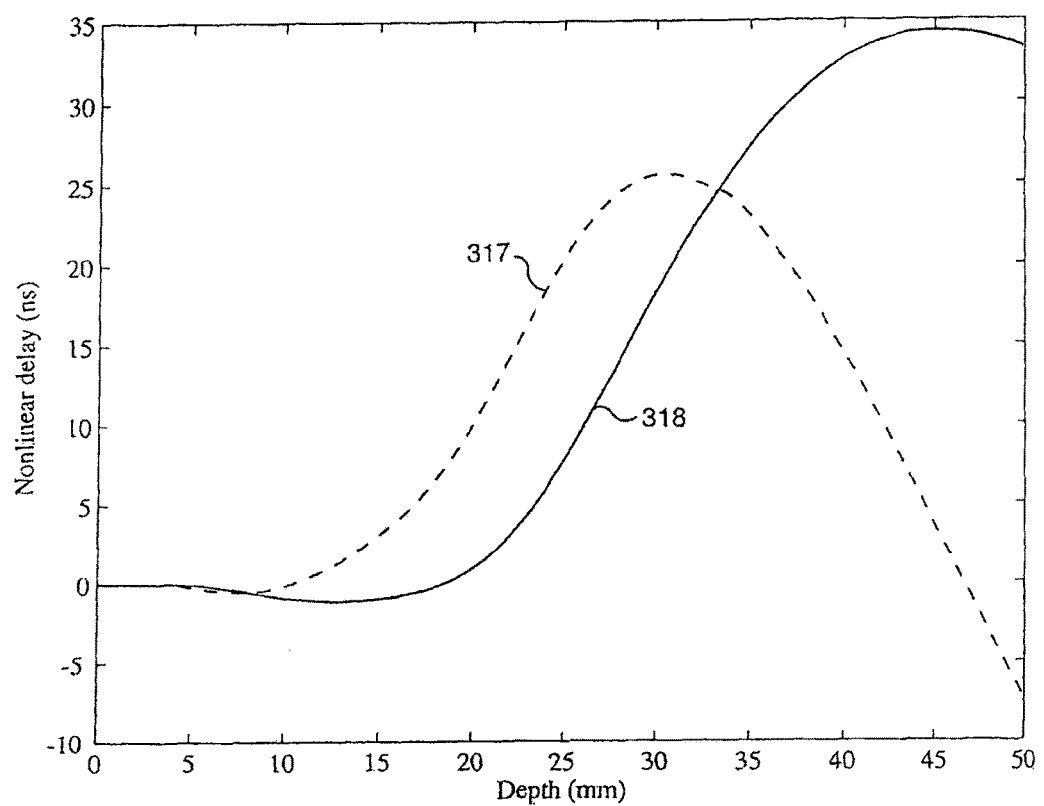
FIG. 3C shows two developments of the HF pulse with depth of the nonlinear propagation delays for two different transmit time lags between the HF and LF pulses.

As r increases, and the time lag $\Delta\tau(r)=\tau_l(r)-\tau_h(r)$ between the pulses is reduced, the HF pulse eventually slides into the LF pulse and starts to observe a nonlinear elasticity manipulation pressure of the LF pulse. For example, at the time point $t_2>t_1$ the pulses have reached the relative position illustrated by 313 for the HF pulse and 314 for the LF pulse. This observed LF manipulation pressure for the HF pulse, produces a nonlinear propagation delay of the HF pulse. Further propagation to a time point $t_3>t_2$ the HF pulse 315 has undergone further sliding relative to the LF pulse 316, where the HF pulse is now on the gradient of the LF pulse that produces a time compression of the HF pulse. An example of two developments with depth of the nonlinear propagation delays are shown in FIG. 3C, where 317 and 318 show the development with depth of the nonlinear propagation delay for two different transmit time lags between the HF and LF pulses. We note that the nonlinear propagation delay for 318 is close to zero up to 20 mm depth, and reaches a maximum of 17 nsec at 45 mm depth, where for 10 MHz $T_0/4=25$ nsec. Due to limited overlap between the HF and LF pulses, the HF pulse form distortion is also low in the near range. After subtraction of the received HF signal for positive and negative LF pulse, this curve provides a strong suppression of pulse reverberation noise where the $1^{st}$ scatterer is up to 20 mm depth, with a gain of the $1^{st}$ scattered signal at 45 mm depth of 2 $\sin(\omega_0\tau)\approx1.75$~4.87 dB. As the uncorrelated electronic noise increase by 3 dB in the subtraction, this gives an increase in signal to electronic noise ratio of 1.87 dB at deep ranges, with strong suppression of pulse reverberation noise relative to imaging at the fundamental frequency. Due to the steering of the near range manipulation, the suppression of the pulse reverberation noise is much stronger than for $2^{nd}$ harmonic imaging, with a far-field sensitivity better than $1^{st}$ harmonic imaging.

The curve 317 has a strong suppression of pulse reverberation noise with the $1^{st}$ scatterer down to 10 mm, where the max gain after subtraction is found at ~30 mm. We hence see that by adequate selection of the HF and LF radiation surfaces and timing of the LF and HF transmit pulses, we can modify the near range of the $1^{st}$ scatterer where strong suppression of the pulse reverberation noise is found, and also the region of large gain of the $1^{st}$ scatterer after the subtraction.

The sliding of the HF and LF pulses with this method do however produce pulse distortion in depth regions where the gradient of the LF pulse along the HF pulse is sufficiently large, for example as illustrated in FIG. 1B and the lower panel of FIG. 3B. For suppression of pulse reverberation noise, for example by subtracting the received HF signals from two pulses with opposite polarity of the LF pulse, the pulse form distortion in the image range do not produce great problems, once it is limited to deep ranges. The most important feature for the suppression of pulse reverberation noise is a large near range region with very low observed LF manipulation pressure and pressure gradient, with a rapid increase of the observed LF manipulation pressure with depth followed by a gradual attenuation of the LF manipulation pressure so that $\omega_0\tau(r)$ rises to the vicinity of $\pi/2$ and stays there, or a rapid increase in observed LF pressure gradient that produces pulse distortion. However, to suppress the linearly scattered signal to obtain the nonlinearly scattered signal, for example according to Eq. (6), the pulse distortion produces problems as discussed above. It can then become important to do pulse distortion correction according to the discussion above, for example through filtering as in Eqs. (18-24), or through frequency mixing and filtering, or through fast time expansion/compression of the received HF signal, or through modification of the transmitted HF pulses to counteract the propagation pulse form distortion, or a combination of these. These considerations give a scheme for optimizing the HF and LF radiation surfaces and their foci together with the signal processing for maximal suppression of pulse reverberation noise and enhancement of nonlinear scattering signals, depending on the application.

Hence, we can arrange the transmit time relation between the HF and LF pulses so that the HF pulse is found at a wanted phase relation to the LF pulse in the focal zone. When the HF pulse is found at pressure extremes of the LF pulse in the focal zone, the nonlinear elasticity manipulation by the LF pulse observed by the HF pulse then mainly produces a nonlinear propagation delay with limited pulse form distortion. This phase relation also maximizes the scattered signal from non-linear scatterers and resonant scatterers where the LF is adequately far from the resonance frequency. When the HF pulse is found near zero crossings of the LF pulse with large observed pressure gradient, one obtains pulse distortion with limited increase in nonlinear propagation delay. However, in the near field the HF pulse will be longer so that parts of the pulse can observe a LF pressure gradient with limited LF pressure, while other parts can observe a limited LF pressure gradient with larger observed LF pressure. This produces a complex pulse distortion of the HF pulse as discussed in relation to Eq. (26).

For a common focal depth F, we get the distances from outer and inner edges of the LF and HF apertures as $$R_{go}(r) = \sqrt{r^2 + 2e_{go}(F-r)} \tag{31}$$

$$e_{go} = F - \sqrt{F^2 - a_{go}^2} \approx \frac{a_{go}^2}{2F}$$

$$g = l, h$$

$$R_{gi}(r) = \sqrt{r^2 + 2e_{gi}(F-r)}$$

$$e_{gi} = F - \sqrt{F^2 - a_{gi}^2} \approx \frac{a_{gi}^2}{2F}$$

$$g = l, h$$

when the last terms under the root sign are relatively small, we can approximate $$R_{go}(r) \approx r + \frac{F-r}{2Fr}a_{go}^2 \tag{32}$$

$$R_{gi}(r) \approx r + \frac{F-r}{2Fr}a_{gi}^2$$

$$g = l, h$$

The r variation of the propagation lag difference between the LF and HF pulses is then found by inserting Eqs. (31, 32) into Eq. (30) which gives $$\Delta\tau(r) = \frac{1}{2c_0}\frac{F-r}{2Fr}(a_{lo}^2 + a_{li}^2 - a_{ho}^2 - a_{hi}^2) \tag{33}$$

Hence, by choosing $$a_{ho}^2 + a_{hi}^2 = a_{lo}^2 + a_{li}^2 \tag{34}$$

we obtain within the approximation zero sliding between the HF and LF pulses in the focal range of the LF pulse, even in the situation where the outer dimension of the LF transmit aperture is larger than the outer dimension of the HF transmit aperture.

A disadvantage with the removed central part of the HF transmit aperture is that the side lobes in the HF transmit beam increase. However, these side lobes are further suppressed by a dynamically focused HF receive aperture. The approximation in Eq. (32) is best around the beam focus, and Eq. (34) do not fully remove phase sliding between the LF and HF pulses at low depths. For other than circular apertures (for example rectangular apertures) one does not have as simple formulas for the axial field as in Eq. (27, 28) but the analysis above provides a guide for a selection of a HF transmit aperture with a removed center, for minimal phase sliding between the LF and the HF pulses with depth. With some two-dimensional arrays one can approximate the radiation apertures with circular apertures where Eq. (34)

can be used as a guide to define radiation apertures with minimal phase sliding between the LF and HF pulses.

One can hence also design the LF and HF transmit apertures so that one gets very little sliding between the HF and LF pulses in an image range, and one can position the HF pulse at the extremes (crest or trough) of the LF pressure pulse so that one gets little pulse form distortion in this image range. Apodization of the LF drive pressure across the array is also useful for best shape of the LF pulse throughout the image range. One hence has a situation where optimal signal processing also involves the design of the LF and HF beams in detail together with pulse distortion correction, delay correction, and potential modification of the HF transmit pulse-form to counteract partially or in full the pulse form distortion that is produced by the propagation.

Figure 4A:
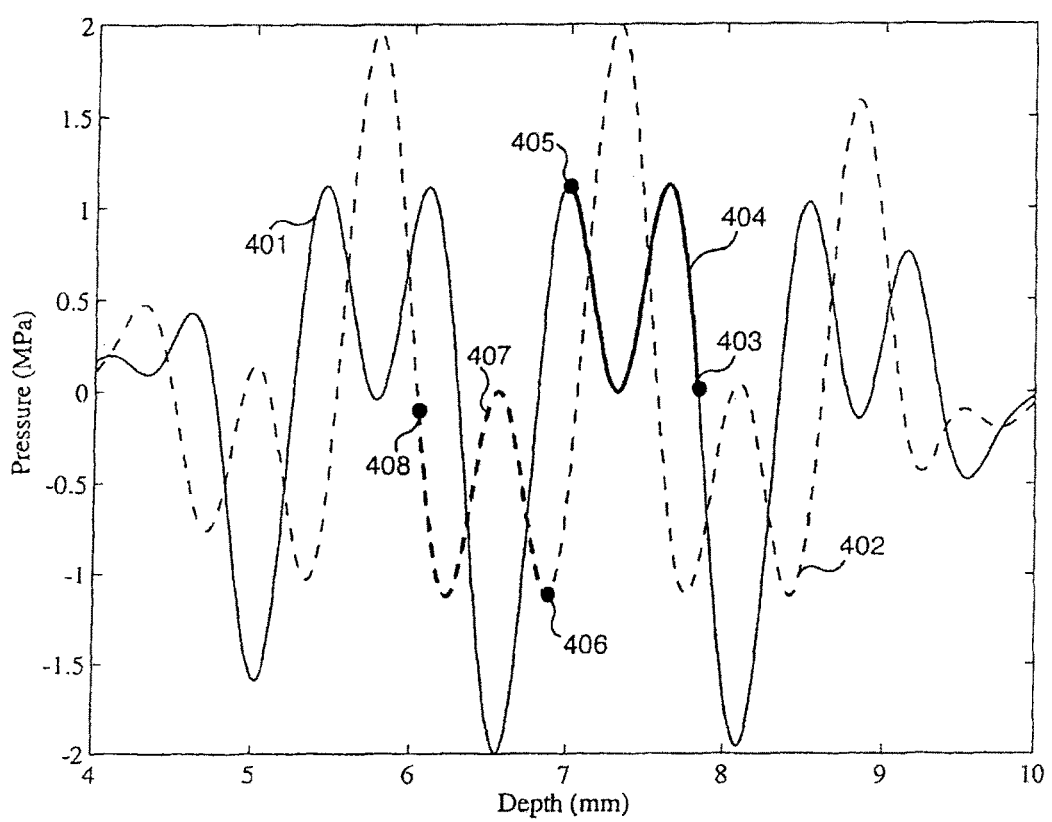
FIGS. 4A and 4B show dual frequency component LF pulses with reduced pulse form distortion.

The variation in pulse distortion between positive and negative polarity of the LF pulse can according to the invention be reduced by using LF pulses with dual peaked spectra, for example by adding a $2^{nd}$ harmonic band to the fundamental LF pulse band, as illustrated in FIG. 4A. This Figure shows a positive polarity LF pulse complex 401 and a negative polarity LF pulse complex 402 which both are obtained by adding a $2^{nd}$ harmonic component to the fundamental LF band. For the positive LF pulse complex the HF pulse slides with propagation along the path 404, for example from a near range position 403 to a far range position 405. For the negative polarity LF pulse 402 one can place the near range position of the HF pulse so that the HF pulse slides with propagation along the path 407, for example from a near range position 406 to a far range position 408. The HF pulse hence slides along similar gradients of the LF pulse for both the positive and negative polarity LF pulse, and similar pulse form distortion is therefore produced for both LF polarities. Other position sliding of the HF pulse along the LF pulse that produce close to the same pulse form distortion for the positive and negative LF pulse, can be obtained with different transmit beam designs, as discussed in relation to FIG. 3A. When the pulse form distortion is the same for the positive and negative LF pulse, it is less important to correct for this distortion both to suppress multiple scattering noise, and to suppress linear scattering to provide the nonlinear scattering component, while correction for nonlinear propagation delay must still be done.

Figure 4B:
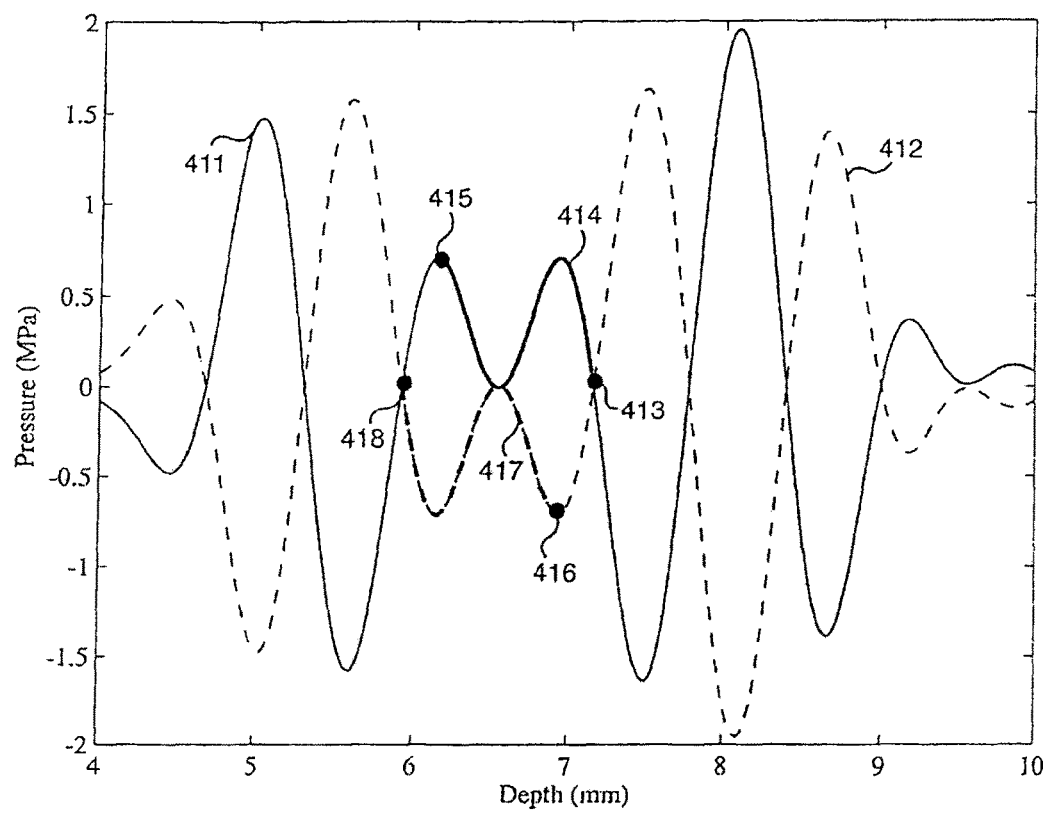

A variation of this type of LF pulse is shown in FIG. 4B where a frequency band around 1.5 times the center frequency of the fundamental band of the LF pulse is added. The positive polarity LF pulse is shown as 411 and the negative polarity LF pulse is shown as 412. For the positive polarity LF pulse the HF pulse slides along the path 414, for example from a near range position 413 until a far range position 415. Similarly, for the negative LF pulse the transmit timing between the HF and LF pulse is modified so that the HF pulse slides along the path 417, for example from a near range position 416 until a far range position 418. The HF pulse also in this case slides along similar gradients of the LF pulse for both the positive and negative polarities of the LF pulse so that similar pulse form distortion for both LF polarities is obtained similarly to the situation exemplified in FIG. 4A.

Figure 1C:
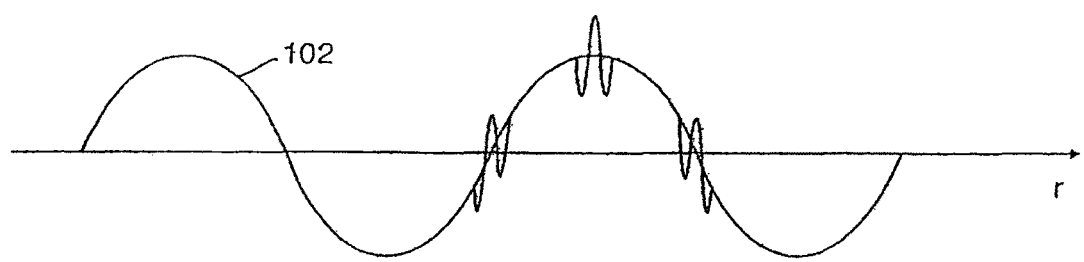

In the same way as the invention devices the use of LF pulses with different degree of complex shape, it is also interesting to use HF pulses of more complex shape as that shown in FIGS. 1A-1C, for example the use of longer, coded pulses, such as Barker, Golay, or chirp coded pulses, with pulse compression in the receiver to regain depth resolution, according to known methods. The longer transmitted pulses allow transmission of higher power under amplitude limitations, for example given by the MI limit, and hence improve signal to electronic noise ratio with improved penetration, without sacrificing image resolution. However, pulse form distortion will be more pronounced with the longer HF pulses as discussed in relation to Eq. (26), and should be corrected for best possible results.

Suppression of the linear scattering to subtract nonlinear scattering is particularly useful to image micro-gas bubbles, for example in medical imaging the ultrasound contrast agent micro-bubbles as described in U.S. patent application Ser. No. 11/189,350 (US Pat Pub 2005/0277835) and U.S. Pat. No. 8,038,616. The micro-bubbles have a resonant scattering introduced by interaction between the co-oscillating fluid mass around the bubble (3 times the bubble volume) and the gas/shell elasticity. This resonant scattering is different from scattering from ordinary soft tissue. For an incident continuous LF wave with angular frequency $\omega_{LF}$ and low-level amplitude $P_{LF}$, the transfer function from the incident LF pressure to the radius oscillation amplitude $\delta a$ is in the linear approximation $$\delta a = -\frac{K_0}{1 - (\omega_{LF}/\omega_0)^2 + i2\zeta(\omega_{LF}/\omega_0)} P_{LF} \qquad (35)$$

where $\omega_0$ is the bubble resonance frequency for the equilibrium bubble radius $a_0$, $\zeta$ is the oscillation losses, $K_0$ is a low frequency, low amplitude radius compliance parameter. Resonance frequencies of commercial micro-bubble contrast agents are 2-4 MHz, but recent analysis [citation 4] indicates that the resonance frequency may be reduced in narrow vessels below 70 µm diameter, and can in capillaries with 10 µm diameter reduce down to 25% of the infinite fluid region resonance frequency (i.e. down to ~0.5-1 MHz).

Two nonlinear effects modifies the oscillation as: 1) The low frequency compliance increases with compression where the bubble compliance is a function of the compression, f.ex. modeled as the function as $K(a_c)$, where $a_c$ is the compressed radius of the bubble so that $K(a_0)=K_0$ in Eq. (35). 2) The small amplitude resonance frequency increases with bubble compression, because the co-oscillating mass is reduced and the bubble stiffness increases. For the same physical reason (opposite effect) the small amplitude resonance frequency reduces with bubble expansion. These two effects introduce nonlinear distortions in the bubble oscillations, and for short pulses with a wide frequency spectrum, the bubble radius oscillation waveform can deviate much from the incident pressure pulse. The nonlinear compression of the bubbles therefore often deviates strongly from the $2^{nd}$ order approximation of Eq. (1). The ratio of the LF to HF pulse frequencies is typically ~1:5-1:15, and typical HF imaging frequencies are from 2.5 MHz and upwards. One can therefore have situations where the center frequencies of either the HF or the LF pulses are close to the bubble resonance frequency. When the low frequency is close to the resonance frequency of ultrasound contrast agent micro-bubbles, one gets a phase lag between the incident LF pressure and the radius oscillation of micro-bubble that gives an interesting effect for the nonlinear scattering.

The linear approximation of the scattered HF pulse amplitude $P_s(r)$ at distance r from the bubble, is for an incident CW HF wave with angular frequency $\omega_{HF}$ and low level amplitude $P_{HF}$ $$P_s(r) = \frac{a_c}{r} \frac{(\omega_{HF}/\omega_c(a_c))^2}{1-(\omega_{HF}/\omega_c(a_c))^2 + i2\zeta(\omega_{HF}/\omega_c(a_c))} P_{HF} \qquad (36)$$

where $\omega_c(a_c)$ is the bubble resonance frequency where the bubble radius is changed to $a_c$ by the LF pulse. The nonlinear detection signal from the bubble, e.g. Eq. (6), is proportional to the difference between the scattered HF pulses for different LF pulses of the at least two pulse complexes. As for the LF bubble oscillation we get a nonlinear effect both from compression variation of the resonance frequency and from nonlinear elasticity of the bubble. However, when the HF frequency is well above the resonance, the HF oscillation amplitude is reduced and the linear approximation in Eq. (36) is good. The scattered HF signal is in the linear approximation $\sim -a_c(P_{LF})P_{HF}$, so that the nonlinear detection signal from the bubble is in this linear approximation $\sim -\Delta a_c(P_{LF})P_{HF} = -[a_c(P_{LF})-a_c(-P_{LF})]P_{HF}$. To get maximal detection signal the HF pulse must be close to the crest or trough of the LF bubble radius, when it hits the bubble. We also note that nonlinearity in the LF bubble oscillation will show directly in the detection signal, where the LF nonlinearity often is much stronger than the $2^{nd}$ order approximation of Eq. (1).

With larger HF amplitudes the detection signal can also have a nonlinear relation to the HF pressure amplitude. When the HF frequency approaches the bubble resonance frequency, the variation of $\omega_c(a_c)$ with the LF pressure introduces a phase shift of the HF pulses from the different pulse complexes with differences in the LF pulse. This further increases the nonlinear detection signal from the bubble and makes a further deviation from the $2^{nd}$ order elasticity approximation in Eq. (6). The HF detection signal hence has increased sensitivity for HF around the bubble resonance frequency.

Figure 5A:
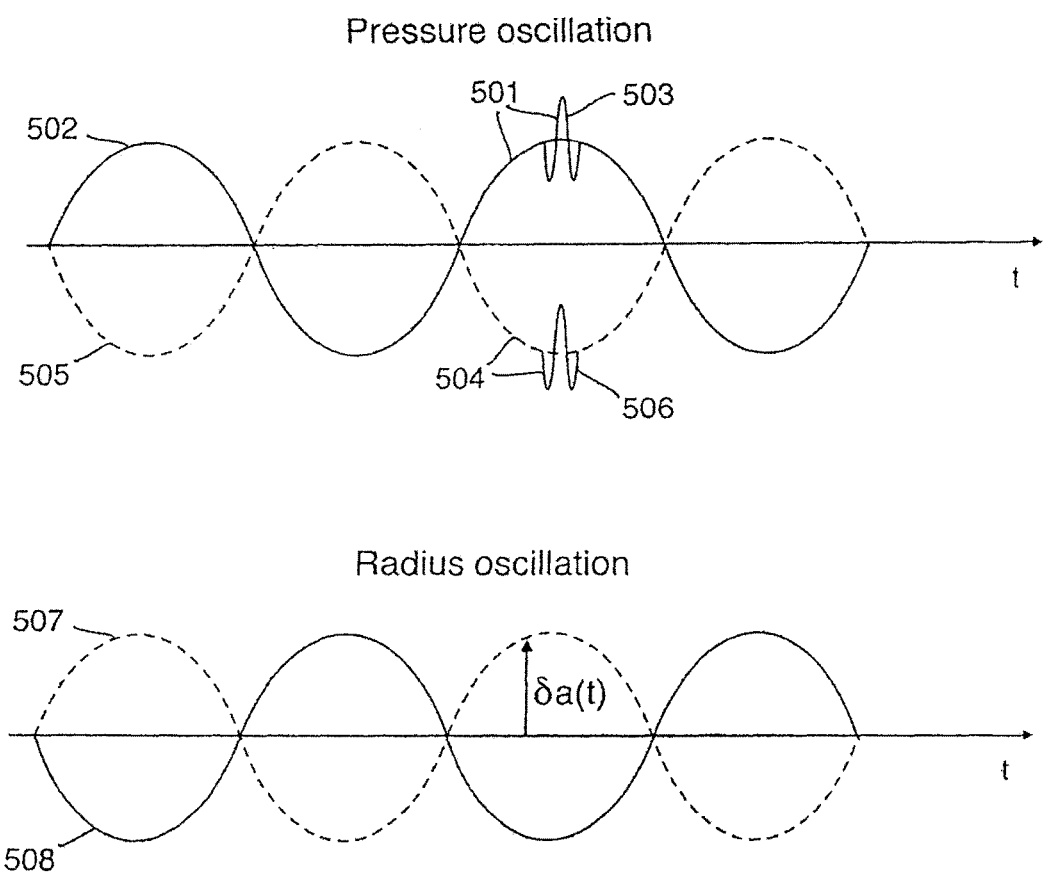
FIGS. 5A-5C show phase relations between HF and LF pulses for best imaging of micro-bubbles when the LF frequency is below and close to the bubble resonance frequency.

For LF well below the bubble resonance frequency, the linear approximation of Eq. (35) gives $\delta a \approx -K(P_{LF})P_{LF}$. This situation is illustrated in FIG. 5A which shows in the upper panel incident HF and LF pulse complexes 501, composed of the LF pulse 502 and the HF pulse 503, and 504 composed of the LF pulse 505 and HF pulse 506. The lower panel shows the radius oscillation $\delta a \approx -KP_{LF}$ produced by the incident LF pulse, where the LF pressure 502 produces the solid radius oscillation curve 508, and the LF pressure 505 produces the dashed radius oscillation curve 507. To produce maximal HF bubble detection signal, the HF pulse must hit the LF radius oscillations at a maximum and a minimum, which is found when the HF pulse is located at the trough (506) and crest (503) of the LF pressure pulses. For LF frequencies well below the bubble resonance frequency, the transmit timing between the HF and LF pulse should therefore be so that the HF pulse is found at the crest and trough of the LF pressure pulse in the interesting image region.

Figure 5B:
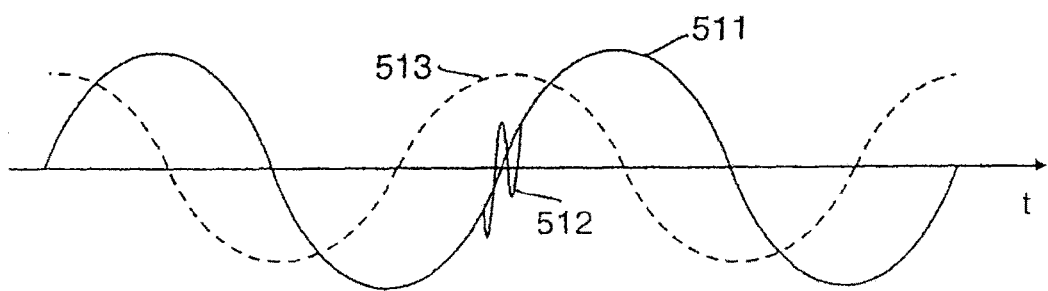

When the LF is at the bubble resonance frequency, we see from Eq. (35) that the bubble radius oscillation is 90 deg phase shifted in relation to the incident LF pulse, as illustrated in FIG. 5B. This Figure shows as 511 an incident LF pressure oscillation, with the resulting LF radius oscillation as 513 (dashed). For the HF pulse to hit the bubble at a maximal radius, the HF pulse must be placed at the negative to positive temporal zero crossing of the LF pulse. Switching the polarity of the incident LF pressure pulse then positions the HF pulse 512 at the positive to negative temporal zero-crossing of the LF pulse, which is then found at the trough of the LF radius oscillation. The HF pulse must then at least for the imaging distance propagate on the maximal positive or negative gradient of the LF pressure, which produces HF pulse form distortion that must be corrected for to maximally suppress the linear scattering from the tissue. As the radius oscillations have a peak at the resonance frequency one then gets the most sensitive detection signal from the bubbles with resonance frequency close to the frequency of the LF pulse. For bubbles with resonance frequency at a distance from the LF, this phase relationship between the HF and LF pulses implies that the HF pulse hits the bubble when the radius passes through the equilibrium value $a_0$ for these bubbles, and the two pulses hence have very small difference in the scattered HF signal from these bubbles with a subsequent very low detection signal.

For LF frequencies well above the bubble resonance frequency we have $\delta a \approx KP_{LF}(\omega_0/\omega_{LF})^2$, which produces low $\Delta a_c(P_{LF})$ and detection signal. To get a good detection signal from the bubble, one hence wants the LF frequency to be from slightly above the bubble resonance frequency and downwards. HF imaging frequencies are generally from ~2.5 MHz up to ~100 MHz and as the LF to HF pulse frequencies have ratios ~1:5-1:100, the LF frequency can get close to the bubble resonance frequency for HF frequencies of ~2.5 MHz and upwards, if we include the 0.5 MHz resonance frequencies of bubbles confined in capillaries. For HF imaging frequencies in the range of 10 MHz and upwards, it is possible to place the LF frequency around typical resonance frequencies of commercially available contrast agent micro-bubbles, and one can then do tuned resonant detection by tuning the LF to any value within the actual resonance of the bubbles.

Selecting a phase relation between the transmitted HF and LF pulses so that the HF pulse is found at the maximal positive or negative gradient of the LF pulse in the actual image range, provides a resonant sensitive detection of the micro-bubbles, with an increased imaging sensitivity for the micro-bubbles with resonance frequency close to the LF. As the LF pulse in the LF focal range is the time derivative of the transmitted LF pulse per the discussion in relation to FIG. 2A and also following Eqs. (27, 28), it means that we should transmit the HF pulse at the crest or trough of the LF pulse to get the phase relationship of FIG. 5B in the focal LF region. The detection signal from bubbles with so high or low resonance frequencies that the phase of the transfer function in Eq. (36) is either $\pi$ or 0 for the LF pulse, will then be highly suppressed. This is different from the resonant enhancement of the detection signal from the bubbles when the HF gets close to the resonance frequency (LF then well below resonance frequency), as in the former case there is a substantial detection signal also when the HF is well above the bubble resonance frequency. Selecting for example LF around ~0.5-1 MHz, which can be done with HF imaging frequencies from ~2.5 MHz and upwards, will provide an increased sensitivity for imaging micro-bubbles confined in capillaries where the bubble resonance is reduced to ~1 MHz, compared to larger vessels and cavities where the bubble resonance is the 3-4 MHz as in an infinite fluid. Mono-disperse micro-bubbles with a sharp resonance frequency in infinite fluid are under development. The reduction in bubble resonance introduced by the confining motion of smaller vessels can then combined with the LF resonant detection be used for selective detection of bubbles in different vessel dimensions. Tissue targeted micro-bubbles are also in development, and the resonance frequency for such bubbles also changes when the bubbles attach to tissue cells. The LF resonant detection of the micro-bubbles can hence be used for enhanced detection of the bubbles that have attached to the cells.

Figure 5C:
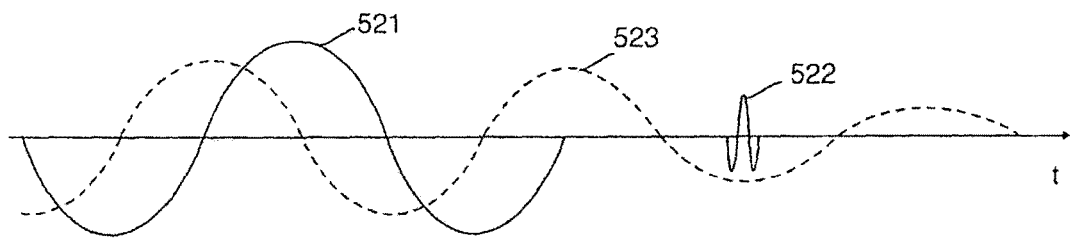

Another method to obtain a resonance sensitive detection of the micro-bubbles is to select the frequency of the LF pulse close to the bubble resonance frequency and transmit the HF pulse with a delay after the LF pulse. When the LF pulse is close to the bubble resonance frequency, the bubble radius oscillation will ring for an interval after the end of the incident LF pulse. The HF pulse delay is selected so that in the actual imaging range the transmitted HF pulse is sufficiently close to the tail of the transmitted LF pulse so that the HF pulse hits the resonating bubble while the radius is still ringing after the LF pulse has passed, preferably at a crest or trough of the radius oscillation, as shown in FIG. 5C. This Figure shows in the time domain by way of example in the actual imaging range the incident LF pressure pulse as 521 with a HF pulse 522 following at the tail of the LF pulse. The radius oscillation excited by the LF pressure is shown as 524 where it is observed that due to the resonance the radius oscillates (rings) for some time period after the end of the exciting LF pressure pulse. With the example phase arrangement between the HF and LF pulses, the HF pulse 522 hits the bubble when it has minimal radius produced by the LF pressure. The HF signal from the tissue is unaffected by the LF pulse. One then typically transmits two or more pulse complexes where the LF pulse varies for transmitted pulse complexes, typically in phase and/or amplitude and/or frequency, and combines the received HF signals from the at least two pulses to suppress the linear HF scattering from the tissue and enhance the HF nonlinear bubble scattering.

Spectral resonance selective imaging of bubbles with a set of different resonance frequencies (diameters) can be done by using resonant detection with different LF frequencies corresponding to the set of resonance frequencies. This has interesting applications for molecular imaging with targeted micro-bubbles where micro-bubbles with different, mono disperse diameters are coated with different antibody ligands. With spectral resonance selective imaging, one can then determine which antibodies has produced attachment to specific tissues, and hence characterize potential disease in the tissue.

The methods described in relation to FIG. 5C are also more generally useful for imaging scatterers that have a memory in a change of scattering parameters produced by the LF pulse 521 that lasts for a period longer than the delay between the LF and the HF pulses, so that the change in the scattering parameters produced by the LF pulse is observed by the HF pulse 522. One example of such memory is a micro-bubble that is subject to a radiation force from an ultrasound pulse. The LF pulse 521 can in this case be used to move the micro-bubble and the displacement can be observed with the subsequent HF pulse 522. In a fluid, this displacement can last for a long time interval, but also when the bubble is confined in a viscoelastic tissue, the displacement produced by the LF pulse 521 can last for a sufficiently long time interval after the passage of the LF pulse that the displacement can be observed by the subsequent HF pulse 522

For some micro-bubbles, the oscillations produced by the LF pulse changes the elasticity of the bubble shell where the change lasts for an interval after the LF pulse has passed, and hence falls into the category of changes of the scattering parameters with a memory. The change in elasticity can for example depend on the molecular structure of the shell. The LF pulse can also change the size of the bubble due to heating of the gas and shell, or due to gas transport across the bubble shell. For such bubbles the LF pulse produces a change in the scattering parameters that also has a memory that can last for enough time to be observed by the subsequent HF pulse 522. Microcalcification in soft tissue with a viscous elasticity can also maintain a memory of a change in the scattering parameters produced by the LF pulse 521 that lasts for enough time to be observed by the subsequent HF pulse 522, and can hence be detected with these methods. The change can be caused by one or both of a nonlinear change in the scattering cross section and a displacement of the micro-calcifications due to the radiation force of the LF pulse. One should note that a resonant bubble ringing after the LF pulse, as described above, also fits the characteristic that the LF pulse changes the scattering parameters with a memory that lasts for enough time after the LF pulse 521 has passed the scatterer to be observed by the HF pulse 522.

The LF pulses do not produce the same change of the scattering parameters for the tissue as for nonlinear scatterers with such memory of the scattering parameters, and one obtains the same received HF signals from non-moving tissues for the two transmitted pulse complexes with differences in the LF pulse. Multiple scattering of the HF pulse produces acoustic noise which reduces image quality. The multiple scattering is dominated by linear scattering, and in a stationary tissue hence has the same properties as the $1^{st}$ order linear scattering from the tissue. Subtracting the received HF signals from the two pulse complexes with differences in the LF pulse will hence suppress the received HF signals from a stationary tissue, and relatively enhance the received HF signals from nonlinear scatterers with such memory in the scattering parameters. One can then for such nonlinear scatters also use a similar time relation between the LF and the HF pulses as shown in FIG. 5C to detect the nonlinear scatterers with a memory of changes in the scattering parameters produced by the LF pulse 521 and observable by the HF pulse 522. The method is particularly useful for detection of micro-bubbles in large organs, like the liver parenchyma, the kidneys, etc., where one for example can use an HF imaging pulse at ~3-4 MHz around the micro-bubble resonance frequency, and the LF pulse for example at ~0.3-1 MHz, which is generally well below the bubble resonance frequency.

For imaging of such nonlinear scatterers in moving tissue, for example the myocardium or the atheroma in an artery wall, the movement of the tissue produces a Doppler modification of the received HF signal from the tissue, that should be corrected for in at least one of the received HF signals, for maximal suppression of the tissue signal.

Current ultrasound image reconstruction techniques take as an assumption that the ultrasound pulse is scattered only once from each scatterer within the beam ($1^{st}$ order scattering). In reality the $1^{st}$ order scattered pulse will be rescattered by a $2^{nd}$ scatterer producing a $2^{nd}$ order scattered wave that is rescattered by a $3^{rd}$ scatterer ($3^{rd}$ order scattered wave), etc. The $1^{st}$ scatterer will always be inside the transmit beam. Forward scattering will follow the incident wave and will not produce disturbing noise, but when the subsequent scattering ($2^{nd}$ scatterer) is at an angle from the forwards direction (most often back scattering) the multiply scattered waves where the last scatterer is inside the receive beam will produce signals with an added delay which appears as acoustic noise. To observe the last scatterer within the receive beam for back scatter imaging, one will only observe odd order scattering, which we generally refer to as pulse reverberation noise. Since the pulse amplitude drops in each scattering, it is mainly the $3^{rd}$ order scattering that is seen as the multiple scattering or pulse reverberation noise in this case.

With negligible multiple scattering, the Doppler modification of the received HF signal from the tissue, described above, is found as a Doppler delay between the received HF signals from different pulse complexes, and can be corrected for by a delay correction related to the Doppler delay for at least one of the signals. The Doppler delay can in this case be obtained through correlation between the received HF signals from different transmitted pulse complexes with the same LF pulse.

Multiple scattering HF signals (pulse reverberation noise) will generally observe a different Doppler delay than the 1st order scattered HF signal that is found in the same fast-time receive interval, because the reverberation Doppler delay is produced by the composite movement of all the scatterers participating in the total multiple scattering chain with a total propagation delay falling within the last time interval. In addition are the reverberation scatterers found at different locations with different movements than the 1st order scatterers that produce received signal components in the same fast-time receive interval. With substantial amount of multiple scattering noise, the tissue signal that should be suppressed is the sum of the 1st and multiple order linearly scattered signal components from the tissue. Because the different Doppler delays of the 1st and multiple order scattered components, tissue movement produces variable interference in the sum of these components that is represented by an average Doppler delay plus a change in the received HF signal speckle represented as a change in the received HF signal complex envelope.

Suppression of $1^{st}$ and multiple order linearly scattered HF signal components in a fast-time interval of the received HF signal from the tissue can then be performed by transmitting at least two pulse complexes, where the LF pulses have different characteristics. The different characteristics may be one or more of center frequency, amplitude, polarity, and/or duration (pulse length), for example. One or more LF pulses can be zero and at least one LF pulse is nonzero. At least one of the received HF signals is:
  a) delay corrected with a correction delay that compensates the average Doppler delay of the composite 1st and multiple scattering HF components in the interval from at least two pulse complexes with differences in the LF pulse, and
  b) speckle corrected with a speckle correction filter compensating the difference in speckle of the composite 1st and multiple scattering HF components in the interval from at least two pulse complexes with differences in the LF pulse, and
  c) the corrected HF receive signal is combined with the other received HF signals, which may include non-corrected received HF signals, to suppress the $1^{st}$ and multiple ordered linearly scattered signals, to enhance the nonlinearly scattered signal from the scatterers with the scattering parameters that have a memory that lasts for at least a time interval after the LF pulse has passed.

To estimate both the average Doppler delay and the speckle correction filter, one can for example transmit 3 pulse complexes in a row along the same beam direction and with the same time interval between the pulses. The LF pulse of the $1^{st}$ and $3^{rd}$ complex can for example be the same, for example zero, and the LF pulse of the $2^{nd}$ complex is different from the two others. We analyze the received HF signal in a short fast time (depth-time) interval $T_i$ around the fast time $t_i$, and the Fourier transform of the HF receive signal in this interval can be modeled as $$S_{01}(\omega) = \Sigma_l(\omega)$$

$$S_p(\omega) = D_n(\omega) X_{np}(\omega) + D_l(\omega)\Sigma_l(\omega)$$

$$S_{02}(\omega) = D_l^2(\omega)\Sigma_l(\omega) \quad (36A)$$

where $S_{01}$ is the received HF signal from the $1^{st}$ pulse complex with zero LF pulse, $S_{02}$ is the received HF signal from the $3^{rd}$ pulse complex, i.e. the $2^{nd}$ with zero LF pulse, and $S_p$ is the received HF signal from the $2^{nd}$ pulse complex, i.e. the one with non-zero LF pulse. $\Sigma_l$ is the received composite linearly scattered HF signal component from both $1^{st}$ and multiple order scattering, that is not manipulated by a LF pulse in a pulse complex as shown in FIG. 5C. $D_l$ is a filter that represents the changes of this received linear component produced by movement of the scatterers between two pulse complexes. The linear phase component of $D_l$ represents the average Doppler delay, while the rest of $D_l$ represents the speckle changes of the linear component due to tissue movement between the pulse complexes. We assume that the change from $1^{st}$ to $2^{nd}$ pulse complex is the same as the change from $2^{nd}$ to $3^{rd}$ pulse complex, so that the change from $1^{st}$ to $3^{rd}$ signal is represented by $D_l^2$ in the last signal of Eq. (36A).

$X_{np}$ is the received signal from the change in $1^{st}$ order scattering from a nonlinear scatterer with a memory of the scattering parameters that is affected by the LF pulse of a pulse complex as in FIG. 5C. The subscript p represents a pulse complex with non-zero LF pulse. $D_n$ is a filter that represents the changes of this received nonlinear component ($1^{st}$ order scattering) produced by movement of the scatterers between two pulse complexes. As for the linear component, the linear phase component of $D_n$ represents the average Doppler delay, while the rest of $D_n$ represents speckle changes of the nonlinear component between the pulse complex. The nonlinear signal component is so weak, that we mainly receive $1^{st}$ order scattering, where $D_n \sim \exp\{i\omega\tau_{1D}\}$, where $\tau_{1D}$ is the Doppler delay for $1^{st}$ order scattering from the nonlinear scatterer between pulse complexes.

One can hence find an estimate of $D_l$ as $$\hat{D}_l(\omega) = \sqrt{\frac{S_{02}(\omega)}{S_{01}(\omega)}} \frac{1}{\sqrt{1 + \mu_N/|S_{01}(\omega)|^2}} \quad (36B)$$

where the last term in the denominator is a Wiener type noise limiting term that prevents excessive large values when the amplitude of $S_{01}$ is low, and $\mu_N$ is a noise limiting parameter. We can then suppress the received HF signal from linear scattering and enhance the received HF signal from nonlinear scatterers with a memory in the scattering parameters using pulse complexes of the form as in FIG. 5C, through a combination of $S_p$ and $S_{01}$.

$$\hat{Y}_n(\omega) = S_p(\omega) - \hat{D}_l(\omega) S_{01}(\omega) \quad (36C)$$
$$= D_n(\omega) X_{np}(\omega) + (D_l(\omega) - \hat{D}_l(\omega))\Sigma_{li}(\omega)$$
$$\approx D_n(\omega) X_{np}(\omega)$$

where for the last approximation we assume that the estimated value is close to $D_l$.

We have here illustrated a general principle of compensation for tissue motion with a specific example sequence of pulse complexes and signal compensation, where the $1^{st}$ and $3^{rd}$ pulse complex has zero LF pulse, and the $2^{nd}$ pulse complex has a non/zero LF pulse. It should be clear that one skilled in the art from the general idea could design other compensation schemes, such as compensating $S_p$ and not $S_{01}$, or an intermediate compensation of both $S_p$ and $S_{01}$, to equalize the noise terms in the signals to be subtracted. One skilled in the art would also be able to design other pulse sequences with matched processing of the received signal based on this example to obtain similar suppression of the signal from tissue, to enhance the signal from nonlinear scatterers with a memory in the scattering parameters, using pulse complexes as in FIG. 5C and processing similar to the description above.

In the near field, the outer edge wave from the LF aperture will arrive at the beam axis with a delay compared to the LF pulse from the more central part of the LF aperture, depending on the apodization and width of the LF aperture. The outer edge wave hence extends the tail of the LF pulse in the near field, and for the HF pulse to be sufficiently close to the LF pulse to observe the bubble radius ringing in the actual imaging range, one can, depending on the arrangement of the HF and LF apertures, have an overlap between the HF and LF pulses in the near field. This overlap introduces a nonlinear propagation delay and potential pulse distortion of the HF pulse. However, for deeper ranges when the outer edge pulse from the LF aperture merges with the central LF pulse (see discussion above) the HF pulse is found behind the LF pulse without any nonlinear modification on the propagation of the HF pulse. Hence, when the HF pulse experiences an overlap with the LF pulse in the near field, one can obtain improved suppression of the linearly scattered signal from tissue by correcting the HF signal for nonlinear pulse distortion and/or propagation delay from the overlap region, or modify the transmitted HF pulses so that combined with the near field pulse distortion one gets the same form of the HF pulses in the imaging region for different variations of the LF pulse.

Figure 14:
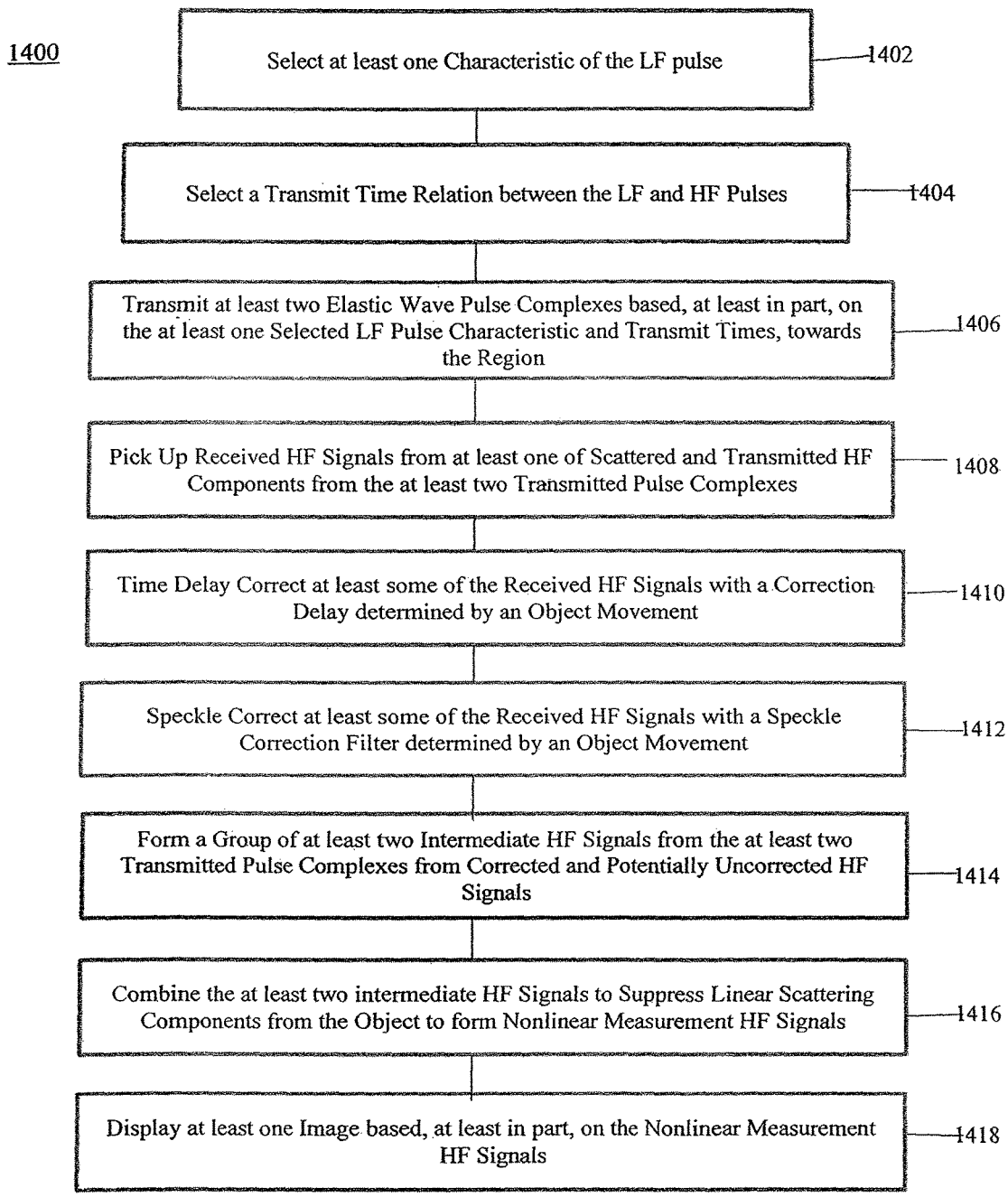
FIG. 14 is a flow chart of an example of a method in accordance with an embodiment of the invention.

FIG. 14 shows a flowchart of an example of a method 1400 for measurement or imaging of elastic wave nonlinear scatterers with a memory of scattering parameters in a region of a scattering object, in accordance with an embodiment of the invention. The method may be implemented by the instruments shown in FIG. 11 and FIG. 12, for example, which are described in detail below. Other instruments having other configurations may be configured to implement embodiments of the invention, as well. In this example, an operator selects an imaging modality to detect nonlinear scatterers of a defined type, for example micro-bubbles with defined properties, so that the LF pulse changes the scattering parameters of the nonlinear scatterers with memory at least for a time interval after the incident LF pulse passes the nonlinear scatterer.

The characteristics of the LF pulses are selected in Step 1402 so that at least some of the LF pulses produces a characteristic change of scattering parameters with memory of nonlinear scatterers for at least a time interval after the LF pulse passes the scatterer. The characteristics of the LF pulses may be selected by the instrument controller 1106 in FIG. 11 or the instrument controller 1207 in FIG. 12, for example.

In Step 1404 the transmit time relation between the LF and HF pulses is selected by the instrument controller 1106, 1207, for example, so that at least in the measurement or imaging range the incident HF pulse propagates spatially behind the incident LF pulse, but sufficiently close to the LF pulse that the HF pulse hits the defined nonlinear scatterers while the effect of the incident LF pulse on its scatterer parameters with memory is observed by the HF pulse.

Figure 11:
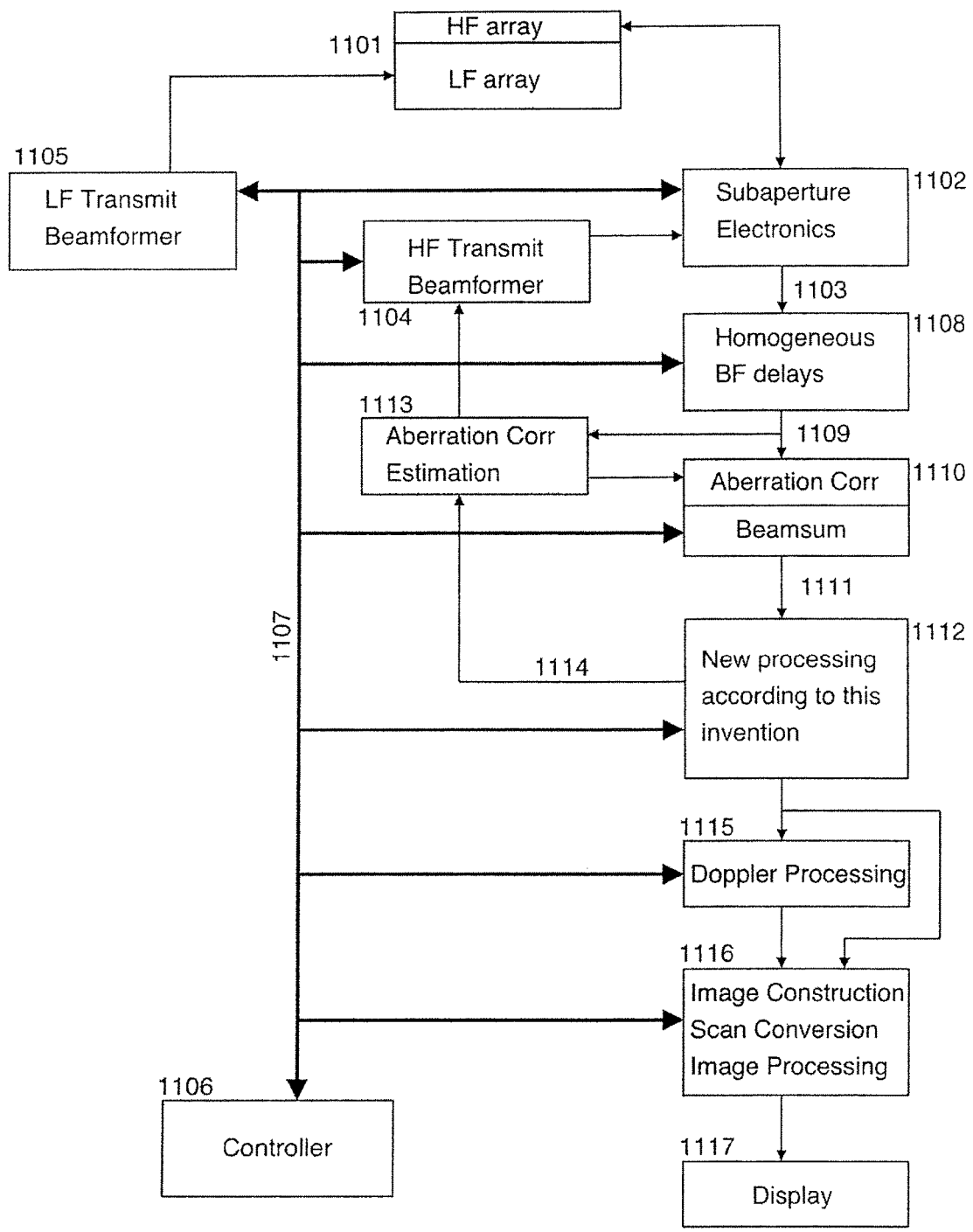
FIG. 11 shows a block diagram of an instrument for backscatter imaging according to the invention.

In Step 1406, at least two elastic wave pulse complexes are transmitted by the acoustic transducer array 1101 under the control of the controller 1106, as described in relation to FIG. 11, for example, towards the region. The pulse complexes are composed of a high frequency (HF) pulse in an HF band and a low frequency (LF) pulse in an LF band. At least the LF pulse varies between at least two transmitted pulse complexes. At least one of the pulse complexes includes a non-zero LF pulse and at least one of the pulse complexes can have a zero LF pulse.

In Step 1408, received HF signals are picked up from at least one of scattered and transmitted HF components from the at least two transmitted pulse complexes, by the acoustic transducer array 1101.

Figure 12:
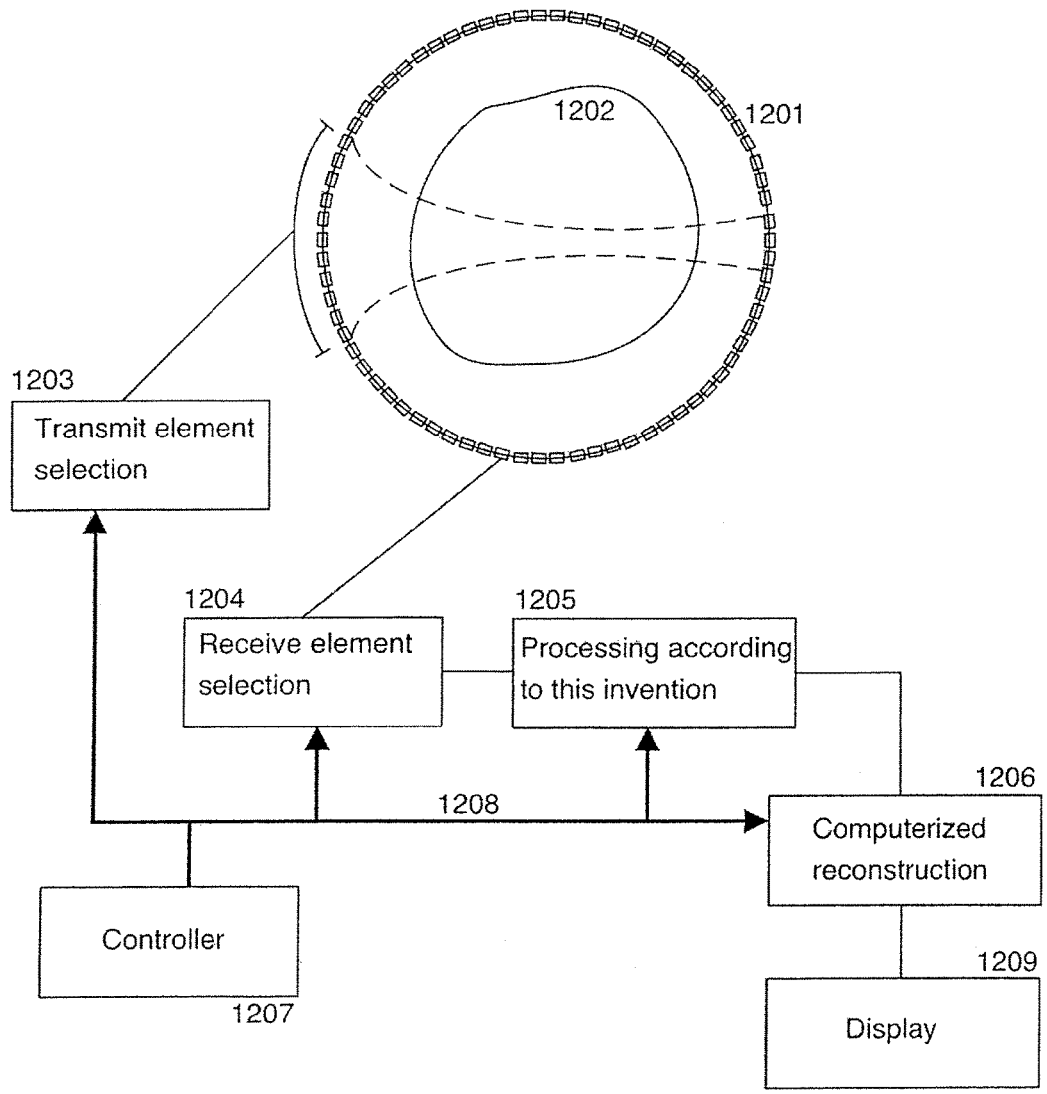
FIG. 12 shows a block diagram of an instrument for computer tomographic image reconstruction from transmitted and scatterers waves.

At least one of the received HF signals is in at least one depth interval corrected by a) time delay correction with a correction delay determined by an object movement, in Step 1410, and/or b) speckle correction with a speckle correction filter determined by an object movement, in Step 1412, by the instrument processing unit 1112, 1205 in FIGS. 11 and 12, for example. The processing units 1112, 1205, may perform both delay correction and speckle correction by implementing the filter of Eq. (36B), as for example, in the $1^{st}$ line of Eq. (36c).

In Step 1414, a group of at least two intermediate HF signals from the at least two transmitted pulse complexes are formed from the corrected and potentially uncorrected HF signals, by the processing unit 1112, 1205. Two such signals are shown as the two signals of the first line of Eq. (36c).

In Step 1416, the at least two intermediate HF signals are combined to suppress linear scattering components from the object to form nonlinear measurement HF signals by the processing unit 1112, 1205. In this example, implementation of Eqs. (36B and 36C) by the instrument processing unit 1112, 1205 also results in the combining of Step 1416.

In Step 1418, at least one image may be reconstructed and displayed on the display 1117, 1209 of FIGS. 11 and 12, respectively, as described herein.

Figure 6:
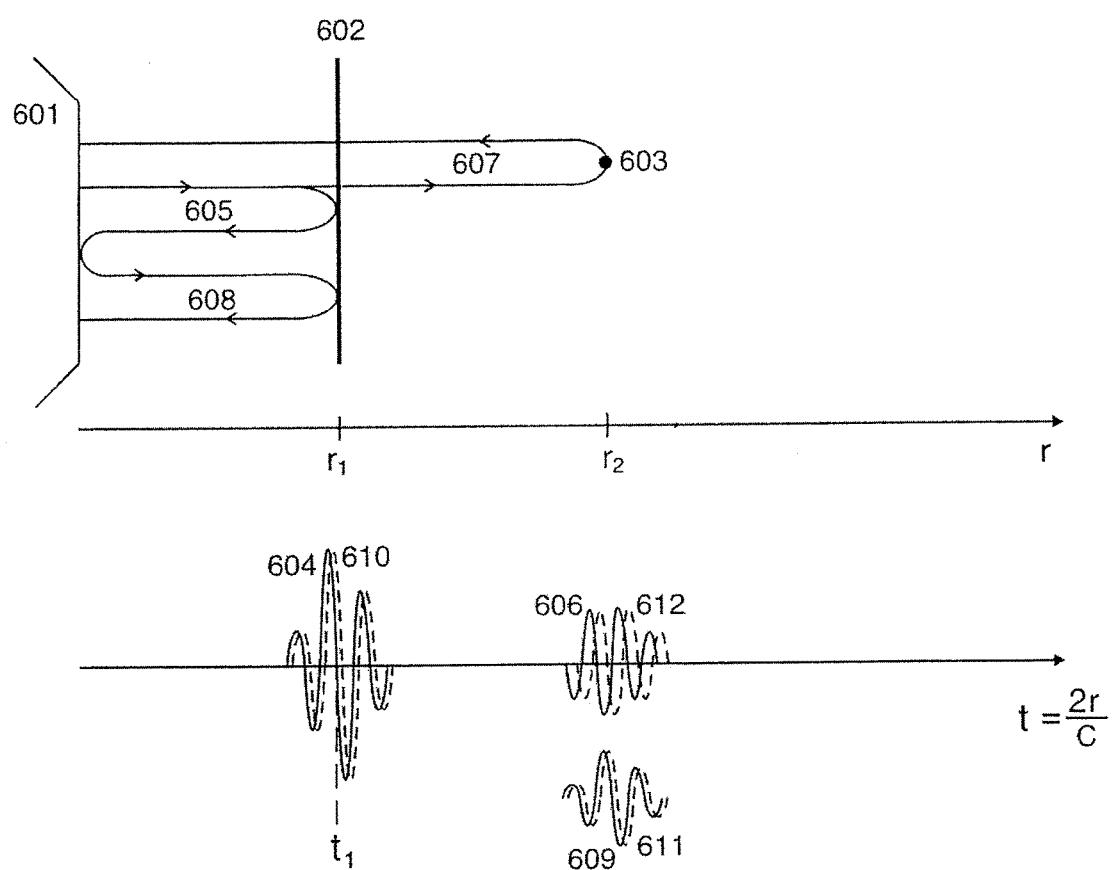
FIG. 6 shows an illustration to how multiple scattering noise is generated and how it can be suppressed with methods according to the invention.

For scatterers that do not have a memory of the scattering parameters as described above, one must device other types of pulse complexes with matched signal processing, to suppress pulse reverberation noise. One can for example according to U.S. patent application Ser. No. 11/189,350 (US Pat Pub 2005/0277835), and U.S. Pat. No. 8,038,616, transmit two pulses with different phase and/or amplitude and/or frequency of the LF pulses, and subtract the received HF signal from the two pulses. An example of a situation that generates strong pulse reverberation noise of this type is shown in FIG. 6 which shows a transducer array 601 and a strong reflecting layer 602 at depth $r_1$ in the object, for example a fat layer, and an ordinary scatterer 603 at $r_2$, about twice the depth of 602 for the example. A transmitted ultrasound pulse observes a $1^{st}$ reflection at 602 to give the received HF pulse 604 following the indicated path 605. The pulse is further partly transmitted at 602 and observes a $1^{st}$ order scattering from 603 to give the received HF pulse 606 along the $1^{st}$ order scattering path indicated as 607. The $1^{st}$ order scattering from 602 observes a $2^{nd}$ reflection from the transducer with a $3^{rd}$ scattering from 602 along the path indicated as 608 to give the received HF pulse 609 at about the same time lag as 606, the $1^{st}$ order scattering from 603, and appears hence as noise in the image.

In the given example there is already obtained some nonlinear propagation delay and potentially also pulse form distortion between the multiply reflected pulses 609/611, which limits the suppression of the multiple scattering noise. The subtraction of the two signals with a delay $2\tau(r)$ from each other produces for band-limited signals a suppression factor $\approx 2 \sin(\omega_0 \tau(r))$ where $\omega_0$ is the HF pulse center frequency and $\tau(r)$ is the nonlinear propagation delay for the positive LF pulse with a nonlinear propagation delay of $-\tau(r)$ for the negative LF pulse. The approximation in the gain factor is because we have neglected any pulse form distortion and we are representing the gain for all frequencies to $\omega_0$ (narrow band approximation).

To maximize the signal after the subtraction of the pulses 612 and 606 from depth $r_2$, we want $\omega_0 \tau(r_2) = \pi/2$, which corresponds to $\tau(r_2) = T_0/4$ where $T_0$ is the period of the HF center frequency.

For strong suppression of the $3^{rd}$ order scattered pulses 609 and 611 we want $\omega_0 \tau(r_1)$ to be small.

When this is not achieved, strong reflectors 602 in the near range can then produce disturbing multiple scattering noise. One method to reduce the nonlinear propagation delay and pulse form distortion at the $1^{st}$ scatterer 602 in a near range, is to remove part of the LF radiation aperture around the center of the HF aperture, for example as illustrated in FIG. 3A. The removed part of the LF radiation aperture reduces the overlap between the LF and the HF beams in the near range indicated as the near range region 305 where the LF field has low amplitude. The nonlinear elasticity manipulation by the LF pulse is therefore very low in the near range region 305.

The difference between the pulses 609 and 611 in nonlinear propagation lag and pulse form distortion, can also be reduced through delay correction and pulse distortion correction as above. For better understanding of these phenomena we refer to the following mathematical model for the $3^{rd}$ order scattered HF signal $$dY_{r3}(\omega; \underline{r}_1, \underline{r}_3) = k^4 U_r(\omega; \underline{r}_1) ik H_r(\underline{r}_3; \omega; \underline{r}_r) \quad (37)$$

$$v(\underline{r}_3)d^3r_3 H_{rev}(\underline{r}_3, \underline{r}_1; \omega) H_t(\underline{r}_1; \omega; \underline{r}_t) v(\underline{r}_1) d^3r_1$$

$$H_{rev}(\underline{r}_3, \underline{r}_1; \omega) = \int_{V_2} d^3r_2 G(\underline{r}_3, \underline{r}_2; \omega) \sigma(\underline{r}_2; \omega) G(\underline{r}_2, \underline{r}_1; \omega)$$

where $\omega$ is the angular frequency and $k = \omega/c$ is the wave number with c as the propagation velocity. $\underline{r}_1$ is the location of the $1^{st}$ volume scatterer $v(\underline{r}_1)d^3r_1$ ($d^3r_1$ is the volume element at $\underline{r}_1$) that is hit by the transmit beam profile focused at $\underline{r}_t$ with spatial frequency response $H_t(\underline{r}_1; \omega; \underline{r}_t)$. We should note that if the phase between the HF and LF pulses varies laterally across the HF near field wave front, for example because the LF and HF beams have different foci, the LF pulse will nonlinearly influence the focusing of the HF transmit beam, as discussed above.

The $1^{st}$ order scattered wave is further scattered at $2^{nd}$ scatterers in $V_2$ and the $2^{nd}$ scattered wave propagates to the location of the $3^{rd}$ volume scatterer $v(\underline{r}_3)d^3r_3$ at $\underline{r}_3$ ($d^3r_3$ is the volume element at $\underline{r}_3$) by the reverberation function $H_{rev}(\underline{r}_3, \underline{r}_1; \omega)$. The variable $\sigma(\underline{r}_2; \omega)$ in $H_{rev}(\underline{r}_3, \underline{r}_1; \omega)$ represents the $2^{nd}$ volume scatterer at $\underline{r}_2$ and $G(\underline{r}_i, \underline{r}_j; \omega)$ is the Green's function for propagation in the linear medium from location $\underline{r}_i$ to $\underline{r}_j$. The nonlinear effect of the LF pulse is negligible after the $1^{st}$ reflection, so that HF pulse propagation from $\underline{r}_1$ via $\underline{r}_2$ to $\underline{r}_3$ is linear and can be described by the Green's function. The $3^{rd}$ order scattered wave is then picked up by the receive transducer array with a spatial sensitivity given by the receive beam $H_r(\underline{r}_3; \omega; \underline{r}_r)$ focused at $\underline{r}_r$, and $U_r(\omega; \underline{r}_1)$ is the Fourier transform of the received pulse when the $1^{st}$ scatterer is at $\underline{r}_1$. The total signal is found by summing over all the $1^{st}$ and $3^{rd}$ scatterers, i.e. integration over $d^3r_1$ and $d^3r_3$.

The transducer array itself is in medicine often the strongest $2^{nd}$ scatterer, and can be modeled as $$\sigma(\underline{r}_2; \omega) = ik 2R(\underline{r}_2; \omega) \delta(S_R(\underline{r}_2)) \quad (38)$$

where $R(\underline{r}_2; \omega)$ is the reflection coefficient of the reflecting transducer surface $S_R$ defined by $S_R(\underline{r}_2) = 0$, and $\delta(\ )$ is the delta function. Body wall fat layers can also have so strong reflection that $3^{rd}$ order scattering becomes visible. $\sigma(\underline{r}_2; \omega)$ can then be modeled by a volume scattering distribution as $$\sigma(\underline{r}_2; \omega) = -k^2 \nu(\underline{r}_2) \quad (39)$$

In technical applications one often have strongly reflecting layers at a distance from the transducer, for example a metal layer, which can be modeled as Eq. (38) where $S_R(\underline{r}_2) = 0$ now defines the layer surface. Strong volume scatterers are then modeled as in Eq. (39).

The LF pulse changes the propagation velocity of the transmitted HF pulse up to $\underline{r}_1$, given by the average LF pressure along the HF pulse, and changes the frequency content of the HF pulse due to the pulse distortion produced by gradients of the LF pressure along the HF pulse. The effect of the LF pulse will vary somewhat across the HF transmit beam, but as the receive beam is narrow, the effect can be included in received pulse Fourier transform $U_r(\omega; \underline{r}_1)$, both as a change in the linear phase produced by the nonlinear propagation delay (propagation velocity) and a change of the frequency content produced by the pulse distortion. By this we can leave the spatial frequency response of the HF transmit beam $H_t(\underline{r}_1; \omega; \underline{r}_t)$ unchanged by the co-propagating LF pulse. After the $1^{st}$ scattering at $\underline{r}_1$ the LF pulse amplitude drops so much that one can neglect nonlinear changes of the HF pulse after this point, and $U_r(\omega; \underline{r}_1)$ therefore only depends on the location $\underline{r}_1$ of the $1^{st}$ scatterer. The Green's function is reciprocal, i.e. $G(\underline{r}_j, \underline{r}_i; \omega) = G(\underline{r}_i, \underline{r}_j; \omega)$, which implies that $H_{rev}(\underline{r}_3, \underline{r}_1; \omega) = H_{rev}(\underline{r}_1, \underline{r}_3; \omega)$. When the transmit and the receive beams are the same, i.e. $H_r(\underline{r}_3; \omega; \underline{r}_r) = H_t(\underline{r}_1; \omega; \underline{r}_t)$, the $3^{rd}$ order scattered signal will be the same when the $1^{st}$ and $3^{rd}$ scatterer changes place for $U_r(\omega; \underline{r}_1) = U_r(\omega; \underline{r}_3)$. This is found for zero LF pulse where $U_r(\omega; \underline{r}_1) = U_r(\omega) = U_r(\omega; \underline{r}_3)$, while this equality do not hold for $\underline{r}_3 \neq \underline{r}_1$ when the LF pulse produces nonlinear propagation delay and/or pulse distortion.

Higher order pulse reverberation noise can be described by adding further orders of scattering, where odd orders of scattering will contribute to the pulse reverberation noise and will have the same basic properties as described for the $3^{rd}$ order scattering. Integration over the volume of scatterers and inverse Fourier transform then give us the following model for the received HF signal with a linearly and nonlinearly scattered component plus pulse reverberation noise as $$s_k(t) = \int dt_0 v_{k1}(t - t_0; t_0) x_1(t_0) + \quad (40)$$

$$\int dt_0 v_{k2}(t - t_0; t_0) x_2(t_0) + \int_0^t dt_1 \int dt_0 v_k^r(t - t_0; t_1) x_r(t_0; t_1)$$

$$k = 1, \ldots, K$$

where k denotes the pulse number coordinate with variations in the transmitted HF/LF pulse complexes, the $1^{st}$ and $2^{nd}$ terms represents the linear and nonlinear $1^{st}$ order scattering, where $v_{k1}(t-t_0;t_0)$ represents both the nonlinear propagation delay and pulse form distortion for the linearly scattered signal $x_1(t)$. Similarly represents $v_{k2}(t-t_0;t_0)$ both the nonlinear propagation delay and pulse form distortion for the nonlinearly scattered signal, but can in addition represent nonlinear frequency changes in the nonlinearly scattered signal from f.ex. micro-bubbles with different LF and HF pressures so that the nonlinear scattering can be represented by a single signal $x_2(t)$. The last term represents the pulse reverberation noise at fast time t. $x_r(t;t_1)dt_1$ represents the pulse reverberation noise at t for zero LF pulse where the $1^{st}$ scatterers are in the interval $(t_1, t_1+dt_1)$, and $v_k^r(t-t_0;t_1)$ represents the nonlinear propagation delay and pulse form distortion of the received pulse for non-zero LF pulse where the $1^{st}$ scatterer is at fast time location $t_1$. For simplicity of notation we have let the filter impulse responses represent both the nonlinear propagation delay and the pulse form distortion. With phase relations between the HF and LF pulses so that pulse form distortions is negligible $v_{k1}$, $v_{k2}$, $v_k^r$ then represents mainly nonlinear propagation delays. In practical corrections one would separate the correction for the nonlinear propagation delay (as a direct delay correction) and pulse form distortions to reduce the required length of the impulse responses for efficient calculation as discussed in relation to Eq. (24). The filter responses also include variations in the received HF signals from variations in the forward propagating HF pulses, for example due to nonlinear propagation and also variations in transmitted amplitude, polarity, frequency, and form (for example variations of a coded pulse).

In many situations the nonlinear scattering is much weaker than the linear scattering, and the $2^{nd}$ term in Eqs. (40) can be neglected, reducing the number of unknown to be estimated. It can also be interesting in some cases to introduce more information carrying signals, for example separate the second term into a nonlinear term from soft tissue with second order nonlinear elasticity and a term from resonant micro-bubbles, or into terms representing micro-bubbles with different resonance frequencies in view of the discussion in relation to FIG. 5B and FIG. 5C.

For zero transmitted LF pulse for the first measurement signal we have $$v_{11}(t-t_0;t_0) = v_1^r(t-t_0;t_1) = \delta(t-t_0) \quad (41)$$
$$v_{12}(t-t_0;t_0) = 0$$
$$s_1(t) = x_1(t) + \int_0^t dt_1 x_r(t;t_1)$$

The last term hence represents the pulse reverberation noise at fast time t when there is no transmitted LF pulse. Generally $v_k^r(t-t_0;t_1)$ has a slow variation with $t_1$, and we can divide the fast time interval into a set of N sub-intervals $T_l$ and approximate the integral over $t_1$ with a sum as $$s_k(t) = \int dt_0 v_{k1}(t-t_0;t_0) x_1(t_0) + \quad (42)$$
$$\int dt_0 v_{k2}(t-t_0;t_0) x_2(t_0) + \sum_{l=3}^{L} \int dt_0 v_k^r(t-t_0;t_l) \int_{T_l} dt_1 x_r(t_0;t_1)$$

which gives the following set of linear operator equations with a finite set of unknowns $$s_k(t) = V_{k1}\{x_1(t)\} + V_{k2}\{x_2(t)\} + \sum_{l=3}^{L} V_{kl}\{x_l(t)\} \quad (43)$$
$$x_l(t) = \int_{T_l} dt_l x_r(t;t_1)$$
$$V_{kl}\{x_l(t)\} = \int dt_1 v_k^r(t-t_0;t_l) x_l(t_0)$$
$$l = 3, K, L$$

The operators $V_{kl}$ are linear operators and Eq. (43) can then be viewed as a set of algebraic linear operator equations, which can be solved by similar methods as for a set of ordinary linear algebraic equations. We introduce the vector and operator matrix notations $$\underline{s} = V\{\underline{x}\}$$

where $$\underline{s}^T(t) = \{s_1(t), s_2(t), \ldots, s_K(t)\} \quad (44)$$
$$\underline{x}^T(t) = \{x_1(t), x_2(t), \ldots, x_L(t)\}$$
$$V\{\} = \begin{pmatrix} V_{11}\{\} & V_{12}\{\} & \ldots & V_{1L}\{\} \\ V_{21}\{\} & V_{22}\{\} & \ldots & V_{2L}\{\} \\ \vdots & & \ddots & \vdots \\ V_{K1}\{\} & V_{K2}\{\} & \ldots & V_{KL}\{\} \end{pmatrix}$$

where we have introduced arbitrary dimension K, L of the equation set. When K=L, the set of equations can for example be solved with the determinant method for matrix inversion $$\underline{x} = V^{-1}\{\underline{s}\}$$

where $V^{-1}$ can be calculated as $$V^{-1} = [\text{Det}V]^{-1}[K_{kl}]^T = [\text{Dev}V]^{-1}[K_{lk}] \quad (45)$$
$$K_{kl} = (-1)^{k+l} M_{kl}$$
$$M_{kl}\{\} = \text{Det} \begin{pmatrix} V_{11}\{\} & \ldots & \vdots & \ldots & V_{1L}\{\} \\ \vdots & & \vdots & & \vdots \\ \ldots & \ldots & V_{kl}\{\} & \ldots & \ldots \\ \vdots & & \vdots & & \vdots \\ V_{K1}\{\} & \ldots & \vdots & \ldots & V_{KL}\{\} \end{pmatrix}$$

$K_{kl}$ is the cofactor matrix where for calculation of $M_{kl}$ the k-th row and l-th column is removed from the operator matrix V. DetV is the operator determinant of the operator matrix V. The determinants are calculated in the same way as for a linear algebraic matrix. In the operator calculations the multiplication of the elements means successive application of the element operators. DetV is hence an operator where $[\text{DetV}]^{-1}$ means the inverse of this operator, for example calculated through the Wiener type formula of the Fourier transform as in Eqs. (21-26). Inversion of the operator is hence a correction both for nonlinear propagation delay and pulse form distortion. One should also note that operator inversion could be composed of a frequency mixing, fast time filter correction, fast time compression/expansion, and delay correction, per the discussion following Eq. (26). In case one with the frequency mixing also reduces the bandwidth with fast time filtering, one would solve a band-reduced version of $x_1(t)$ and $x_2(t)$ with reduced range resolution, as discussed following Eq. (26). This could be preferred because of the improved suppression of reverberation noise and extraction of nonlinear scattering signals.

In this particular situation we have M=2 information carrying signals, the $1^{st}$ order linearly scattered signal $x_1(t)$ and the nonlinearly scattered signal $x_n(t)$, so that the total number of unknowns is L=M+N, where N is the number of noise terms. We want to eliminate the noise terms (l=3, ..., L) to obtain estimates of the $1^{st}$ order linearly and nonlinearly scattered signals, $x_1(t)$ and $x_2(t)$. This can be obtained through the following estimates $$x_l(t) = x_1(t) = [\text{Det} V]^{-1} [K_{k1}\{s_k(t)\}]$$

$$x_n(t) = x_2(t) = [\text{Det} V]^{-1} [K_{k2}\{s_k(t)\}] \quad (46)$$

where summation is done over the equal indexes k. Again we note that the algebraic multiplication of the operators in the equations above means successive application of the operators to the signals. We note that if we remove $[\text{Det} V]^{-1}$ we will get a filtered version of $x_1(t)$ and $x_2(t)$. Per the discussion following Eq. (40) the nonlinear term can often be neglected (M=1), and also separated into more terms (M>2).

It is also interesting to have more measurements than unknowns, i.e. K>L, where one can find the set of unknowns $x_l(t)$ so that the model $\underline{s} = V\{\underline{x}\}$ gives the best approximation to the measured signals $\underline{s}(t)$ in a defined norm, for example in the least square norm. The least square solution to this problem is given by the pseudo inverse of V $$\underline{x}(t) = (V^T V)^{-1} V^T \{\underline{s}\} \quad (47)$$

Figure 7:
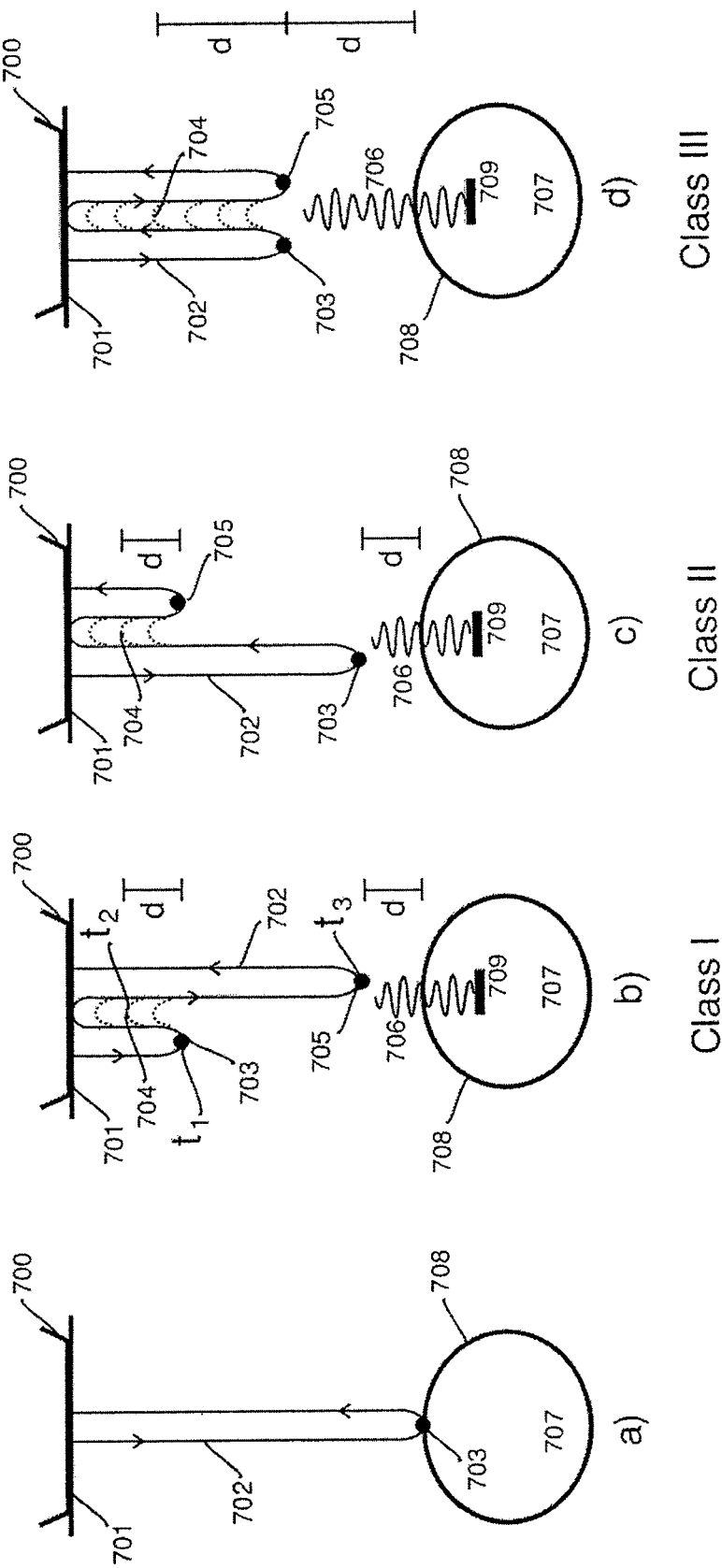
FIG. 7 shows conceptual illustrations to pulse reverberation noise of Class I-III.

For more detailed analysis of the reverberation noise we refer to FIG. 7 which schematically illustrates 3 different classes of pulse reverberation noise, Class I-III, b)-d), together with the propagation situation for $1^{st}$ order scattering in a). The Figures all show an ultrasound transducer array 700 with a front transmit/receive and reflecting surface 701. The pulse propagation path and direction is indicated with the lines and arrows 702, where the $1^{st}$ scatterer is indicated by the dot 703, and the $3^{rd}$ scatterer is indicated by the dot 705. Positions of multiple $2^{nd}$ scatterers are indicated as 704. Due to the multiple positions of the $2^{nd}$ scatterers the two $1^{st}$ and $3^{rd}$ scatterers 703 and 705 then generates a tail of pulse reverberation noise 706 following the deepest of the $1^{st}$ and $3^{rd}$ scatterers. 707 shows for illustrative example a low echogenic region, for example in medicine the cross section of a vessel or a cyst, with a scattering surface 708, that we want to image with high suppression of pulse reverberation noise. The object has so low internal scattering that the pulse reverberation noise 706 generated in the different classes produces disturbances in the definition of the scattering surface 708.

To obtain visible, disturbing reverberation noise in the image, the $1^{st}$-$3^{rd}$ scatterers in Eq. (37) must be of a certain strength. In medical applications this is often found by fat layers in the body wall, while in technical applications one can encounter many different structures, depending on the application. In medical applications, the strongest $2^{nd}$ scatterer is often the ultrasound transducer array surface itself, as this can have a reflection coefficient that is ~10 dB or more higher than the reflection coefficient from other soft tissue structures. The pulse reverberation noise that involves the transducer surface as the $2^{nd}$ scatterer, is therefore particularly strong indicated by 709.

Further description of the Classes is:

Class I (b) is the situation where the 1st scatterer (703) is closest to the transducer at fast time depth of t1. The 2nd scatterer (704) is at the fast time t2. The distance between the 3rd scatterer 705 and the noise point, which in the Figure coincides with the object surface 706, is the same as the distance d=t1-t2 between the 1st and the 2nd scatterers. With varying positions of the 2nd scatterer 704, we get a tail 706 of pulse reverberation noise. When the transducer surface 701 is the strongest 2nd scatterer, we get particularly strong noise at 709. As the 1st scatterer is close to the transducer for Class I, the nonlinear propagation lag and pulse distortion at the 1st scatterer is here low, and especially with a LF aperture that lacks the central part as described in relation to FIG. 3A the nonlinear propagation lag and pulse distortion can often be neglected at the 1st scatterer. Subtraction of the received signals from two pulse complexes with opposite polarity of the LF pulse will then produce a strong suppression of the pulse reverberation noise of Class I. When the central part of the LF transmit aperture is not missing, the suppression can however improve by a correction for pulse form distortion lag and/or the nonlinear propagation at the 1st scatterer, as discussed below.

Class II (c) The $1^{st}$ scatterer 703 has moved so deep that the $3^{rd}$ (705) scatterer is closer to the transducer than the $1^{st}$ scatterer. When strong scatterers are found at 703 and 705 for Class I, we also have Class II noise with $1^{st}$ and $3^{rd}$ scatterers interchanged. Class II hence shows the inverse propagation 702 of Class I, and the two classes of noise therefore always coexist. The reasoning for the tail of pulse reverberation noise 706 is the same as that for Class I, where a strongly reflecting transducer surface gives the noise 709. With the same transmit and receive beams (focus and aperture), Eq. (37) shows that the pulse reverberation noise with zero LF pulse is the same for Class I and Class II. However, with nonzero LF pulse, the received HF signals from these two classes are different, because one gets higher nonlinear propagation lag and pulse distortion for Class II than for Class I because the $1^{st}$ scatterer is deeper for Class II. However, the two noise classes can be summed to one class which reduces the number of unknowns in the equation as in Eqs. (69-75).

Class III (d) This Class is found as a merger of Class I and Class II where the $1^{st}$ scatterer (703) has moved so deep that the $1^{st}$ and $3^{rd}$ (705) scatterers have similar depths or are the same, so that the nonlinear propagation lag and pulse distortions are approximately the same when the $1^{st}$ and $3^{rd}$ scatterers are interchanged. This noise hence includes a factor 2 in the amplitude, as a sum of the $1^{st}$ and $3^{rd}$ scatterer being 703 and 705 and the reverse path where the $1^{st}$ and $3^{rd}$ scatterers are 705 and 703. This situation is often found with strongly scattering layers, as a metal layer in industrial applications and a fat layer or bone structure in medical applications. The reasoning for the tail of pulse reverberation noise 706 is the same as that for Class I/II, where a strongly reflecting transducer surface gives the noise 709.

With defined regions of the $1^{st}$ and $3^{rd}$ scatterers for Class I-II noise, Eq. (43) can be approximated to $$s_1(t) = V_{11}\{x_1(t)\} + V_{12}\{x_2(t)\} + V_{13}\{x_3(t)\} + V_{14}\{x_4(t)\} + V_{15}\{x_5(t)\}$$

$$s_2(t) = V_{21}\{x_1(t)\} + V_{22}\{x_2(t)\} + V_{23}\{x_3(t)\} + V_{24}\{x_4(t)\} + V_{25}\{x_5(t)\}$$

$$s_3(t) = V_{31}\{x_1(t)\} + V_{32}\{x_2(t)\} + V_{33}\{x_3(t)\} + V_{34}\{x_4(t)\} + V_{35}\{x_5(t)\}$$

$$s_4(t) = V_{41}\{x_1(t)\} + V_{42}\{x_2(t)\} + V_{43}\{x_3(t)\} + V_{44}\{x_4(t)\} + V_{45}\{x_5(t)\}$$

$$s_5(t) = V_{51}\{x_1(t)\} + V_{52}\{x_2(t)\} + V_{53}\{x_3(t)\} + V_{54}\{x_4(t)\} + V_{55}\{x_5(t)\} \quad (48)$$

where $\underline{x}^T(t) = \{x_1(t), x_2(t), x_3(t), x_4(t), x_5(t)\}$ is the initial signals where $x_1(t)$ is the $1^{st}$ order linearly scattered signal for zero LF pulse, $x_2(t)$ is the nonlinearly scattered signal for a normalized HF and LF pulse and $x_3(t)$, $x_4(t)$, $x_5(t)$ are the pulse reverberation noise of Class I, III, and II for zero LF pulse. One example is a fixed HF pulse with a relative variation of the LF transmit amplitudes between the 5 pulse complexes relative to the normalized LF pulse by $p_1$-$p_5$. Typically we can use $p_1=0$, $p_5=-p_2$, and $p_4=-p_3=-p_2/2$. For the $2^{nd}$ order elasticity where the approximation of the nonlinear scattering of Eq. (5) is adequate we can set $V_{k2} = p_k V_{k1}$, as the operators represent the nonlinear propagation delay and pulse distortion of the forward propagating pulse. However, with heavily resonant HF scattering as from micro gas-bubbles, the LF pressure can also affect the scattered waveform so that $V_{k2} \neq p_k V_{k1}$. However, making the assumption of $V_{k2} = p_k V_{k1}$ can help us to solve the above equations as the nonlinearly scattered signal is generally much weaker than the linearly scattered signal. In the same way as in Eqs. (40-44), one can let $V_{k1}$ include variations in the forward propagating HF pulse, for example due to nonlinear propagation and also variations in transmitted amplitude, polarity, frequency, focusing, and form (for example variations of a coded pulse).

For the practical calculation we can also solve the set of equations in Eqs. (43-48) through a successive operator Gauss elimination similar to the Gauss elimination for linear algebraic equations. We can typically start by eliminating the noise signals in a sequence, for example starting with elimination of Class II noise, $x_5(t)$, as $$a) \quad z_1(t) = V_{15}^{-1}\{s_1(t)\} - V_{25}^{-1}\{s_2(t)\} \quad (49)$$
$$= V_{15}^{-1} V_{11}\{x_1(t)\} - V_{25}^{-1} V_{21}\{x_1(t)\} +$$
$$V_{15}^{-1} V_{12}\{x_2(t)\} - V_{25}^{-1} V_{22}\{x_2(t)\} +$$
$$V_{15}^{-1} V_{13}\{x_3(t)\} - V_{25}^{-1} V_{23}\{x_3(t)\} +$$
$$V_{15}^{-1} V_{14}\{x_4(t)\} - V_{25}^{-1} V_{24}\{x_4(t)\}$$
$$= A_{11}\{x_1(t)\} + A_{12}\{x_2(t)\} + A_{13}\{x_3(t)\} + A_{14}\{x_4(t)\}$$

$$b) \quad z_2(t) = V_{15}^{-1}\{s_1(t)\} - V_{35}^{-1}\{s_3(t)\}$$
$$= V_{15}^{-1} V_{11}\{x_1(t)\} - V_{35}^{-1} V_{31}\{x_1(t)\} +$$
$$V_{15}^{-1} V_{12}\{x_2(t)\} - V_{35}^{-1} V_{32}\{x_2(t)\} +$$
$$V_{15}^{-1} V_{13}\{x_3(t)\} - V_{35}^{-1} V_{33}\{x_3(t)\} +$$
$$V_{15}^{-1} V_{14}\{x_4(t)\} - V_{35}^{-1} V_{34}\{x_4(t)\}$$
$$= A_{21}\{x_1(t)\} + A_{22}\{x_2(t)\} + A_{23}\{x_3(t)\} + A_{24}\{x_4(t)\}$$

$$c) \quad z_3(t) = V_{13}^{-1}\{s_1(t)\} - V_{45}^{-1}\{s_4(t)\}$$
$$= V_{13}^{-1} V_{11}\{x_1(t)\} - V_{45}^{-1} V_{41}\{x_1(t)\} +$$
$$V_{13}^{-1} V_{12}\{x_2(t)\} - V_{45}^{-1} V_{42}\{x_2(t)\} +$$
$$V_{13}^{-1} V_{13}\{x_3(t)\} - V_{45}^{-1} V_{43}\{x_3(t)\} +$$
$$V_{13}^{-1} V_{14}\{x_4(t)\} - V_{45}^{-1} V_{44}\{x_4(t)\}$$
$$= A_{31}\{x_1(t)\} + A_{32}\{x_2(t)\} + A_{33}\{x_3(t)\} + A_{34}\{x_4(t)\}$$

$$d) \quad z_4(t) = V_{13}^{-1}\{s_1(t)\} - V_{55}^{-1}\{s_5(t)\}$$
$$= V_{13}^{-1} V_{11}\{x_1(t)\} - V_{55}^{-1} V_{51}\{x_1(t)\} +$$
$$V_{13}^{-1} V_{12}\{x_2(t)\} - V_{55}^{-1} V_{52}\{x_2(t)\} +$$
$$V_{13}^{-1} V_{13}\{x_3(t)\} - V_{55}^{-1} V_{53}\{x_3(t)\} +$$
$$V_{13}^{-1} V_{14}\{x_4(t)\} - V_{55}^{-1} V_{54}\{x_4(t)\}$$
$$= A_{41}\{x_1(t)\} + A_{42}\{x_2(t)\} + A_{43}\{x_3(t)\} + A_{44}\{x_4(t)\}$$

where $V_{kl}^{-1}$ is the inverse operator for $V_{kl}$, for example obtained along the lines of the Wiener type filter in Eqs. (21-26). In the above notation both the nonlinear propagation delay and the pulse form distortion is included in the filter operators, and the operator inversion hence implies correction for nonlinear propagation delay and pulse form distortion. For practical calculations of the inverse operators, one would do a direct delay correction for the nonlinear propagation delay, with a filter for the pulse form correction. This separation reduces the required length of the filter impulse responses. One should also note that operator inversion could be composed of a frequency mixing, fast time filter correction, fast time compression/expansion, and delay correction, per the discussion following Eqs. (26, 45). When the HF pulse propagates at the crest or trough of the LF pulse, the pulse form distortion can be negligible, and the inverse operator would be a delay correction only.

Note that if the $1^{st}$ measured signal ($s_1$) is obtained with zero LF pulse, we have $V_{1l} = V_{1l}^{-1} = I$, i.e. the identity operator. Applying $V_{k5}^{-1}$ on $s_k(t)$, $k=2, \ldots, 5$ and subtracting provides heavy suppression of $x_5(t)$. We can then proceed in the same way to suppress $x_4(t)$ from the above expressions by forming the signals $$a) \quad u_1(t) = A_{14}^{-1}\{z_1(t)\} - A_{24}^{-1}\{z_2(t)\} \quad (50)$$
$$= A_{14}^{-1} A_{11}\{x_1(t)\} - A_{24}^{-1} A_{21}\{x_1(t)\} +$$
$$A_{14}^{-1} A_{12}\{x_2(t)\} - A_{24}^{-1} A_{22}\{x_2(t)\} +$$
$$A_{14}^{-1} A_{13}\{x_3(t)\} - A_{24}^{-1} A_{23}\{x_3(t)\}$$
$$= B_{11}\{x_1(t)\} + B_{12}\{x_2(t)\} + B_{13}\{x_3(t)\}$$

$$b) \quad u_2(t) = A_{14}^{-1}\{z_1(t)\} - A_{34}^{-1}\{z_3(t)\}$$
$$= A_{14}^{-1} A_{11}\{x_1(t)\} - A_{34}^{-1} A_{31}\{x_1(t)\} +$$
$$A_{14}^{-1} A_{12}\{x_2(t)\} - A_{34}^{-1} A_{32}\{x_2(t)\} +$$
$$A_{14}^{-1} A_{13}\{x_3(t)\} - A_{34}^{-1} A_{33}\{x_3(t)\}$$
$$= B_{21}\{x_1(t)\} + B_{22}\{x_2(t)\} + B_{23}\{x_3(t)\}$$

$$c) \quad u_3(t) = A_{14}^{-1}\{z_1(t)\} - A_{44}^{-1}\{z_4(t)\}$$
$$= A_{14}^{-1} A_{11}\{x_1(t)\} - A_{44}^{-1} A_{41}\{x_1(t)\} +$$
$$A_{14}^{-1} A_{12}\{x_2(t)\} - A_{44}^{-1} A_{42}\{x_2(t)\} +$$
$$A_{14}^{-1} A_{13}\{x_3(t)\} - A_{44}^{-1} A_{43}\{x_3(t)\}$$
$$= B_{31}\{x_1(t)\} + B_{32}\{x_2(t)\} + B_{33}\{x_3(t)\}$$

and proceeding in the same manner to suppress $x_3(t)$, we obtain signals where Class I-III multiple scattering noise is heavily suppressed a) $q_1(t) = B_{13}^{-1}\{u_1(t)\} - B_{23}^{-1}\{u_2(t)\}$ (51)

$= B_{13}^{-1}B_{11}\{x_1(t)\} - B_{23}^{-1}B_{21}\{x_1(t)\} +$ $B_{13}^{-1}B_{12}\{x_2(t)\} - B_{23}^{-1}B_{22}\{x_2(t)\}$ $= C_{11}\{x_1(t)\} + C_{12}\{x_2(t)\}$ c) $q_2(t) = B_{13}^{-1}\{u_1(t)\} - B_{33}^{-1}\{u_3(t)\}$ $= B_{13}^{-1}B_{11}\{x_1(t)\} - B_{33}^{-1}B_{31}\{x_1(t)\} +$ $B_{13}^{-1}B_{12}\{x_2(t)\} - B_{33}^{-1}B_{32}\{x_2(t)\}$ $= C_{21}\{x_1(t)\} + C_{22}\{x_2(t)\}$

We can then proceed in the same manner and eliminate $x_2(t)$, or we can solve Eq. (51) with the algebraic formulas for two linear equations with two unknowns as $x_l(t)=x_1(t)=[C_{11}C_{22}-C_{12}C_{21}]^{-1}\{C_{22}\{q_1(t)\}-C_{12}\{q_2(t)\}\}$ a)

$x_n(t)=x_2(t)=[C_{11}C_{22}-C_{12}C_{21}]^{-1}\{C_{11}\{q_2(t)\}-C_{21}\{q_1(t)\}\}$ b) (52)

The linearly scattered HF signal $x_1(t)$ is often much stronger than the nonlinear signal $x_2(t)$, and one can then approximate $x_l(t)=x_1(t)=C_{11}^{-1}\{q_1(t)\}$. We note as for Eq. (45) that if we remove the inverse determinant we get filtered versions of the linearly and nonlinearly scattered signals, $x_1(t)$ and $x_2(t)$.

The operators in Eqs. (43, 44, 48) are generally filters including nonlinear propagation delays with impulse/frequency responses that can be approximated to stationary within intervals $T_i=T(t_i)$ as in Eq. (20), where $t_i$ is the center of the interval. The inverse filters of Eqs. (45-52) can be solved via a Fourier transform as in Eqs. (20-26) or with the discussion following Eq. (26, 45). One can also do a Fourier transform of Eqs. (43, 44, 48) for each interval $T_i$, which gives a set of ordinary algebraic equations for each frequency of the Fourier transforms $X_{li}(\omega)$ of $x_{li}(t)$. These equations are then solved by well known analytic or numerical methods for such equations, and the time functions for $x_{1i}(t)$ and $x_{2i}(t)$ on the time intervals $T_i$ are then obtained by Fourier inversion. We note that when the pulse form distortion is negligible, the Fourier transform of $v_{kl}(t;t_i) \to e^{-i\omega\tau_k(t_i)}$ and $v_{kl}^r(t;t_i) \to e^{-i\omega\tau_k(t_i)}$ where $\tau_k(t_i)$ is the nonlinear propagation delay in the Fourier interval $T_i$, and $\tau(t_i)$ is the nonlinear propagation delay at the $1^{st}$ scatterer in the interval $T_i$ of the pulse reverberation noise (see Eq. (42)).

For estimation of the actual delay and pulse distortion corrections, the $V_{kl}$ operators in Eqs. (43, 44, 48) can be estimated based on the following considerations: The LF pulse has so low frequency compared to the image depth (typical image depth $\sim 30\lambda_{LF}$) that one can often neglect individual variations of absorption and wave front aberration for the LF beam for specific types of measurements. The nonlinear propagation delays and pulse distortion can therefore often be obtained with useful accuracy from simulations of the composite LF/HF elastic waves with known, assumed, adjusted, or estimated local propagation parameters. The propagation parameters are composed of the local mass density and linear and nonlinear elasticity parameters of the material. For adequately adjusted local nonlinear elasticity parameters as a function of propagation path of the HF pulse, one can use the formula in Eq. (3) to obtain an estimate of the nonlinear propagation delay $\tau_k(t)$.

The correction delays can for example therefore be obtained from 1. simulated nonlinear propagation delays in simulations of the composite LF/HF elastic waves with one of
   assumed local propagation parameters for the materials, or
   manual adjustment of local propagation material parameters to one or both of
   i) minimize the pulse reverberation noise in the observed image, and
   ii) minimize the linear scattering component in the image, or
2. manual adjustment of the local correction delays to one or both of
   i) minimize the pulse reverberation noise in the observed image, and
   ii) minimize the linear scattering component in the image, or
3. as estimates of the nonlinear propagation delays for example as described in U.S. patent application Ser. No. 11/189,350 (US Pub 2005/027835) and U.S. Pat. No. 8,038,616, or
4. a combination of the above.

The pulse distortion correction can similarly be obtained from 1. simulated nonlinear pulse distortions in simulations of the composite LF/HF elastic waves with one of
   assumed local propagation parameters for the materials, or
   manual adjustment of local material propagation parameters to one or both of
   i) minimize the pulse reverberation noise in the observed image, and
   ii) minimize the linear scattering component in the image, or
   elastic parameters obtained from the fast time gradient of estimated correction delays, for example according to Eq. (7). Said estimated correction delays are for example obtained from manual local adjustment of the nonlinear propagation delays or estimations from received signals as described above, or
2. from direct estimation of the pulse distortion from the frequency spectrum of the received HF signals from a region of scatterers, and this spectral estimate is used to estimate fast time expansion/compression or $v_k(t,t_0)$ in Eqs. (18-20), or
3. a combination of points 1 and 2.

The manual adjustment of local propagation (elasticity) parameters or nonlinear correction delays can for example be done through multiple user controls in a set of selected depth intervals, for maximal suppression of the linearly scattered signal, or for maximal suppression of pulse reverberation noise as discussed. For feedback one can for example use the image signal as displayed on the screen. One can also conveniently combine the methods, for example that the simulation estimates with assumed local elasticity parameters are applied first with further automatic estimation or manual adjustments to one or both of i) minimize the pulse reverberation noise in the observed image, and ii) minimize the linear scattering component in the image.

When the object scatterers move between pulse reflections from different transmitted pulse complexes, the $V_{kl}\{\}$ operators also contain a Doppler delay in addition to the nonlinear propagation delay, and one should then do a correction for the sum delay of the nonlinear propagation and Doppler delays. We note that for suppression of pulse reverberation noise, one shall correct for the sum delay at the $1^{st}$ scatterer, while for suppression of linear scattering to observe nonlinear scattering one shall correct for the sum delay at t. With a relative variation in pulse amplitude of $p_k$ between the LF pulses, the nonlinear propagation delay can be approximated as $p_k\tau(t)$, and estimating the sum delay as $\tau_{Tk}(t)=kT_d(t)+p_k\tau(t)$, the sum of the Doppler and nonlinear propagation delay for several received HF signals, will then allow estimation of the Doppler and nonlinear propagation delays separately, for example through elimination from three pulse complexes giving: $\tau_{T1}(t)=T_d(t)+\tau(t)$ and $\tau_{T2}(t)=2T_d(t)+\tau(t)$. This is further described in U.S. patent application Ser. No. 11/189,350 (US Pat Pub 2005/0277835) and U.S. Pat. No. 8,036,616.

To further elaborate on methods of suppression of pulse reverberation noise and linear scattering, we first give an example according to the invention using a sequence of 3 transmitted pulse complexes, where the transmitted LF pulse amplitudes of the successive pulse complexes are approximately $P_0$, 0, and approximately $-P_0$. A strong scatterer close to fast time $t_1$ produces pulse reverberation noise, and according to Eqs. (43, 48) we can express the received HF signals from the 3 pulse complexes as $$s_+(t)=V_t^+\{x_+(t+\tau(t))\}+V_{t_1}^+\{w(t+\tau(t_1))\}\ x_+(t)=x_l(t)+x_{n+}(t)$$

$$s_0(t)=x_l(t)+w(t)$$

$$s_-(t)=V_t^-\{x_-(t-\tau(t))\}+V_{t_1}^-\{w(t-\tau(t_1))\}\ x_-(t)=x_l(t)-x_{n-}(t)$$

$$V_t^\pm\{x_\pm(t)\}=\int dt_0 v_\pm(t-t_0,t_0)x_\pm(t_0)$$

$$V_{t_1}^\pm\{w(t)\}=\int dt_0 v_\pm(t-t_0,t_1)w(t_0) \quad (53)$$

where now $V_t^\pm$ represents only the pulse form distortion while the nonlinear propagation delay is explicitly included in the time argument of the functions as in Eqs. (19-26) (See comments after Eqs. (24, 40)). The pulse reverberation noise is $w(t)$ with the 1$^{st}$ and 3$^{rd}$ scatterer 602 at the fast time (depth-time) location around $t_1=2r_1/c$. We then do a correction for the + and – signals for the pulse form distortion and nonlinear propagation delay at the 1$^{st}$ strong scatterer 602 located at fast time $t_1$. With pulse form and nonlinear propagation delay corrections at fast time $t_1$ we get $$y_+(t)=H_{t_1}^+\{s_+(t-\hat{\tau}(t_1))\}=H_{t_1}^+V_t^+\{x_+(t+\tau(t)-\hat{\tau}(t_1))\}+w(t)$$

$$y_-(t)=H_{t_1}^-\{s_-(t+\hat{\tau}(t_1))\}=H_{t_1}^-V_t^-\{x_-(t-\tau(t)+\hat{\tau}(t_1))\}+w(t)$$

$$H_{t_1}^+\{s_+(t)\}=\int dt_0 h_+(t-t_0,t_1)s_+(t_0)$$

$$H_{t_1}^-\{s_-(t)\}=\int dt_0 h_-(t-t_0,t_1)s_-(t_0) \quad (54)$$

where $\hat{\tau}(t_1)$ is the estimated nonlinear propagation delay at fast time $t_1$, and $H_{t_1}^+\{\ \}$ represents the pulse distortion correction for the positive LF pulse with the distortion at $t_1$, and $H_{t_1}^-\{\ \}$ represents the pulse distortion correction for the negative LF pulse with the distortion at $t_1$. The $H_t^\pm$ represents a general pulse distortion correction, for example along the lines of Wiener filtering given in Eqs. (21-26), combined frequency mixing and fast time filtering, modifications of the transmitted pulses, fast time expansion/compression of the received HF signal as discussed following Eq. (26, 45) in relation to FIG. 2C and FIG. 2D, or a combination of these. One can hence obtain a HF signal with improved suppression of the pulse reverberation noise (609/611) by the combination $$y_+(t)-y_-(t)=H_{t_1}^+V_t^+\{x_+(t+\tau(t)-\hat{\tau}(t_1))\}-H_{t_1}^-V_t^-\{x_-(t-\tau(t)+\hat{\tau}(t_1))\} \quad (55)$$

For noise suppression with stationary objects, one might hence transmit only two pulse complexes with amplitudes P0 and –P0 of the LF pulse, or potentially with zero LF pulse in one of the pulse complexes.

For additional suppression of the HF linear scattering components to provide a nonlinear HF signal representing nonlinear scattering from the object, we can form the following combinations of the 3-pulse sequence for suppression of the pulse reverberation noise $$z_1(t)=y_+(t)-s_0(t)=H_{t_1}^+V_t^+\{x_+(t+\tau(t)-\hat{\tau}(t_1))\}-x_l(t_1)$$

$$z_2(t)=s_0(t)-y_-(t)=x_l(t)-H_{t_1}^-V_t^-\{x_-(t-\tau(t)+\hat{\tau}(t_1))\} \quad (56)$$

The signal component from the scatterer 603 obtains further pulse form distortion and nonlinear propagation delay due to the further propagation along the transmit LF pulse from 602 to 603. The HF pulses for positive and negative LF transmit pulses then obtains opposite pulse form distortion, i.e. a HF pulse length compression for the positive LF pulse gives a similar HF pulse length expansion for the negative LF pulse (and vice versa), and the nonlinear propagation delays have opposite signs. With zero transmitted LF pulse there is no HF pulse form distortion or nonlinear propagation delay. We then delay $z_1$ with $(\hat{\tau}(t)-\hat{\tau}(t_1))/2$ and advance $z_2$ with $(\hat{\tau}(t)-\hat{\tau}(t_1))/2$, where $\hat{\tau}(t)$ is the estimated nonlinear propagation delay of the signals at fast time t, and pulse distortion correct $z_1$ and $z_2$ for half the pulse length compression/expansion from 602 to 603.

We note from Eq. (53) that the nonlinear component of the scattered signal is zero for zero LF pressure. With pulse distortion correction for half the LF pressure, we note that for the linear components of HF scattered signal we have $$H_{t;t_1}^{+1/2}H_{t_1}^+V_t^+\{x_l(t+(\tau(t)-\hat{\tau}(t_1))/2)\}=H_{t;t_1}^{-1/2}\{x_l(t+(\tau(t)-\hat{\tau}(t_1))/2)\}$$

$$H_{t;t_1}^{-1/2}H_{t_1}^-V_t^-\{x_l(t-(\tau(t)-\hat{\tau}(t_1))/2)\}=H_{t;t_1}^{+1/2}\{x_l(t-(\tau(t)-\hat{\tau}(t_1))/2)\} \quad (57)$$

where the $H_{t;t_1}^{+1/2}$ implies correcting the signals for half the pulse distortion produced by the positive LF pulse from $t_1$ to t, and the $H_{t;t_1}^{-1/2}$ implies correcting for half the pulse distortion of the negative LF pulse from $t_1$ to t. These corrections can for the 2$^{nd}$ order approximation of the nonlinear elasticity as in Eq. (1) be estimated from the distortion from $t_1$ to t for a signal with half the transmitted LF amplitude.

Hence does the following combination produce improved suppression of the linear scattering components to give a signal that represents the nonlinear HF scattering with highly suppressed reverberation noise $$\hat{x}_n(t) = \quad (58)$$
$$H_{t;t_1}^{+1/2}\{z_1(t-(\hat{\tau}(t)-\hat{\tau}(t_1))/2)\}-H_{t;t_1}^{-1/2}\{z_2(t+(\hat{\tau}(t)-\hat{\tau}(t_1))/2)\} \approx$$
$$H_{t;t_1}^{+1/2}H_{t_1}^+V_t^+\{x_+(t+(\tau(t)-\hat{\tau}(t_1))/2)\}-$$
$$H_{t;t_1}^{+1/2}\{x_l(t-(\tau(t)-\hat{\tau}(t_1))/2)\}-H_{t;t_1}^{-1/2}\{x_l(t+(\tau(t)-\hat{\tau}(t_1))/2)\}+$$
$$H_{t;t_1}^{-1/2}H_{t_1}^-V_t^-\{x_-(t-(\tau(t)-\hat{\tau}(t_1))/2)\} \approx$$
$$H_{t;t_1}^{+1/2}H_{t_1}^+V_t^+\{x_{n+}(t+(\tau(t)-\hat{\tau}(t_1))/2)\}-$$
$$H_{t;t_1}^{-1/2}H_{t_1}^-V_t^-\{x_{n-}(t-(\tau(t)-\hat{\tau}(t_1))/2)\}$$

An estimate of the linear scattering can be obtained as $$\hat{x}_l(t) = H^+_{t;t_1}\{z_1(t-(\hat{\tau}(t)-\hat{\tau}(t_1)))\} - H^-_{t;t_1}\{z_2(t+(\hat{\tau}(t)-\hat{\tau}(t_1)))\} = \quad (59)$$

$$H^+_t V^+_t\{x_l(t)\} + H^+_t V^+_t\{x_{n+}(t)\} - H^+_{t;t_1}\{x_l(t-(\hat{\tau}(t)-\hat{\tau}(t_1)))\} -$$

$$H^-_{t;t_1}\{x_l(t+(\hat{\tau}(t)-\hat{\tau}(t_1)))\} + H^-_t V^-_t\{x_l(t)\} - H^-_t V^-_t\{x_{n-}(t)\} \approx$$

$$2x_l(t) - H^+_{t;t_1}\{x_l(t-(\hat{\tau}(t)-\hat{\tau}(t_1)))\} - H^-_{t;t_1}\{x_l(t+(\hat{\tau}(t)-\hat{\tau}(t_1)))\}$$

where $H_{t;t_1}^\pm$ represents the correction for the pulse form distortion from $t_1$ to $t$, so that $H_{t;t_1}^\pm H_{t_1}^\pm = H_t^\pm$ which is the correction for the pulse form distortion from 0 to t. We hence have $H_{t;t_1}^\pm H_{t_1}^\pm V_t^\pm = H_t^\pm V_t^\pm = I$, i.e. the identity operator. We have assumed that $x_{n-}(t) \approx x_{n+}(t)$ which is exact for $2^{nd}$ order elasticity. However, the nonlinear scattering is much weaker than the linear scattering which makes the approximations in Eq. (59) adequate also for other nonlinear scattering.

The combination of signals with opposite polarity of the LF pulse as in Eqs. (55, 58, 59), reduces required accuracy in the estimated delay and pulse distortion corrections, as seen from the following analysis. This opens for an approximate but robust method to suppress both the pulse reverberation noise and the linear scattering from the received HF signals in Eq. (53). We model the pulse form distortion as a pure time compression/expansion as $$V_t^\pm\{x_h(t\pm\tau(t))\} = \int dt_0 u[(1\pm a(t))(t-t_0),t_0]\sigma_h(t_0\pm\tau(t))$$

$$V_{t_1}^\pm\{w(t\pm\tau_1)\} = \int dt_0 u[(1\pm a_1)(t-t_0),t_1]\sigma_w(t_0\pm\tau_1) \quad (60)$$

where $u(t,t_0)$ is the received pulse from a point scatterer at $t_0$ with zero LF pulse, $\sigma_h(t_0)$ is the scatterer density for the linear scattering (h=l), the nonlinear scattering with positive LF pulse (h=n+), the nonlinear scattering for negative LF pulse (h=n−), and $\sigma_w(t_0)$ is an equivalent scatterer density for multiple scattering noise where the $1^{st}$ scatterer is at $t_1$. $\tau(t)$ is the nonlinear propagation delay down to fast time t and the factor $(1\pm a(t))$ represents pulse time compression/expansion produced by gradients of the LF pulses along the HF pulses, where the sign of $\pm a(t)$ is given by the sign of the LF pulses. $\tau_1$ and $a_1$ are the nonlinear propagation delay and pulse time compression factor where the $1^{st}$ scatterer is found at $t_1$, which is the situation for the pulse reverberation noise. We note that for materials that can be approximated with $2^{nd}$ order nonlinear elasticity as in Eqs. (1, 5) we have $\sigma_{n-}(t_0) = \sigma_{n+}(t_0)$.

When the HF pulse is long compared to the LF pulse period, the approximation in Eq. (60) of pure time compression/expansion of the pulse becomes less accurate, and one can improve the approximation by introducing higher order terms $(1\pm a_1(t))(t-t_0)ma_2(t)(t-t_0)^2\pm\ldots$ in the pulse argument in Eq. (60), as discussed in relation to Eq. (26). However the analysis of the corrections will be similar, and for simplified notation we therefore use only the linear compression in Eq. (60), where the expansion to higher order terms are obvious to anyone skilled in the art. We correct the signals in Eq. (60) for pulse compression/expansion for example with a fast time filter in analogy with Eqs. (19-26), or through modifications of the transmitted HF pulses as described in relation to FIG. 2D, or through time expansion/compression of the received signal as described above, or through frequency mixing, or a combination of the above. Combined correction for nonlinear propagation delay and pulse form distortion of the signals in Eq. (60) then gives $$H_{\pm a_c} V_t^\pm\{x_h(t\pm(\tau(t)-\tau_c))\} = \quad (61)$$

$$\int dt_0 u[(1\pm(a(t)-a_c))(t-t_0),t_0]\sigma_h(t_0\pm(\tau(t)-\tau_c)) \approx$$

$$x_h(t)\pm(a(t)-a_c)\int dt_0(t-t_0)\dot{u}(t-t_0,t_0)\sigma_h(t_0)\pm$$

$$(\tau(t)-\tau_c)\int dt_0 u(t-t_0,t_0)\dot{\sigma}_h(t_0)$$

$$H_{\pm a_c} V_{t_1}^\pm\{w(t\pm(\tau_1-\tau_c))\} =$$

$$\int dt_0 u[(1\pm(a_1-a_c))(t-t_0),t_1]\sigma_w(t_0\pm(\tau_1-\tau_c)) \approx$$

$$w(t)\pm(a_1-a_c)\int dt_0(t-t_0)\dot{u}(t-t_0,t_1)\sigma_w(t_0)\pm$$

$$(\tau_1-\tau_c)\int dt_0 u(t-t_0,t_1)\dot{\sigma}_w(t_0)$$

where $$x_h(t) = \int dt_0 u(t-t_0,t_0)\sigma_h(t_0)$$

$$w(t) = \int dt_0 u(t-t_0,t_1)\sigma_w(t_0)$$

and $H_{\pm a_c}$ is the correction for the pulse time compression/expansion with the factor $1\pm a_c$, and the approximate expressions are obtained with Taylor series expansion of the functions to the $1^{st}$ order. The accuracy of the expansion then depends on the magnitude of $a-a_c$ and $\tau-\tau_c$, and can be adjusted by adjusting $a_c$ and $\tau_c$. The corrected received signals then take the form $$y_\pm(t) = H_{\pm a_c}\{s_\pm(t\mp\tau_c)\} \quad (62)$$

$$= H_{\pm a_c} V_t^\pm\{x_l(t\pm(\tau(t)-\tau_c))\} \pm$$

$$H_{\pm a_c} V_t^\pm\{x_{n\pm}(t\pm(\tau(t)-\tau_c))\} +$$

$$H_{\pm a_c} V_{1t}^\pm\{w(t\pm(\tau(t)-\tau_c))\}$$

Choosing $a_c \approx a_1$ and $\tau_c \approx \tau_1$ we can in analogy with Eq. (55) form a noise suppressed estimate of the linear scattering as $$y_+(t) - y_-(t) = H_{a_1}\{s_+(t-\tau_1)\} - H_{-a_1}\{s_-(t+\tau_1)\} = \quad (63)$$

$$x_l(t) + (a(t)-a_1)\int dt_0(t-t_0)\dot{u}(t-t_0,t_0)\sigma_l(t_0) +$$

$$(\tau(t)-\tau_1)\int dt_0 u(t-t_0,t_0)\dot{\sigma}_l(t_0) + w(t) - x_l(t) +$$

$$(a(t)-a_1)\int dt_0(t-t_0)\dot{u}(t-t_0,t_0)\sigma_l(t_0) +$$

$$(\tau(t)-\tau_1)\int dt_0 u(t-t_0,t_0)\dot{\sigma}_l(t_0) - w(t)$$

which gives $$y_+(t)-y_-(t) \approx 2(a(t)-a_1)\int dt_0(t-t_0)\dot{u}(t-t_0,t_0)\sigma_l(t_0) +$$
$$2(\tau(t)-\tau_1)\int dt_0 u(t-t_0,t_0)\dot{\sigma}_l(t_0) \quad (64)$$

where we have neglected the nonlinear scattering compared to the linear scattering.

A noise suppressed estimate of the nonlinearly scattered signal can be found through an approximation of Eqs. (56, 58) as $$\hat{x}_n(t) = y_+(t) - s_0(t) - (s_0(t) - y_-(t)) \quad (65)$$
$$= y_+(t) + y_-(t) - 2s_0(t)$$

Inserting the approximated expressions for the corrected signals from Eqs. (61, 62) gives $$\hat{x}_n(t) \approx x_l(t) + (a(t) - a_c) \int dt_0 (t - t_0) \dot{u}(t - t_0, t_0) \sigma_l(t_0) + \quad (66)$$

$$(\tau(t) - \tau_c) \int dt_0 u(t - t_0, t_0) \dot{\sigma}_l(t_0) + H_{a_c} V_t^+ \{x_{n+}(t + (\tau(t) - \tau_c))\} +$$

$$w(t) + (a_1 - a_c) \int dt_0 (t - t_0) \dot{u}(t - t_0, t_1) \sigma_w(t_0) +$$

$$(\tau_1 - \tau_c) \int dt_0 u(t - t_0, t_1) \dot{\sigma}_w(t_0) + x_l(t) -$$

$$(a(t) - a_c) \int dt_0 (t - t_0) \dot{u}(t - t_0, t_0) \sigma_l(t_0) -$$

$$(\tau(t) - \tau_c) \int dt_0 u(t - t_0, t_0) \dot{\sigma}_l(t_0) - H_{-a_c} V_t^- \{x_{n-}(t - (\tau(t) - \tau_c))\} +$$

$$w(t) - (a_1 - a_c) \int dt_0 (t - t_0) \dot{u}(t - t_0, t_1) \sigma_w(t_0) -$$

$$(\tau_1 - \tau_c) \int dt_0 u(t - t_0, t_1) \dot{\sigma}_w(t_0) - 2x_l(t) - 2w(t)$$

which reduces to $$\hat{x}_n(t) \approx H_{a_c} V_t^+ \{x_{n+}(t+(\tau(t)-\tau_c))\} - H_{-a_c} V_t^- \{x_{n-}(t-(\tau(t)-\tau_c))\} \quad (67)$$

Using the $1^{st}$ order Taylor expansion in a(t) in Eq. (61) we can approximate Eq. (67) to $$\hat{x}_n(t) \approx x_{n+}(t+(\tau(t)-\tau_c)) - x_{n-}(t-(\tau(t)-\tau_c)) + (a(t)-a_c)\int dt_0(t-t_0)\dot{u}(t-t_0,t_0)\{\sigma_{n+}(t_0+(\tau(t)-\tau_c)) + \sigma_{n-}(t_0-(\tau(t)-\tau_c))\} \quad (68)$$

For materials where the $2^{nd}$ order approximation of the nonlinear elasticity in Eq. (1) is adequate, we have $x_{n-}(t) = x_{n+}(t)$ and $\sigma_{n-}(t) = \sigma_{n+}(t)$. However, when $\tau_c(t) \neq \tau(t)$ and/or $a(t) \neq a_c$, the detection signal in Eq. (68) is nonzero also in this case. With scattering from micro gas bubbles we can have $x_{n-}(t) \neq x_{n+}(t)$ and $\sigma_{n-}(t) \neq \sigma_{n+}(t)$ which increases the detection signal. This is specially found for HF close to the bubble resonance frequency where a change in the polarity of the LF pulse changes the phase of the nonlinear scattering signal, or with so high LF pulse amplitude that the LF bubble compression shows strong deviation from the $2^{nd}$ order nonlinearity.

We hence see that the sum of $y_+$ and $y_-$ in Eq. (65, 66) gives robust and strong canceling of the pulse form distortion and the nonlinear propagation delays. Accurate assessment of $a_c$ and $\tau_c$ is hence not so critical which makes the procedures robust. When $a(t)-a_c$ and $\tau(t)-\tau_c$ become so large that $2^{nd}$ and higher order even terms in the Taylor series of $u[(1 \pm (a-a_c))(t-t_0), t_0] \sigma_h(t_0 \pm (\tau - \tau_c))$ become important, the suppression of the linear scattering and the pulse reverberation noise is reduced. However, by choosing $\tau_c$ close to $\tau_1$ and $a_c$ close to $a_1$, Eq. (63, 66) gives good approximations for suppression of the pulse reverberation noise, and choosing $\tau_c$ close to $\tau(t)$ and $a_c$ close to $a(t)$ Eq. (66) gives good suppression for the linear scattering at fast time t. In many situations suppression of pulse reverberation noise is most important up to medium depths, while suppression of linear scattering is the most important for larger depths. One can then use a delay and compression correction $\tau_c \approx \tau_1$ and $a_c \approx a_1$ for the lower depths and a delay and compression correction delay $\tau_c \approx \tau(t)$ and $a_c \approx a(t)$ for the larger depths.

Figure 8:
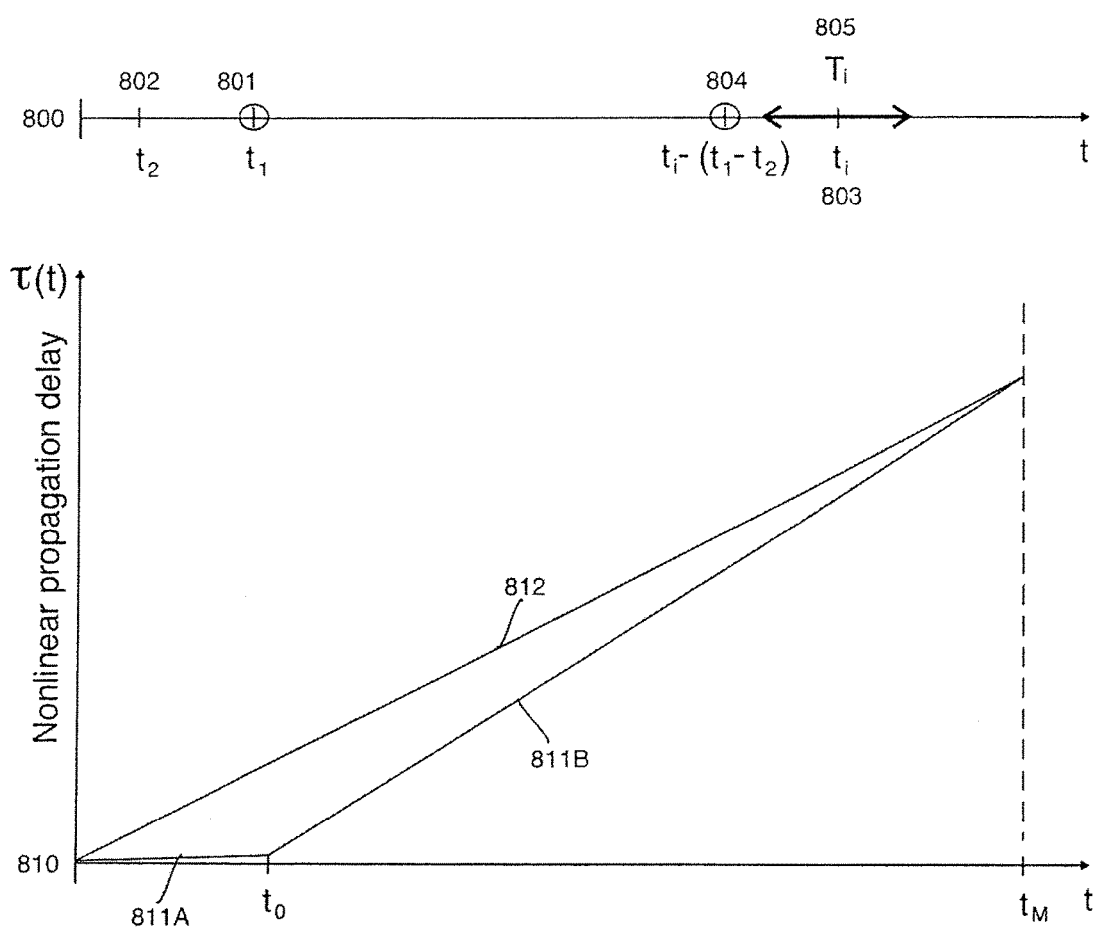
FIG. 8 shows conceptual illustration of combined suppression for Class I and II pulse reverberation noise.

We have in Eqs. (53-68) analyzed the situation of a single $1^{st}$ scatterer, but as discussed in relation to Eq. (37), Class I and Class II noise always coexist, and are equal for zero LF pulse when the transmit and received beams are equal. Suppose we transmit two pulse complexes with opposite polarity of the LF pulse, and correct and subtract the received HF signals for the nonlinear propagation lags and possible pulse form distortions at the location of the $1^{st}$ scatterer of Class I noise. This will produce a strong suppression of the Class I noise, but a limited suppression of the Class II noise. Combined suppression of Class I and Class II noise can be obtained with the methods developed below. In FIG. 8, 800 shows a fast time scale with a strong $1^{st}$ scatterer at $t_l$ (801). A $2^{nd}$ scatterer (802) at fast time $t_2$ rescatters the back scattered wave to a forward wave. To have substantial Class I pulse reverberation noise at fast time t (803) we must also have a $3^{rd}$ strong scatterer at $t-(t_1-t_2)$, illustrated as 804 on the time scale 800. We then have a similar Class II pulse reverberation noise where the $1^{st}$ scatterer is at 804 $t-(t_1-t_2)$, a $2^{nd}$ scatterer at $t_2$ (802) and the $3^{rd}$ scatterer is at $t_l$ (801).

With a continuous distribution of scatterers we assume that with zero LF pulse the Class II pulse reverberation noise is $x_r(t;t_1,t_2)dt_1 dt_2$, where the $3^{rd}$ Class II scatterer is in the interval $dt_1$ around $t_1$ with the $2^{nd}$ Class II scatterer in the interval $dt_2$ around $t_2$ and the 1st scatterer at $t_3=t-(t_1-t_2)$. The Class I noise has the same scatterers in the reverse order. We can then with nonzero LF pulse model the Class I and II pulse reverberation noise as $$dr(t; p_k) = dt_1 dt_2 \Big\{ \underbrace{q(t; t_1) \otimes_t v_k(t; t_1; p_k) \otimes_t x_r(t - p_k \tau(t_1); t_1, t_2)}_{\text{Class I}} + \quad (69)$$

$$\underbrace{v_k(t; t-t_1+t_2; p_k) \otimes_t x_r(t - p_k \tau(t-t_1+t_2); t_1, t_2)}_{\text{Class II}} \Big\}$$

The filter $q(t;t_1)$ takes care of the differences between the transmit and receive beams, where for equal transmit and receive beams $q(t;t_1) = \delta(t)$. The transmit amplitude of the LF pulse is $p_k$, where in particularly when the transmitted LF pulse changes polarity, $p_k$ changes sign. $p_k \tau(\bullet)$ is the nonlinear propagation delay at the depth of the $1^{st}$ scatterer, which is $t_1$ for Class I and depth $t-t_1+t_2$ for Class II noise. We have separated out the nonlinear propagation delay at the depth of the $1^{st}$ scatterer so that the filter $v_k(t;t_1;p_k)$ only takes care of the nonlinear pulse form distortion of the HF pulse by the LF pulse at the depth of the $1^{st}$ scatterer. The Fourier transform of the expression in Eq. (69) over an interval $T_i$ (805) around $t_i$ (803) gives $$dR_i(\omega; p_k) = dt_1 dt_2 X_{ri}(\omega; t_1, t_2) \times \{Q_i(\omega; t_1) V_{ik}(\omega; t_1; p_k) e^{-i\omega p_k \tau(t_1)} + \quad (70)$$

$$V_{ik}(\omega; t_i - t_1 + t_2; p_k) e^{-i\omega p_k \tau(t_i - t_1 + t_2)} \} =$$

$$dt_1 dt_2 X_{ri}(\omega; t_1, t_2) A_i(\omega; t_1, t_2; p_k) e^{-i\omega p_k [\tau(t_i - t_1 + t_2) + \tau(t_1)]/2}$$

where we have defined $$A_i(\omega; t_1, t_2; p_k) = Q_i(\omega; t_1) V_{ik}(\omega; t_1; p_k) e^{i\omega p_k [\tau(t_i - t_1 + t_2) - \tau(t_1)]/2} + \quad (71)$$

$$V_{ik}(\omega; t_i - t_1 + t_2; p_k) e^{-i\omega p_k [\tau(t_i - t_1 + t_2) - \tau(t_1)]/2} =$$

-continued $$[Q_i(\omega; t_1)V_{ik}(\omega; t_1; p_k) + V_{ik}(\omega; t_i - t_1 + t_2; p_k)]$$

$$\cos(\omega p_k[\tau(t_i - t_1 + t_2) - \tau(t_1)]/2) +$$

$$i[Q_i(\omega; t_1)V_{ik}(\omega; t_1; p_k) - V_{ik}(\omega; t_i - t_1 + t_2; p_k)] \quad (5)$$

$$\sin(\omega p_k[\tau(t_i - t_1 + t_2) - \tau(t_1)]/2)$$

The combined Class I/II pulse reverberations that give noise at t in $T_i$ around $t_i$ with $1^{st}/3^{rd}$ scatterer at $t_1$ and $2^{nd}$ scatterer at $t_2$, can hence be separated into a common nonlinear propagation delay $\tau_{ki}(t_1,t_2;p_k) = p_k[\tau(t_i-t_1+t_2)+\tau(t_1)]/2$ and a signal component $A_{ik}(\omega;t_1,t_2;p_k)$ that includes nonlinear pulse form distortion. The total Class I and II noise for a variability of scatterers is then $$R_i(\omega; p_k) = \int_0^{t_{2m}} dt_2 \int_{t_2}^{(t_i+t_{2m})/2} dt_1 X_{ri}(\omega; t_1, t_2) \quad (72)$$

$$A_i(\omega; t_1, t_2; p_k)e^{-i\omega p_k[\tau(t_i-t_1+t_2)+\tau(t_1)]/2} =$$

$$\int_0^{(t_i+t_{2m})/2} dt_1 \int_0^{\min(t_1, t_{2m})} dt_2 X_{ri}(\omega; t_1, t_2)$$

$$A_i(\omega; t_1, t_2; p_k)e^{-i\omega p_k[\tau(t_i-t_1+t_2)+\tau(t_1)]/2}$$

where for $t_{2m} < t_i$ is the maximal depth of $2^{nd}$ scatterers. We extract a delay $p_k\tau_{nik}$ for correction, and modify this equation to $$R_i(\omega; p_k) = e^{-i\omega p_k \tau_{nik}} N_i(\omega; p_k) \quad (73)$$

$$N_i(\omega; p_k) = \int_0^{t_{2m}} dt_2 \int_{t_2}^{(t_i+t_{2m})/2} dt_1 X_{ri}(\omega; t_1, t_2)$$

$$A_i(\omega; t_1, t_2; p_k)e^{-i\omega p_k[\tau(t_i-t_1+t_2)+\tau(t_1)-2\tau_{nik}]/2}$$

$\tau_{nik}$ should be selected so that the phase of $N_i$ is minimized. Inserting $A_i$ from Eq. (71), we get $$N_i(\omega; p_k) == \quad (74)$$

$$\int_0^{t_{2m}} dt_2 \int_{t_2}^{(t_i+t_{2m})/2} dt_1 X_{ri}(\omega; t_1, t_2)[Q_i(\omega; t_1)V_{ik}(\omega; t_1; p_k) + V_{ik}(\omega;$$

$$t_i - t_1 + t_2; p_k)] \times \cos(\omega p_k[\tau(t_i - t_1 + t_2) - \tau(t_1)]/2)$$

$$\cos(\omega p_k[\tau(t_i - t_1 + t_2) + \tau(t_1) - 2\tau_{nik}]/2) +$$

$$\int_0^{t_{2m}} dt_2 \int_{t_2}^{(t_i+t_{2m})/2} dt_1 X_{ri}(\omega; t_1, t_2)$$

$$[Q_i(\omega; t_1)V_{ik}(\omega; t_1; p_k) - V_{ik}(\omega; t_i - t_1 + t_2; p_k)] \times$$

$$\sin(\omega p_k[\tau(t_i - t_1 + t_2) - \tau(t_1)]/2)$$

$$\sin(\omega p_k[\tau(t_i - t_1 + t_2) + \tau(t_1) - 2\tau_{nik}]/2) -$$

$$i \int_0^{t_{2m}} dt_2 \int_{t_2}^{(t_i+t_{2m})/2} dt_1 X_{ri}(\omega; t_1, t_2)[Q_i(\omega; t_1)V_{ik}(\omega; t_1; p_k) -$$

$$V_{ik}(\omega; t_i - t_1 + t_2; p_k)] \times$$

$$\cos(\omega p_k[\tau(t_i - t_1 + t_2) - \tau(t_1)]/2)$$

$$\sin(\omega p_k[\tau(t_i - t_1 + t_2) + \tau(t_1) - 2\tau_{nik}]/2) -$$

$$i \int_0^{t_{2m}} dt_2 \int_{t_2}^{(t_i+t_{2m})/2} dt_1 X_{ri}(\omega; t_1, t_2)[Q_i(\omega; t_1)V_{ik}(\omega; t_1; p_k) +$$

$$V_{ik}(\omega; t_i - t_1 + t_2; p_k)] \times$$

-continued $$\cos(\omega p_k[\tau(t_i - t_1 + t_2) - \tau(t_1)]/2)$$

$$\sin(\omega p_k[\tau(t_i - t_1 + t_2) + \tau(t_1) - 2\tau_{nik}]/2)$$

Minimum phase of $N_i$ is found for the $\tau_{nik}$ that makes the sum of the last two integrals zero. This can be difficult to obtain for all angular frequencies in the general situation, and a best solution can then be to make the last integral zero for the center angular frequency $\omega_0$ of the signal. This determines the nonlinear propagation delay for the noise component $\tau_{nik}$ from the best approximation to the phase of the noise $R_i$ by a frequency-linear phase across the signal frequency band.

The total received signal in $T_i$ can then be written as $$S_{ik}(\omega;p_k) = e^{-i\omega p_k \tau(t_i)} V_{li}(\omega;p_k)X_{li}(\omega) + e^{-i\omega p_k \tau(t_i)} V_{ni}(\omega;p_k)$$
$$X_{ni}(\omega;p_k) + e^{-i\omega p_k \tau_{nik}} N_i(\omega;p_k) \quad (75)$$

where $X_{li}$ is the linearly scattered signal and $X_{ni}$ is the nonlinearly scattered signal that is given with the general nonlinear dependency on $p_k$ that includes nonlinear scattering from micro-bubbles. From fluids and tissue we generally can approximate $Z_{ni}(\omega;p_k) \approx p_k Z_{ni}(\omega)$. The filter $V_{li}(\omega;p_k)$ represents the pulse form distortion as it affects the linear scattering, and the filter $V_{ni}(\omega;p_k)$ represents the pulse form distortion as it affects the nonlinear scattering. We define the filter $H_i(\omega;p_k)$ from the following relation $$H_i(\omega;p_k)N_i(\omega;p_k) = N_i(\omega;0) \quad (76)$$

Neglecting the nonlinear scattering term relative to the linear scattering term in Eq. (75), we can estimate the linear scattering with strong suppression of Class I/II pulse reverberation noise from the received signal from two pulse complexes with $\pm p_1$ amplitude of the LF pulse, as $$S_i(\omega;p_1) = e^{-i\omega p_1 \tau_i} V_{li}(\omega;p_1)X_{li}(\omega) + e^{-i\omega p_1 \tau_{ni}} N_i(\omega;p_1)$$

$$S_i(\omega;-p_1) = e^{i\omega p_1 \tau_i} V_{li}(\omega;-p_1)X_{li}(\omega) + e^{i\omega p_1 \tau_{ni}} N_i(\omega;-p_1) \quad (77)$$

with the solution $$X_{li}(\omega) = \frac{e^{i\omega p_1 \tau_{ni}} H_i(\omega; p_1)S_i(\omega; p_1) -}{e^{i\omega p_1[\tau_{ni}-\tau_i]}H_i(\omega; p_1)V_{li}(\omega; p_1) -} \quad (78)$$
$$\frac{e^{-i\omega p_1 \tau_{ni}} H_i(\omega; -p_1)S_i(\omega; -p_1)}{e^{-i\omega p_1[\tau_{ni}-\tau_i]}H_i(\omega; -p_1)V_{li}(\omega; -p_1)}$$

To estimate both the linear and nonlinear scattering with strong suppression of the pulse reverberation noise, we can combine the signal from three transmitted pulse complexes as $$S_i(\omega;p_1) = e^{-i\omega p_1 \tau_i}\{V_{li}(\omega;p_1)X_{li}(\omega) + p_1 V_{ni}(\omega;p_1)X_{ni}(\omega)$$
$$\} + e^{-i\omega p_1 \tau_{ni}}N_i(\omega;p_1) \ a)$$

$$S_i(\omega;0) = X_{li}(\omega) + N_i(\omega;0) \ b)$$

$$S_i(\omega;-p_1) = e^{i\omega p_1 \tau_i}\{V_{li}(\omega;-p_1)X_{li}(\omega) + p_1 V_{ni}(\omega;-p_1)X_{ni}$$
$$(\omega)\} + e^{i\omega p_1 \tau_{ni}}N_i(\omega;-p_1) \ c) \quad (79)$$

where we have made the approximation $X_{ni}(\omega;p_k) \approx p_k X_{ni}(\omega)$ for the linear scattering. Delay correction and filtering according to Eq. (76) and combination of a) and b), and c) and b) gives us two equations with noise highly suppressed $$a_{11}X_{li}(\omega) + a_{12}X_{ni}(\omega) = b_1$$

$$a_{21}X_{li}(\omega) + a_{22}X_{ni}(\omega) = b_2 \quad (80)$$

where
$a_{11}=e^{i\omega p_1[\tau_{ni}-\tau_i]}H_i(\omega;p_1)V_{li}(\omega;p_1)-1$   $a_{12}=p_1e^{i\omega p_1[\tau_{ni}-\tau_i]}V_{ni}(\omega;p_1)H_i(\omega;p_1)$
$a_{21}=e^{-i\omega p_1[\tau_{ni}-\tau_i]}H_i(\omega;-p_1)V_{li}(\omega;-p_1)-1$   $a_{22}=-p_1e^{-i\omega p_1[\tau_{ni}-\tau_i]}H_i(\omega;-p_1)V_{ni}(\omega;-p_1)$
$b_1=H_i(\omega;p_1)e^{i\omega p_1[\tau_{ni}-\tau_i]}S_i(\omega;p_1)-S_i(\omega;0)$
$b_2=H_i(\omega;-p_1)e^{-i\omega p_1[\tau_{ni}-\tau_i]}S_i(\omega;-p_1)-S_i(\omega;0)$
with the solution for the linear and nonlinear scattering $$\text{a) } X_{li}(\omega) = \frac{a_{22}b_1 - a_{12}b_2}{a_{11}a_{22} - a_{12}a_{21}} \qquad (81)$$
$$\text{b) } X_{ni}(\omega) = \frac{-a_{21}b_1 - a_{11}b_2}{a_{11}a_{22} - a_{12}a_{21}}$$

Even if we can not make the approximation $X_{ni}(\omega;p_k) \approx p_k X_{ni}(\omega)$, Eq. (81b) gives a signal where both the noise and the linear scattering is highly suppressed (eliminated), and hence represents a nonlinear scattering estimate. As the linear scattering is generally much stronger than the nonlinear scattering, Eq. (81a) is an estimate for the linear scattering, or we could use the approximate estimate in Eq. (77) for the linear scattering.

With equal transmit and receive beams and no pulse form distortion, we get $V_{ik}=Q_i=1$ which gives $$A_i(\omega;t_1,t_2;p_k)=2\cos\{\omega p_k[\tau(t_i-t_1+t_2)-\tau(t_1)]/2\} \qquad (82)$$

and $$N_i(\omega; p_k) = \int_0^{t_{2m}} dt_2 \qquad (83)$$
$$\int_{t_2}^{(t_i+t_{2m})/2} dt_1 X_{ri}(\omega; t_1, t_2) 2\cos\{\omega p_k[\tau(t_i - t_1 + t_2) - \tau(t_1)]/2\} \times$$
$$\cos\{\omega p_k[\tau(t_i - t_1 + t_2) + \tau(t_1) - 2\tau_{ni}]/2\} -$$
$$i\int_0^{t_{2m}} dt_2 \int_{t_2}^{(t_i+t_{2m})/2} dt_1 X_{ri}(\omega; t_1, t_2) 2\cos$$
$$\{\omega p_k[\tau(t_i - t_1 + t_2) - \tau(t_1)]/2\} \times \sin$$
$$\{\omega p_k[\tau(t_i - t_1 + t_2) + \tau(t_1) - 2\tau_{ni}]/2\}$$

If we can determine $\tau_{ni}$ so that the last integral is zero, we get $N_i(\omega;-p_k)=N_i(\omega;p_k)$, i.e. $N_i$ is invariant for changes in polarity of the LF pulse. We note that this $\tau_{ni}$ also gives the minimal phase of $N_i$. This implies that $H_i(\omega;p_1)=H_i(\omega;-p_1)$ in Eq. (76), which allows us to neglect the filtering in Eq. (78) to solve Eq. (77). To estimate both linear and nonlinear scattering, we can transmit 4 pulse complexes with LF amplitudes of $\pm p_1$ and $\pm p_2$ that gives the received signals $$S_i(\omega;p_1)=e^{-i\omega p_1\tau_i}\{V_{li}(\omega;p_1)X_{li}(\omega)+p_1V_{ni}(\omega;p_1)X_{ni}(\omega)\}+e^{-i\omega p_1\tau_{ni}}N_i(\omega;p_1)$$

$$S_i(\omega;-p_1)=e^{i\omega p_1\tau_i}\{V_{li}(\omega;-p_1)X_{li}(\omega)+p_1V_{ni}(\omega;-p_1)X_{ni}(\omega)\}+e^{i\omega p_1\tau_{ni}}N_i(\omega;-p_1)$$

$$S_i(\omega;p_2)=e^{-i\omega p_2\tau_i}\{V_{li}(\omega;p_2)X_{li}(\omega)+p_2V_{ni}(\omega;p_2)X_{ni}(\omega)\}+e^{-i\omega p_1\tau_{ni}}N_i(\omega;p_2)$$

$$S_i(\omega;-p_2)=e^{i\omega p_2\tau_i}\{V_{li}(\omega;-p_2)X_{li}(\omega)+p_2V_{ni}(\omega;-p_2)X_{ni}(\omega)\}+e^{i\omega p_1\tau_{ni}}N_i(\omega;-p_2) \qquad (84)$$

Delay correction and combination of the two first and the two last equations give us two equations with highly suppressed pulse reverberation noise that can be solved similar to Eqs. (80, 81) for the linear and nonlinear scattering signals.

With a large, full, and unfocused LF aperture so that the HF imaging region is in an LF near field, it is possible to obtain a close to linear increase of the nonlinear propagation delay, shown as 812, in FIG. 8. In this case we can approximate. In this situation we can arrange the HF pulse to ride on the crest or trough of the LF pulse for most of the imaging distance, which gives low pulse form distortion and we can approximate $\tau(t_i)\approx\tau(t)t_i/t$, and $[\tau(t_i-t_1+t_2)+\tau(t_1)-2\tau_{ni}]/2=\tau(t)(t_i+t_2-2\tau_{ni})/2$. If in addition the transducer array is the strongest $2^{nd}$ reflector so that we get contribution to the integral only for $t_2=0$ (i.e. $X_{ri}(\omega;t_1,t_2)\approx 0$ for $t_2\neq 0$), the last integral in Eq. (83) will be zero for all frequencies for, $\tau_{ni}=t_i/2$. When there are multiple, strong $2^{nd}$ scatterers for $t_2>0$, $\tau_{ni}$ increases above this value. Integration over $t_2$ gives minimum phase of $N_i$ for $\tau_{mik}=(t_i+t_{2ka})/2$ where $t_{2ka}$ is an "average" depth of $2^{nd}$ scatterers. It is then generally difficult to find a $\tau_{ni}$ that makes the last integral zero for all angular frequencies $\omega$ of the signal, but we make great advances in combined suppression of Class I and II pulse reverberation noise by finding a $\tau_{ni}$ that makes the last integral zero at the center angular frequency $\omega_0$ of the noise signal. With limited deviations from the linear variation with fast time of $\tau(t)$, for example shown as 811A/B in FIG. 8, we can still find a $\tau_{ni}$ that makes the last integral vanish at the center angular frequency $\omega_0$. We note that with a nonlinear propagation delay that is concave upwards with the fast time, as 811A/B, $[\tau(t_i-t_1+t_2)+\tau(t_1)]/2$ gives a value that is the nonlinear propagation delay deeper than $(t_i+t_2)/2$, while for a nonlinear propagation delay that is convex upwards $[\tau(t_i-t_1+t_2)+\tau(t_1)]/2$ gives a value that is the nonlinear propagation delay shallower than the $(t_i+t_2)/2$.

As a further modification to this method, we note that the expression in Eq. (70) can be modified as $$Q_i(\omega;t_1)V_{ik}(\omega;t_1;p_k)e^{-i\omega p_k\tau(t_1)}+V_{ik}(\omega;t_i-t_1+t_2;p_k)e^{-i\omega p_k\tau(t_i-t_1+t_2)}=D_{ik}(\omega;t_1,t_2;p_k)e^{-i\omega p_k\tau(t_1)}+V_{ik}(\omega;t_i-t_1+t_2;p_k)[e^{-i\omega p_k\tau(t_1)}+e^{-i\omega p_k\tau(t_i-t_1+t_2)}] \qquad (85)$$

where we have defined $$D_{ik}(\omega;t_1,t_2;p_k)=Q_i(\omega;t_1)V_{ik}(\omega;t_1;p_k)-V_{ik}(\omega;t_i-t_1+t_2;p_k) \qquad (86)$$

The combined pulse reverberation noise of Class I-III in Eqs. (72, 73) can then be written as $$R_{ik}(\omega;p_k)=e^{-i\omega p_k\tau_{1i}}N_{1i}(\omega;p_k)+e^{-i\omega p_k\tau_{2i}}N_{2i}(\omega;p_k) \qquad (87)$$

where we have defined $$N_{1i}(\omega; p_k) = \int_0^{t_{2m}} dt_2 \qquad (88)$$
$$\int_{t_2}^{(t_i+t_{2m})/2} dt_1 X_{ri}(\omega; t_1, t_2) D_{ik}(\omega; t_1, t_2; p_k) e^{-i\omega p_k(\tau(t_1)-\tau_{1i})} =$$
$$\int_0^{t_{2m}} dt_2 \int_{t_2}^{(t_i+t_{2m})/2} dt_1 X_{ri}(\omega; t_1, t_2) D_{ik}(\omega; t_1, t_2; p_k)$$
$$\cos\omega p_k(\tau(t_1)-\tau_{1i}) -$$
$$i\int_0^{t_{2m}} dt_2 \int_{t_2}^{(t_i+t_{2m})/2} dt_1 X_{ri}(\omega; t_1, t_2) D_{ik}(\omega; t_1, t_2; p_k)$$
$$\sin\omega p_k(\tau(t_1)-\tau_{1i})$$

and

-continued $$N_{2i}(\omega; p_k) = \qquad (89)$$

$$\int_0^{t_{2m}} dt_2 \int_{t_2}^{(t_i+t_{2m})/2} dt_1 X_{ri}(\omega; t_1, t_2)$$

$$V_{ik}(\omega; t_i - t_1 + t_2; p_k) \times e^{-i\omega p_k[\tau(t_i-t_1+t_2)+\tau(t_1)-2\tau_{2i}]/2}$$

$$2\cos(\omega p_k[\tau(t_i - t_1 + t_2) - \tau(t_1)]/2) =$$

$$\int_0^{t_{2m}} dt_2 \int_{t_2}^{(t_i+t_{2m})/2} dt_1 X_{ri}(\omega; t_1, t_2) V_{ik}(\omega; t_i - t_1 + t_2; p_k)$$

$$2\cos(\omega p_k[\tau(t_i - t_1 + t_2) - \tau(t_1)]/2) \times$$
$$\cos(\omega p_k[\tau(t_i - t_1 + t_2) + \tau(t_1) - 2\tau_{2i}]/2) -$$

$$i \int_0^{t_{2m}} dt_2 \int_{t_2}^{(t_i+t_{2m})/2} dt_1 X_{ri}(\omega; t_1, t_2) V_{ik}(\omega; t_i - t_1 + t_2; p_k)$$

$$2\cos(\omega p_k[\tau(t_i - t_1 + t_2) - \tau(t_1)]/2) \times$$
$$\sin(\omega p_k[\tau(t_i - t_1 + t_2) + \tau(t_1) - 2\tau_{2i}]/2)$$

We then would choose $\tau_{1i}$ so that the last integral of $N_{1i}(\omega; p_k)$ becomes zero, at least for the center angular frequency $\omega_0$, and we would choose $\tau_{2i}$ so that the last integral of $N_{2i}(\omega; p_k)$ becomes zero, at least for the center angular frequency $\omega_0$. The delays then gives a good frequency-linear approximation to the phase of the noise components. One then have the following filter relations $N_{1i}(\omega; -p_k) = H_{1i}(\omega; p_k) N_{1i}(\omega; p_k)$ and $N_{2i}(\omega; -p_k) = H_{2i}(\omega; p_k) N_{2i}(\omega; p_k)$. These relations can be used for suppression of Class I-III pulse reverberation noise through combinations of delay and filter corrected received HF signal from multiple transmitted pulse complexes. We note that when nonlinear pulse distortion can be neglected, the above selections of $\tau_{1i}$ and $\tau_{2i}$ gives $N_{1i}(\omega; -p_k) = N_{1i}(\omega; p_k)$ and $N_{2i}(\omega; -p_k) = N_{2i}(\omega; p_k)$, which simplifies the processing.

Figure 10:
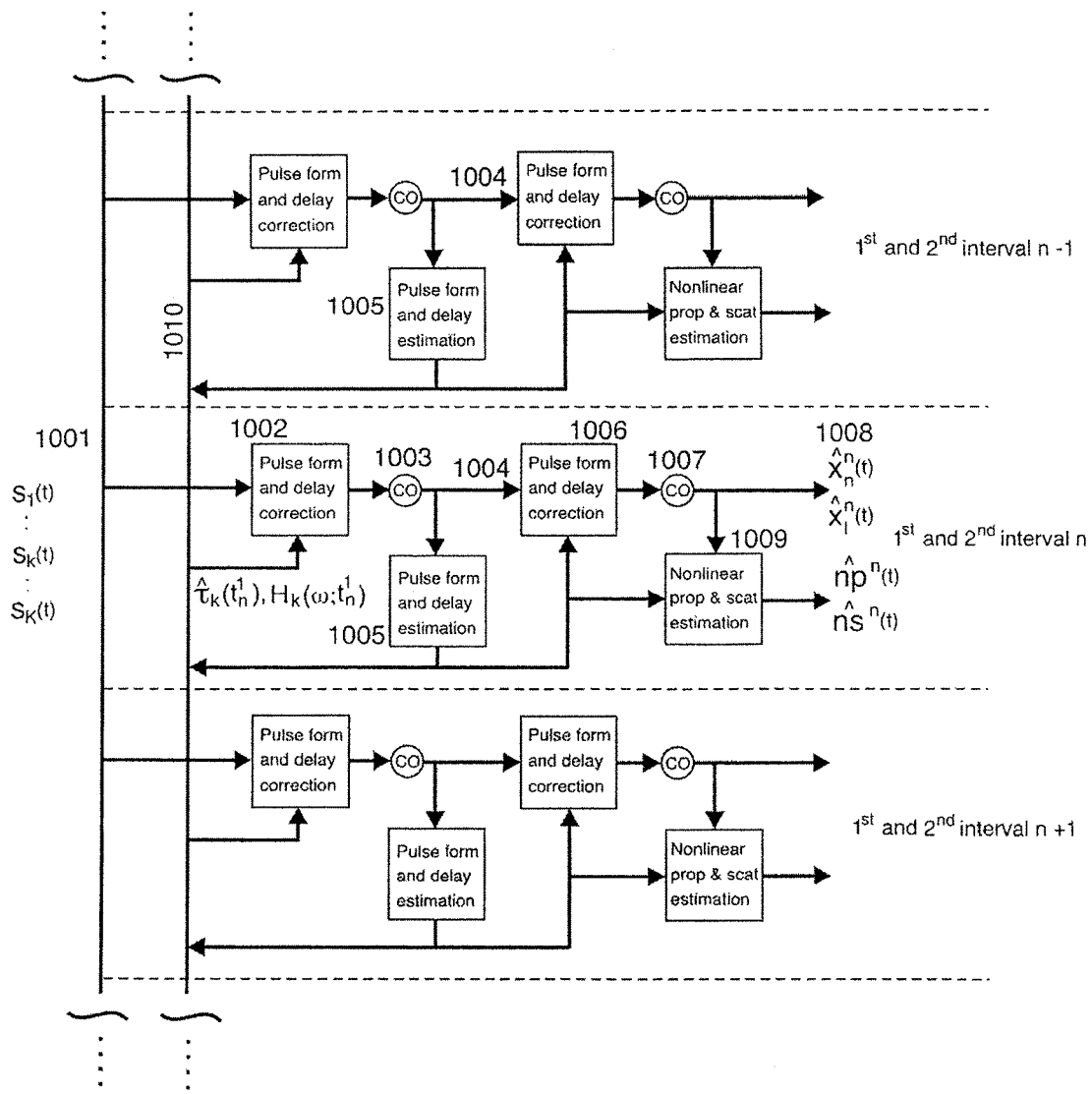
FIG. 10 shows a block diagram of signal processing for suppression of one or both of pulse reverberation noise, and linear scattering components to extract the nonlinearly scattered components.

The above discussion stimulates the introduction of a multi-step suppression of multiple scattering noise as illustrated in the processing block diagram of FIG. 10. In this FIG. 1001 indicates the received HF signals $s_1(t) \ldots s_k(t) \ldots s_K(t)$ from K transmitted pulse complexes with variations in the LF pulse, and with k as the pulse number coordinate (slow time coordinate). The variations in the LF pulse can be in the amplitude and/or phase and/or frequency of the transmitted LF pulse, and one can also have variations in the LF transmit aperture and focus. The whole image depth is divided into a set of image intervals, referred to as $2^{nd}$ intervals, where noise suppression and potential estimation of nonlinearly scattered signals, and nonlinear propagation and scattering parameters are done for each $2^{nd}$ interval separately according to the block diagram of FIG. 10 which we describe in more detail below. The $2^{nd}$ intervals can optionally be placed at a region of special interest of the image depth.

Figure 9:
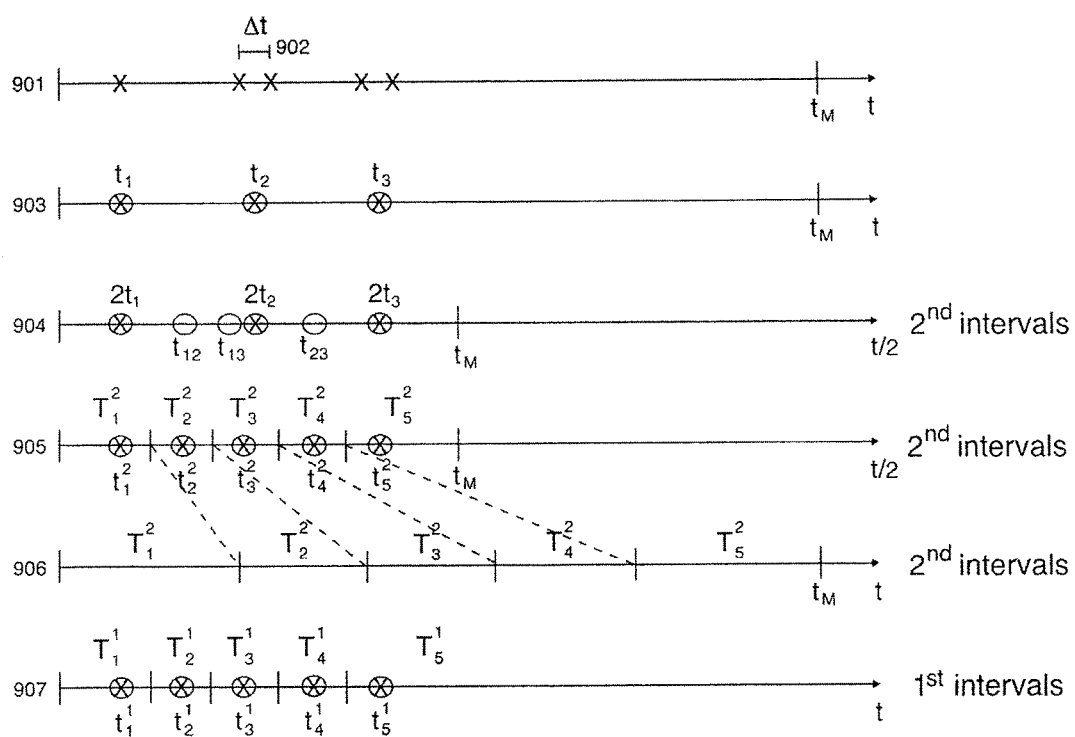
FIG. 9 shows conceptual illustration of combined suppression for Class I and II pulse reverberation noise.

For more detailed illustration of this situation we describe with reference to FIG. 9 an example according to the invention on how said $2^{nd}$ intervals can be selected for the situation of linear fast time variation of the nonlinear propagation delay, with the transducer surface as the dominating $2^{nd}$ scatterer.

We first select locations in the fast time of strong scatterers that produce visible pulse reverberation noise. These are by example indicated by the X on the fast time line 901 in the Figure. These scatterers can be selected manually, for example through direct pointing on the display screen of a 2D image, a M-mode or an A-mode display, etc., or through automatic selection of the strongest back scatter amplitudes compensated for attenuation in the object, or a combination of these. The manual pointing can be done with a cursor technique or touch screen technique according to known methods. The attenuation compensation can for example be done with the depth gain controls found in ultrasound imaging instruments, or based on assumed or estimated attenuation coefficients. The scatterers can be selected for each beam direction, or they can be the same for a group of beam directions or the whole image.

The rate of change of the nonlinear propagation lag and the pulse form distortion with fast time defines a resolution requirement $\Delta t$ along the fast time, indicated as 902 in the Figure. The nonlinear propagation delay and pulse form distortion changes accumulatively, Eq. (3), and hence vary slowly with depth. $\Delta t$ is therefore selected so that one have limited variation of the nonlinear propagation delay and pulse form distortion within $\Delta t$, where the tolerable variation depends on the required suppression of the pulse reverberation noise. Strong scatterers that are closer to each other than $\Delta t$ are then grouped together and merged and represented by an equivalent scatterer of the group, for example at the point of gravity, indicated by ⊗ on the fast time line 903 in the Figure. These equivalent scatterers have the fast time positions $t_i$, $i=1, \ldots, I$, where the example in 903 of FIG. 9 shows 3 equivalent scatterers with positions $t_1, t_2, t_3$ on the fast time line 903.

The equivalent scatterers give rise to Class III pulse reverberation noise at the fast time noise points $2t_i$, shown as ⊗ on the $2^{nd}$ intervals fast time scale 904, shown compressed versus t/2. The equivalent scatterers also generate Class I and II type pulse reverberation noise at the Class I/II time points $t_{ij} = t_i + t_j$, $i, j = 1, 2, \ldots, I$. The locations of these Class I/II time points are in our example shown as ○ on the time line 904.

Noise points of Class I/II and Class III noise on the line 904 that are closer than $2\Delta t$, are merged to groups and replaced by center noise point of the $2^{nd}$ intervals, $t^2_n$, $n=1, \ldots, N$, e.g. the point of gravity of the groups. This gives in our example the center noise points, $t^2_1, t^2_2, t^2_3, t^2_4, t^2_5$, indicated by ⊗ on the compressed fast time line 905. The end points $(t^2_{sn}, t^2_{en})$ of the $2^{nd}$ intervals $T^2_n$ can then for example be defined by the midpoints between center noise points that gives the $2^{nd}$ intervals $T^2_1, T^2_2, T^2_3, T^2_4, T^2_5$ on the compressed fast time line 905 and the uncompressed fast time line 906. The right endpoint of the last interval ($T^2_5$) can typically be set to the maximal image depth $t_M$.

For suppression of pulse reverberation noise in the $2^{nd}$ interval $T^2_n$, the received signals are corrected with the nonlinear propagation delay and pulse form distortion at the $1^{st}$ interval correction time points $t^1_n = t^2_n/2$, and combined in the pulse number coordinate, for example as in Eqs. (56). The fast time line 907 shows as ⊗ the correction time points $t^1_1, t^1_2, t^1_3, t^1_4, t^1_5$ for the five $2^{nd}$ intervals in the example. The midpoints between the correction points can be used to define the $1^{st}$ set of intervals $T^1_n = (t^1_{sn}, t^1_{en})$ defined for the continuous distribution of noise generating scatterers described below.

The processing block diagram in FIG. 10 is divided into a set of parallel processing structures for each $2^{nd}$ interval $T^2_n = (t^2_{sn}, t^2_{en})$. The parallel structure is shown for overview, and in a practical processor, the processing can be done in time series in the same processing structure, starting with the $1^{st}$ set of paired intervals. To obtain the noise suppressed signal for the n-th $2^{nd}$ interval, the received HF signals are in unit 1002 delay corrected with estimates of the nonlinear propagation delay, and potentially also pulse distortion, at a characteristic depth $t_n^1$ in the pair wise matched $1^{st}$ interval $T^1_n = (t^1_{sn}, t^1_{en})$ to form corrected HF signals for the nth $2^{nd}$ interval. Said corrected HF signals are then combined in unit 1003 in the pulse number coordinate, for example through a high-pass filter along the pulse number coordinate (slow time), to form a set of noise suppressed HF signals 1004, $z_1^n(t), \ldots, z_m^n(t), \ldots, z_M^n(t)$, for the pair wise matched $2^{nd}$ interval $T^2_n$ where the pulse reverberation noise (multiple scattering noise) is highly suppressed, similar to Eq. (56).

The noise suppressed signals for each $2^{nd}$ intervals $T^2_n = (t^2_{sn}, t^2_{en})$ are then in unit 1005 used for estimation of corrections for the nonlinear delays $\hat{\tau}(t)$ and pulse distortion correction in said each $2^{nd}$ intervals. One of the received HF signals, and the noise suppressed signals, are then used as intermediate HF signals, and said intermediate HF signals are corrected for nonlinear propagation delay and potentially also pulse form distortion in said each $2^{nd}$ intervals in unit 1006 to form corrected intermediate HF signals that are combined in unit 1007 for strong suppression of the linear scattering in the HF signals to form estimates 1008 of nonlinear scattering HF signals that represent nonlinear scattering from the object in $T^2_n = (t^2_{sn}, t^2_{en})$, $\hat{x}_n(t)$, as exemplified in Eqs. (52, 58, 81). Similarly can one estimate the linear scattering HF signal for the $2^{nd}$ interval $T^2_n$, $\hat{x}_l(t)$, as exemplified in Eqs. (52, 59, 81).

From the estimated nonlinear propagation delay one estimates the nonlinear propagation parameter, Eqs. (9-11), and from the envelopes of the nonlinear and linear scattering HF signals one estimates the nonlinear scattering parameter, Eqs. (15-17), in unit 1009. Signal based estimation of the nonlinear propagation delay $\hat{\tau}(t_1)$ and pulse distortion correction for a particular $1^{st}$ interval can typically be estimated from the noise suppressed signals 1004 in a unit 1005. The estimates from this unit is used directly for correction for nonlinear propagation delay and pulse form distortion for suppression of linear scattering HF signal components in the $2^{nd}$ intervals in unit 1006. The estimates are also communicated on the bus 1010 so that in the correction unit 1002 the corrections for the nonlinear propagation delays and pulse form distortions at the time points $t^1_n$ for the $1^{st}$ intervals can be taken from the estimates of a previous block for $2^{nd}$ intervals that overlaps or are close to $t^1_n$.

In many situations one has a dense distribution of strong scatterers that produces pulse reverberation noise, where it is difficult to select an adequate discrete set of strong scatterers as marked by the X on the fast timeline 901 in FIG. 9. We can then by example divide the region of strong scatterers into a set of $1^{st}$ intervals $T_{1n}$ with endpoints $(t^1_{sn}, t^1_{en})$, of maximal length $\Delta t$, and represent the scatterers in each interval by an equivalent scatterer at $t^1_n$, for example as the ⊗ shown on the timeline 907 in FIG. 9. The intervals and equivalent scatterers can be selected for each beam direction, or they can be the same for a group or beam directions or the whole image. We then define the set of $2^{nd}$ intervals, $T^2_n = (t^2_{sn}, t^2_{en})$ where each $2^{nd}$ interval $T^2_n$ corresponds to the $1^{st}$ interval $T^1_n = (t^1_{sn}, t^1_{en})$, pair wise, so that $t^2_{sn} \approx 2t^1_{sn}$ and $t^2_{en} \approx 2t^1_{en}$. The nonlinear propagation delays and pulse form distortions at the equivalent scatterers in the $1^{st}$ intervals are then used to define corrections for the nonlinear propagation delay and pulse form distortion in the corresponding $2^{nd}$ intervals before the signals are combined to produce noise suppressed HF signals 1004, $z_1^n(t), \ldots, z_m^n(t), \ldots, z_M^n(t)$, for the $2^{nd}$ interval $T^2_n = (t^2_{sn}, t^2_{en})$.

One can also work the opposite way, where one starts by selecting the fast time $t^2_n$ as the center of a $2^{nd}$ interval where one wants to correct for pulse reverberation noise, and then apply the corrections for the nonlinear propagation delays and pulse form distortion at t/2 before the signals are combined to produce noise suppressed HF signals 1004, $z_1^n(t), \ldots, z_m^n(t), \ldots, z_M^n(t)$, for the $2^{nd}$ interval $T^2_n = (t^2_{sn}, t^2_{en})$. This procedure will automatically select the intervals. The advantage with the $1^{st}$ procedure where one starts by selecting the strong scatterers that produces pulse reverberation noise, is that we directly address the regions where the pulse reverberation noise is strong. There will always be some errors in the procedure, particularly in the estimation of the corrections for the nonlinear propagation delay and pulse form distortion, and these errors might introduce visible noise where the pulse reverberation noise is low.

The nonlinear propagation delay and pulse form distortion changes accumulatively, Eq. (3), and hence vary slowly with depth. The length of the $1^{st}$ intervals $T^1_n$ is therefore often selected so that one have limited variation of the HF nonlinear propagation delay and HF pulse distortion within each interval (f.ex. given by $\Delta t$ in 902), where the limit is given by the required suppression of the pulse reverberation noise. The tolerable variation of the nonlinear propagation delay and pulse form distortion also depends on how many strong scatterers/reflectors are found within said $1^{st}$ interval. One can similarly set the boundaries between said $1^{st}$ intervals fixed, or fixedly related to the selected measurement or image depth, with a possibility to adjust the boundaries from the instrument control or automatically by a signal processor, for improved noise suppression.

When the LF transmit aperture has a large inactive region around the center, one can get a variation of $\tau(t)$ indicated as 811A/B in the diagram 810 of FIG. 8. In this case one gets a near range region with very low LF pressure, which gives close to zero nonlinear propagation delay (and pulse form distortion) shown as 811A in the Figure, followed by a close to linear increase 811B of the nonlinear propagation delay. The effect can be amplified by using a transmit timing of the HF pulse relative to the LF pulse, so that the HF pulse propagates in front of the LF pulse on the near field beam axis, and slides into the HF pulse with depth (at $t_0$) per the discussion in relation to FIGS. 3A-3C. An advantage with this zero observed LF pressure in the near range region (811A) is that $s_+(t) - s_-(t)$ or $s_+(t) - s_0(t)$ provides strong suppression of pulse reverberation noise where the $1^{st}$ scatterer is in the near-field. When the $3^{rd}$ scatterer also is in the near-field, this operation gives suppression of Class I, II, and III pulse reverberation noise, which extends to the depth of $t = 2t_0$. With especially strong scatterers in the body wall the higher than $3^{rd}$ order scattering pulse reverberation noise where the $1^{st}$ scatterer is in the body wall can be visible and make this noise extend beyond $t = 2t_0$. The design of the LF radiation aperture is then conveniently done so that the part 811A covers the body wall where one typically has very strong scatterers/reflectors. Suppression of pulse reverberation noise where $1^{st}$ scatterers are in the body wall can then be strongly suppressed without corrections for nonlinear propagation delay and pulse form distortion. However, when the $1^{st}$ scatterer moves into the region of manipulating LF pulse (811B), delay correction and potentially pulse form correction will further suppress this noise.

The strongest scatterers are usually found in the body wall, with weaker scatterers in the object inside the body wall. Designing the beams so that 811A covers the body wall, it can be convenient to define three types of pulse reverberation noise as:

Type A: For this type, $1^{st}$ and the $3^{rd}$ scatterers are in the body wall, and is the strongest component of the pulse reverberation noise. It is suppressed without corrections for nonlinear propagation delay or pulse form correction.

Type B: This type is found when one of the scatterers move into the close to linear part of the delay curve (811B). As the scatterers beyond the body wall is weaker than the scatterers within the body wall, this type of noise is weaker than type A. Class I of this type is suppressed without corrections for nonlinear propagation delay or pulse form correction, as the $1^{st}$ scatterer is within the body wall (811A). To suppress Class II noise of Type B, one must correct for the nonlinear propagation delay and potential pulse form distortion at the location 802 of the outmost scatterer participating in the reverberation chain.

Type C: This type is found when both the $1^{st}$ and the $3^{rd}$ scatterers (810 and 802) are located inside the close to linear part of the delay curve (811B). As both scatterers are of the weak type beyond the body wall, this type of noise is weaker than both Type B and Type A noise.

We note that for $t_a > t_0$, the approximate linear part of the delay curve 811B takes the form $$\tau_k(t_a) \approx \tau_k(t) \frac{t_a - t_0}{t - t_0} t_a > t_0 \qquad (90)$$

When one or both of the scatterers move into the region of manipulating LF pulse (811B) $(t-t_1 > t_0)$ we note that the average propagation delay, as described in Eq. (73), takes the form $$\frac{1}{2} \{\tau(t_i - t_1 + t_2) + \tau(t_1)\} = \qquad (91)$$

$$\begin{cases} \tau_k[(t_i + t_2)/2 + (t_0 - t_1)/2] & \text{for } t_1 < t_0 \text{ and } t_i - (t_1 - t_2) > t_0 \quad a) \\ \tau_k((t_i + t_2)/2) & \text{for } t_0 < t_1 < t/2 \text{ and } t > 2t_0 \quad b) \end{cases}$$

where for a) one of the scatterers are inside 811A and the other scatterer is within 811B, while for b) both the $1^{st}$ and $3^{rd}$ scatterers are within 811B. We note that in this last case, we get suppression of Class I-III pulse reverberation noise by delay correcting the received HF signal with $\tau_{nik} = \tau_k((t_i + t_{2a})/2)$ where $t_{2a}$ is an average depth of $2^{nd}$ scatterers. This allows us to model the received signal from pulse complex no. k for $t > t_0$ as $$s_k(t) = V_{k1}\{x_1(t)\} + V_{k2}\{x_2(t)\} + x_3(t) + V_{k4}\{x_4(t)\} + V_{k5}\{x_5(t)\} \qquad (92)$$

where $x_1(t)$ is the $1^{st}$ order linearly scattered signal, $x_2(t)$ is the $1^{st}$ order nonlinearly scattered signal, $x_3(t)$ is Class I/II/III pulse reverberation noise of Type A plus Class I pulse reverberation noise of Type B, $x_4(t)$ is Class II pulse reverberation noise of Type B, while $x_5(t)$ is the Type C noise of Class I/II/III.

For K=5 transmit pulse complexes with variations in the LF pulse, the set of equations of the form Eq. (92) is conveniently solved with elimination, for example along the lines of the operator Gauss elimination method of Eqs. (49-52). Here $x_3(t)$ can be eliminated with simple subtraction of the equations without any inverse correction. For $x_4(t)$ the last scatterer is within 811A, and one could approximate the correction for the nonlinear propagation delay and pulse form distortion to be based on the values at $t-t_a$, where $t_a$ is an average of $d = t_1 - t_2$ (See FIG. 7) within 811A. A $1^{st}$ approximation could be $t_a = t_0/2$, with further manual or automatic adjustments for maximal suppression of the pulse reverberation noise. For $x_5(t)$ one can per Eq. (91b) correct for the nonlinear propagation delay and potential pulse form distortion at $(t_i + t_{2a})/2$ which for the transducer as the dominating $2^{nd}$ scatterer would be $t/2$. One can in many situations neglect $x_5(t)$ as this is of Type C and weakest. In many situations the nonlinear scattering is so weak that $x_2(t)$ can be neglected, and we are then left with only three unknowns, $x_1(t)$, $x_3(t)$, and $x_4(t)$, which are conveniently solved from the three measurements $s_+(t)$, $s_0(t)$, and $s_-(t)$ with transmitted LF pulses of close to $+P_0$, 0, and close to $-P_0$ where inaccuracies in the transmitted LF pulse amplitudes are accounted for in amplitude corrections of the received signals. If further $x_4(t)$ can be neglected, we are left with only two unknowns $x_1(t)$, $x_3(t)$ which are solved from the received signal from two transmitted pulse complexes, or one could include the nonlinear scattering giving three unknowns $x_1(t)$, $x_2(t)$, and $x_3(t)$ which can be solved from the three measurements $s_+(t)$, $s_0(t)$, and $s_-(t)$.

Another situation for approximation is when $t_0$ is adequately short in relation to the image depth. We can then often for deeper image ranges approximate the nonlinear propagation delay and pulse form distortion for pulse reverberation noise of Class I-III to originate at $t_c(t) \approx t/2 + \text{offset}$, and the methods described in FIG. 9 in relation to the fully linear delay curve 812 can then be applied with the corrections for the nonlinear pulse delay and pulse form correction at $t_c(t)$ to suppress the Class I-III pulse reverberation noise.

Hence, the discussion above has given several example embodiments according to the invention, to suppress pulse reverberation noise and extract linear and nonlinear scattering signals. Said nonlinear and linear scattering HF signals are then used for further processing to form final measurement or image signals, for example according to known methods such as envelope detected signals, Doppler signals, fast time spectral content signals, etc.

The noise suppressed HF signals and the nonlinear scattering signals are useful both for backscatter imaging and for computer tomographic (CT) image reconstructions from forward transmitted and angularly scattered signals. The nonlinear propagation lag, Eq. (3), and the integrated pulse distortion is observable directly for the transmitted wave through the object, and are also candidates for CT image reconstruction of local object elasticity parameters.

The suppression of pulse reverberation noise in the signals greatly improves the estimation of corrections for wave front aberrations in the element signals from 1.75D and 2D arrays, for example according to the methods described in U.S. Pat. No. 6,485,423, U.S. Pat. No. 6,905,465, U.S. Pat. No. 7,273,455, U.S. Pat. No. 8,036,616 and U.S. patent application Ser. No. 11/189,350 (US Pat Pub 2005/0277835). When estimation of the corrections for the wave front aberrations are based on signal correlations with the summed HF beam-former output signal with highly suppressed reverberation noise, the reverberation noise in the element signals is uncorrelated to the beam-former output signal. When slow updates of the aberration correction estimates are acceptable, one can use so long correlation time that the effect of the reverberation noise in the element signals or sub-aperture signals on the correction estimates can be negligible. However, when the correlation time is low, it is preferable to suppress the reverberation noise in the individual element or sub-aperture signals according to the methods described above, before the estimation of the aberration corrections, to reduce errors in the aberration correction estimates produced by the reverberation noise.

Similar expressions as discussed for the bulk pressure waves above, can be developed for shear waves in solids, and while we do many of the derivations with reference to bulk pressure waves, it is clear to anyone skilled in the art that similar derivations can be done for shear waves and the invention is hence also applicable to shear waves.

A block diagram of an imaging instrument that uses the described methods for back scatter imaging in its broadest sense according to the invention, is shown in FIG. 11, where 1101 shows the acoustic transducer array that in this example has a high frequency (HF) and low frequency (LF) section. In this broadest implementation of the methods, the array has a two-dimensional distribution of elements, which allows full electronic 3D steering of the high and the low frequency beams, referred to as 2D array, and the instrument is also capable of both estimating and correcting for wave front aberrations. It is clear however that the methods can be used with less complex arrays, as discussed below.

The high frequency part of the array can in full 3D imaging applications have a large number of elements, for example 3,000-30,000, and the number of receive and transmit channels are then typically reduced in a sub-aperture unit 1102, where in receive mode the signals from several neighboring array elements are delayed and summed to sub-aperture signals 1103 for further processing. For aberration corrections, the widths on the array surface of the sub-aperture groups are less than the correlation length of the wave front aberrations, where a typical number of sub-aperture groups and signals could be 100-1000.

For transmission of the pulse complexes, the HF transmit beam former 1104 feeds pulses to the sub-aperture unit 1102, that delays and distributes the signals to all or sub-groups of HF-array elements, while the LF transmit beam former 1105 simultaneously feeds pulses to the LF array elements. The pulse complex transmission is triggered by the instrument controller 1106, which communicates with the sub-units over the instrument bus 1107. As current high-efficient transducers have limited bandwidth, one would typically have different array elements for the HF and LF pulses, but with wider bandwidth transducers one might use the same array elements for the HF and LF pulses, where the HF beam former transmits the complete LF/HF pulse complex.

The receive sub-aperture signals 1103 are fed to the unit 1108, where the sub-aperture signals are delayed for steering of receive beam direction and focusing under the assumption of a homogeneous medium with the constant, average propagation velocity, referred to as homogeneous delays. 3D beam steering and focusing can also be done with sparse arrays, where the sub-aperture unit 1102 could typically be missing, known to anyone skilled in the art. With 1.75D arrays, the number of HF array elements can also be reduced so much that the sub-aperture units could be left out. In the following we therefore use element and sub-aperture signals synonymously.

The element signals that are corrected with the homogenous delays, 1109, are fed to a unit 1110 where corrections for the wave front aberrations are applied, for example estimated according to the methods described in U.S. Pat. No. 6,485,423, U.S. Pat. No. 6,905,465, U.S. Pat. No. 7,273,455, U.S. Pat. No. 8,036,616 and U.S. patent application Ser. No. 11/189,350 (US Pat Pub 2005/0277835), before the element signals are summed to the final receive beam signal. Aberration corrections in the HF transmit beam are done directly in the HF transmit beam former 1104, where the corrections for the individual elements or sub-apertures are fed from aberration correction estimation unit 1113.

The LF and HF arrays are typically organized so that the LF transmit aperture can be selected to be larger than the HF transmit aperture, for the reasons discussed above. One often wants to use an unfocused, or slightly focused LF aperture so that the whole imaging range is within the near field of the LF aperture, to minimize relative position sliding between the HF and LF pulses with depth to obtain a close to constant LF pressure at the propagating HF pulse for imaging of nonlinear scattering and to reduce pulse distortion correction. One also wants to select an inactive region around the center of the LF transmit aperture, to reduce nonlinear manipulation of the object elasticity by the LF pulse in the near field. This can be combined with selection of special timing between the transmitted LF and HF pulses as discussed in relation to FIGS. 3A-3C above. Other interesting selections of LF and HF apertures are for example given in relation to the discussion around Eqs. (29-34). In receive mode one can want to be able to select a HF receive aperture that is wider than the LF transmit aperture for best resolution at deep ranges with dynamic HF receive aperture and focusing. The LF transmit beam former and HF transmit and receive beam formers are therefore generally set up to be able to vary the active area and focus of the LF transmit and HF transmit and receive apertures.

For 3D imaging one would often use multiple receive beams with small angular offsets that cover a wide transmit beam in parallel (simultaneously). The aberration corrections for the angularly offset beams could be a side shifted version of the corrections for the central beam, that are added together with the homogeneous delays for the angular offset in the unit 1110. The output 1111 of the unit 1110 is hence one or more RF-signals for one or more receive beam directions in parallel, that is fed to the processing unit 1112 according to this invention, that performs one or more of the operations according to the methods described above, for example specially pronounced in Eqs. (21-26, 34-36, 43-77, 6-17).

The aberration corrections are estimated in the unit 1113, for example according to the methods described in relation to the cited patents and patent applications. The unit 1113 takes as its input the homogeneously delay corrected signals 1109 and possibly also final beam signals 1114 with suppression of the pulse reverberation noise according to this invention. The delay corrected element signals 1109 are typically first processed with methods according to this invention, typically the methods described in relation to FIGS. 6-10 and Eqs. (21-26, 43-77) to suppress the pulse reverberation noise before estimation of the aberration corrections. One should note that use of signal from moving scatterers as for example found with blood or myocardium and as prescribed in U.S. Pat. No. 6,485,423, would improve the function of methods of suppression of pulse reverberation noise. The estimates based on the nonlinear propagation delays for the individual element/sub-aperture signals as described in U.S. patent application Ser. No. 11/189,350 (US Pat Pub 2005/0277835) and U.S. Pat. No. 8,036,616, also represent interesting estimates themselves, and also as a starting point for further estimations according to the cited patents, both to focus the $1^{st}$ transmit beam and as starting points of an iteration scheme.

When estimation of the corrections for the wave front aberrations are based on signal correlations with the beam-former output signal 1114 with highly suppressed reverberation noise, the reverberation noise in the element signals is uncorrelated to the beam-former output signal. When slow updates of the aberration correction estimates are acceptable, one can use so long correlation time that the effect of the reverberation noise in the element or sub-aperture signals on the correction estimates can be negligible. However, when the correlation time is low, it is preferable to also suppress the reverberation noise in the element or sub-aperture signals before the estimation of the aberration corrections, to reduce errors in the aberration correction estimates produced by the reverberation noise.

The outputs of the unit 1112 are the linearly and nonlinearly scattered signals with suppression of pulse reverberation noise, the two quantitative nonlinear parameters, and Doppler phase and frequency data. These data can be fed directly to the image construction and scan converter unit 1116 that presents images of compressed and colorized versions of the amplitudes of the linearly and nonlinearly scattered signals, the quantitative nonlinear parameters/signals, and object radial displacements, displacement velocities, displacement strains and strain rates. However, to measure the radial velocities of blood or gas bubbles or other objects or fluids, one must further process the linearly or nonlinearly scattered signals in the slow time domain to suppress clutter echo from the object to retrieve the fluid signals for Doppler processing according to known methods, which is done in unit 1115. The outputs of this unit are fed to the image construction unit 1116 to be selected and overlaid the images of the other information. The unite 1116 feeds its output to a display 1117.

Many of the units of the instrument can be implemented as software programs in a general programmable computer, particularly the units 1110, 1112, 1113, 1115, 1116, and 1117, where with added support processors that communicates with the CPU on the CPU bus, like signal or graphics processors, unit 1108 can also be implemented as software in the same computer.

It should be clear to any one skilled in the art, that many simplifications of the instrument as presented in FIG. 11 can be done while still utilizing essential aspects of the invention in the instrument. For example one can have a coarse division of elements in the elevation direction, which would limit electronic direction steering of the beam in the elevation direction, while one still can obtain corrections for the wave front aberrations and dynamic focusing with depth in the elevation direction. This is often referred to as 1.75D arrays and has much less total number of array elements than 2D arrays for full 3D steering of the beam, whereby the sub-aperture unit could be removed. Sparse arrays are another way to reduce the number of elements so that it becomes practical to remove the sub-aperture unit 1102. However, the gain in using the sub-aperture unit is found as long as the dimension of the sub-aperture group along the array surface is less than the correlation length of the wave front aberrations.

One could also remove the estimations and the corrections for the wave front aberrations, i.e. units 1110 and 1113, and still be able to do the processing in unit 1112 to produce both linearly and nonlinearly scattered signals etc. as described above. The array could then be further simplified where elements symmetrically around the beam scan axis (the azimuth axis) are galvanically connected to further reduce the number of independent channels, often referred to as 1.5D arrays. One could similarly use one dimensional (1D) arrays and also annular arrays with mechanical scanning of the beam direction, where the main modification to the block diagram in FIG. 11 is that the sub-aperture unit 1102, the aberration correction unit 1110 and aberration correction estimation unit 1113 are removed. Hence, the invention defines instruments with different complexity, or selectable complexity, and also instruments that can select between the different methods of processing described above, for best performance according to the measurement situation. The complexity of operation can be selected automatically by the instrument controller according to the application selected, or manually by the instrument operator to optimize image quality.

For tomographic image reconstruction, the processing according to this invention would typically be done on the individual receive element signals, before the signals are processed according to the reconstruction algorithms of various kinds found in prior art. A block schematic of a typical instrument for tomographic image reconstruction according to the invention is shown in FIG. 12. The Figure shows measurements with a ring array 1201, where it is clear for anyone skilled in the art that other array configurations, also transducer arrays that would wholly or partly use mechanical scanning to collect the data, could be used without departing from the invention. The array surrounds the object 1202. A unit 1203 selects a group of transmit elements, freely out of all the elements, and generates a transmit pulse complex composed of a low and a high frequency pulse overlapping in time and for example as visualized in FIGS. 1A-1C. Transmissions of the pulse complexes are triggered by the controller unit 1207 via the controller bus 1208. The unit 1204 selects receive elements, sequentially or in parallel or a combination of parallel-sequential manner, from the whole group of elements, and amplifies and digitizes the element signals for further processing according to the invention in the unit 1205. This unit operates according to the principles according to the invention. The processing in unit 1205 provides one or more of the linearly scattered and transmitted signals with substantial suppression of the pulse reverberation noise (multiple scattering), nonlinearly scattered signals, and quantitative nonlinear propagation and scattering parameters that are forwarded to the unit 1206 that provides computerized tomographic images of 2D slices of the object. By mechanically moving the array relative to the object in the direction normal to the Figure, one obtains a 3D reconstructed image of the object.

Figure 13:
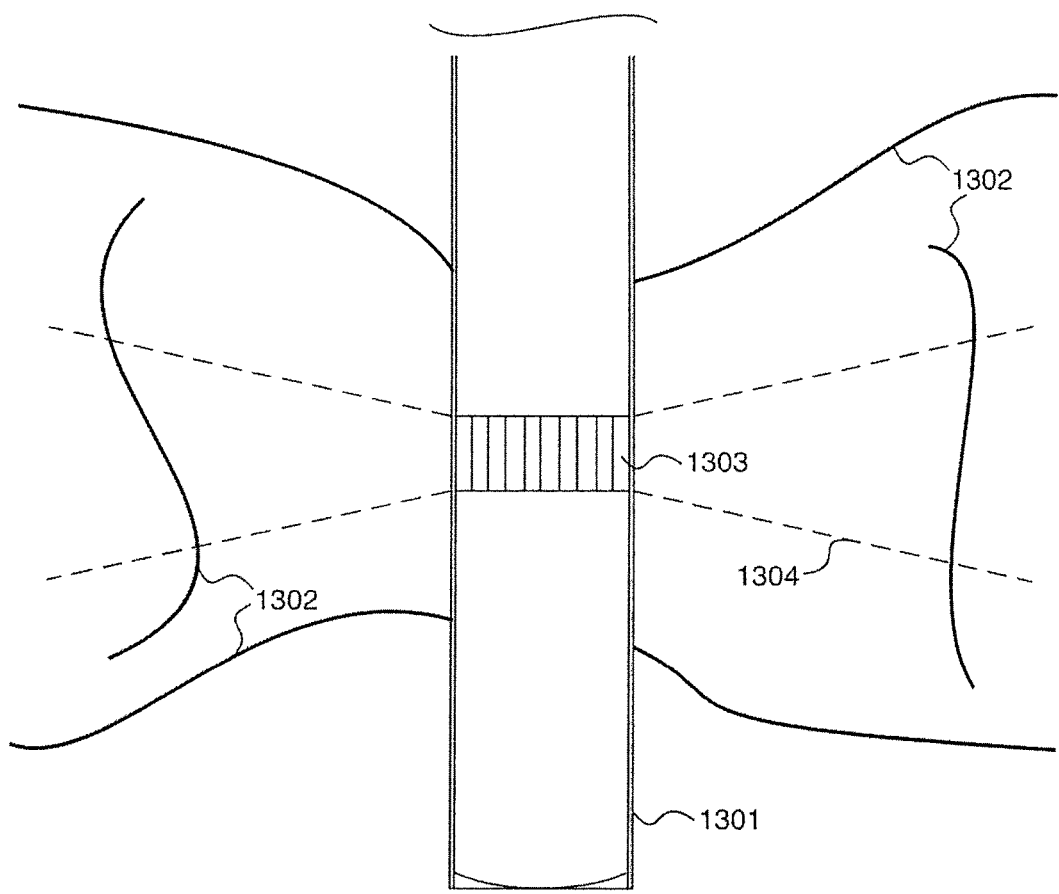
FIG. 13 shows a conceptual illustration for imaging of geologic structures around an oil well according to the invention.

An example instrumentation for use of the methods for acoustic imaging of geologic structures around an oil well, is shown in FIG. 13, 1301 indicates the perforated oil-well production liner with surrounding geologic structures 1302 that typically is composed of porous rock filled with oil, gas, water or mixtures of these, where also solid rock regions can be found. 1303 illustrates an acoustic array for transmission and reception of acoustic pulse complexes according to the invention in selectable sector beams 1304 around the production liner. The received acoustic signals are processed according to the methods described above with the exemplified instrumentation shown in FIG. 11. During drilling, one can also use a single element transducer, or annular array transducer, or a linear array transducer mounted vertically to provide a vertical 2D image of the rock around the well, that is mounted to the rotating drill string above the drill bit, for continuous 360 deg acoustic observation of the rock around the drill with the methods of back scatter imaging according to the invention. With the vertical linear array (switched or phase array) one obtains a 3D mapping of the rock properties around the well. Similar 3D mapping is obtained with single element or annular array transducers as the drill moves through the rock. With oil wells sufficiently close to each other one can also use transmission measurements between oil wells and reconstruct images from transmission and angular measurements as described in relation to FIG. 12.

Thus, while there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention.

It is also expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

7. REFERENCES

[1] U.S. patent application Ser. No. 11/189,350 (US Pat Pub 2005/0277835
[2] U.S. Pat. No. 8,038,616 B2
[3] U.S. Pat. No. 7,727,156 B2
[4] E. Sassaroli and K. Hynynen. Resonance frequency of microbubbles in small blood vessels: a numerical study. Phys. Med. Biol., 2005, 50, 5293-5305.

We claim:

1. A method for measurement or imaging of at least one nonlinear scatterer of elastic waves with a memory of at least one scattering parameter in a region of a scattering object, the method comprising:
    a) transmitting at least two elastic wave pulse complexes towards the region, wherein the at least two elastic wave pulse complexes comprises:
        a first pulse complex that comprises
            a first low frequency (LF) pulse with frequencies in a low frequency band having characteristics to change the at least one scattering parameter of the at least one nonlinear scatterer with a memory that lasts for at least a first time interval after the first LF has passed the at least one nonlinear scatterer, and
            a first high frequency (HF) pulse with a frequency in a high frequency band so that at least in a measurement or imaging depth range, the first HF pulse propagates spatially behind the first LF pulse, but sufficiently close to the first LF pulse that the first HF pulse hits the at least one nonlinear scatterer within the first time interval so as to observe the change of the at least one scattering parameter of the at least one nonlinear scatterer caused by the first LF pulse; and
        a second pulse complex selected from a group consisting of options 1 and 2,
            wherein option 1 is a pulse complex that comprises
                a second HF pulse with a frequency in high frequency band to observe the at least one scattering parameter of the at least one nonlinear scatterer, but does not comprise an LF pulse,
            wherein option 2 is a pulse complex that comprises:
                a second LF pulse, differing/varying from the first LF pulse, with frequencies in a low frequency band having characteristics to change the at least one scattering parameter of the at least one nonlinear scatterer with a memory that lasts for at least a second time interval after the second LF pulse has passed the at least one nonlinear scatterer, and
                a second high frequency (HF) pulse with a frequency in a high frequency band so that at least in a measurement or imaging depth range, the second HF pulse propagates spatially behind the second LF pulse, but sufficiently close to the second LF pulse that the second HF pulse hits the at least one nonlinear scatterer within the second time interval so as to observe the change of the at least one scattering parameter of the at least one nonlinear scatterer caused by the second LF pulse;
    b) receiving HF signals comprising at least one of scattered and transmitted HF components from the first and second pulse complexes;
    c) combining the received HF signals from the first and second pulse complexes to form nonlinear measurement HF signals representing the at least one nonlinear scatterer with a memory of the at least one scattering parameter, with suppression of received HF signals from scatterers other than the at least one nonlinear scatterer.

2. The method of claim 1, wherein the depth range is divided into depth intervals and the scattering object is moving, the method further comprising:
    between steps b) and c), correcting at least one of the received HF signals in at least one depth interval by at least one of:
        i) time delay correction with a correction delay determined by movement of the scattering object; and
        ii) speckle correction with a speckle correction filter determined by movement of the scattering object,
    to form, together with potentially uncorrected received HF signals, a group of at least two intermediate HF signals from the at least two transmitted pulse complexes in the at least one depth interval; and
    wherein said step c) comprises combining the at least two intermediate HF signals to suppress linear scattering components from the moving object to form nonlinear measurement HF signals representing the at least one nonlinear scatterer in the at least one depth interval with a memory of the at least one scattering parameter.

3. The method of claim 2, further comprising estimating at least one of said correction delay and the speckle correction filter from a combination of the received HF signals from the at least two pulse complexes.

4. The method of claim 3, wherein option 2 is selected and the selected first and second LF pulses have at least one common characteristic.

5. The method of claim 4, wherein the at least one common characteristic is chosen from the group consisting of center frequency, amplitude, polarity, and pulse length.

6. The method of claim 4, wherein the at least two pulse complexes of option 1 include a pulse complex having a nonzero LF pulse and a pulse complex having a zero LF pulse.

7. The method of claim 6, wherein, for option 2, the at least two pulse complexes comprise at least three pulse complexes, wherein at least two of the at least three pulse complexes have equal LF pulses and a remaining pulse complex of the three has an LF pulse different from the equal LF pulses.

8. The method of claim 2, wherein the at least one nonlinear scatterer has a resonance frequency and the first and second LF pulses have a center frequency that is close enough to a scatterer resonance frequency, so that a variation in the at least one scattering parameter with a memory is produced by resonating oscillations of the at least one nonlinear scatterer excited by at least one of the first and second LF pulses.

9. The method of claim 2, wherein the at least one nonlinear scatterer is at least one of micro-bubbles and micro-calcifications.

10. The method of claim 2, further comprising imaging of at least one resonant nonlinear scatterer with at least one unknown resonance frequency by:
transmitting multiple groups of the at least two pulse complexes
wherein
center frequencies of the first and second LF pulses are equal within each respective group and vary between at least some of the multiple groups; and
if the center frequency of the first and second LF pulses for at least one of the groups is close enough resonance frequency of the at least one resonant nonlinear scatterer, so that a variation in the at least one scattering parameter with a memory are produced by resonating oscillations of the at least one nonlinear scatterer excited by the first and second LF pulse for the at least one of the groups,
then detecting presence of the at least one resonant nonlinear scatterer from received HF signals from the at least two pulse complexes for said at least one of the groups having first and second LF pulse center frequency that is close enough to the resonance frequency.

11. The method of claim 2, further comprising processing the nonlinear measurement HF signals to form an image display of the at least one nonlinear scatterer with a memory of at least one scattering parameter, with suppression of image components from the other scatterers.

12. The method of claim 1, further comprising processing the nonlinear measurement HF signals to form an image display of the at least one nonlinear scatterer with a memory of the at least one scattering parameter, with suppression of image components from the other scatterers.

13. An instrument for measurement or imaging of at least one nonlinear scatterer of elastic waves with a memory of at least one scattering parameter in a region of a scattering object, the instrument comprising:
a) a transmitter configured to transmit elastic wave pulse complexes;
b) a receiver configured to receive at least one of scattered and transmitted components from the transmitted pulse complexes; and
c) at least one controller configured to:
control the transmitter to transmit at least two elastic wave pulse complexes towards the region, wherein the at least two elastic wave pulse complexes comprises:
a first pulse complex that comprises
a first low frequency (LF) pulse with frequencies in a low frequency band having characteristics to change the at least one scattering parameter of the at least one nonlinear scatterer with a memory that lasts for at least a first time interval after the first LF pulse has passed the at least one nonlinear scatterer, and
a first high frequency (HF) pulse with a frequency in a high frequency band so that at least in a measurement or imaging depth range, the first HF pulse propagates spatially behind the first LF pulse, but sufficiently close to the first LF pulse that the first HF pulse hits the at least one nonlinear scatterer within the first time interval so as to observe the change of the at least one scattering parameter of the at least one nonlinear scatterer caused by the first LF pulse; and
a second pulse complex selected from a group consisting of options 1 and 2,
wherein option 1 is a pulse complex that comprises a second HF pulse with a frequency in high frequency band to observe the at least one scattering parameter of the at least one nonlinear scatterer, but does not comprise an LF pulse,
wherein option 2 is a pulse complex that comprises:
a second LF pulse, differing/varying from the first LF pulse, with frequencies in a low frequency band having characteristics to change the at least one scattering parameter of the at least one nonlinear scatterer with a memory that lasts for at least a second time interval after the second LF pulse has passed the at least one nonlinear scatterer, and
a second HF pulse with a frequency in a high frequency band so that at least in a measurement or imaging depth range, the second HF pulse propagates spatially behind the second LF pulse, but sufficiently close to the second LF pulse that the second HF pulse hits the at least one nonlinear scatterer within the second time interval so as to observe the change of the at least one scattering parameter of the at least one nonlinear scatterer caused by the second LF pulse;
control the receiver to receive HF signals comprising at least one of scattered and transmitted HF components from the first and second pulse complexes, and
combine the received HF signals from the first and second pulse complexes to form nonlinear measurement HF signals representing the at least one nonlinear scatterer with a memory of the at least one scattering parameter, with suppression of received HF signals from scatterers other than the at least one nonlinear scatterer.

14. The instrument of claim 13, wherein the depth range is divided into depth intervals, the scattering object is moving, and the at least one controller is further configured to:
correct at least one of the received HF signals in at least one depth interval by at least one of:
i) time delay correction with a correction delay determined by movement of the moving object, and
ii) speckle correction with a speckle correction filter determined by movement of the moving object,
to form, together with potentially uncorrected received HF signals, a group of at least two intermediate HF signals from the at least two transmitted pulse complexes; and
combine the at least two intermediate HF signals to suppress linear scattering components from the moving object to form nonlinear measurement or imaging HF signals representing the at least one nonlinear scatterer with a memory of the at least one scattering parameter.

15. The instrument of claim 14, wherein the at least one controller is further configured to estimate at least one of the correction delay and the speckle correction filter through a combination of the received HF signals from the at least two pulse complexes.

16. The instrument of claim 15, wherein the at least one controller is configured to select, in option 2, first and second LF pulses having at least one common characteristic in the at least two pulse complexes.

17. The instrument of claim 16, wherein the at least one common characteristic is chosen from the group consisting of center frequency, amplitude, polarity, and pulse length.

18. The instrument of claim 15, wherein the at least one controller is configured, for option 1, to select a nonzero LF pulse for at least one of the at least two pulse complexes and a zero LF pulse for at least one of the at least two pulse complexes.

19. The instrument of claim 16, wherein:
the at least one controller is configured to define at least three pulse complexes;
at least two of the at least three pulse complexes have equal LF pulses; and
a remaining pulse complex of the three has an LF pulse different from the equal LF pulses.

20. The instrument of claim 14, wherein the at least one nonlinear scatterer has a resonance frequency and the first and second LF pulses have a center frequency that is close enough to a scatterer resonance frequency, so that a variation in the at least one scattering parameter with a memory is produced by resonating oscillations of the at least one nonlinear scatterer excited by the first and second LF pulses.

21. The instrument of claim 14 wherein, for imaging of at least one resonant nonlinear scatterer with an unknown resonance frequency, the at least one controller is configured to transmit multiple groups of the at least two pulse complexes, wherein:
center frequencies of the first and second LF pulses is the same within each said group and varies between at least some of the multiple groups; and
the center frequency of the first and second LF pulses for at least one of the groups is close enough to resonance frequency that variations in the at least one scattering parameter with a memory are produced by resonating oscillations of the at least one nonlinear scatterer excited by the first and second LF pulses for the at least one of the groups.

22. The instrument of claim 14, further comprising:
a display unit to display an image;
wherein the at least one controller is further configured to process the nonlinear measurement HF signals to form image signals of the at least one nonlinear scatterer with a memory of the at least one scattering parameter, with suppression of image components from the other scatterers.

23. The instrument of claim 13, further comprising:
a display unit to display an image;
wherein the at least one controller is further configured to process nonlinear measurement HF signals to form image signals of the at least one nonlinear scatterer with a memory of the at least one scattering parameter, with suppression of image components from the other scatterers.

24. The instrument of claim 13, further comprising:
an HF receiver beam former configured to record the received HF signals from multiple HF receive beams, parallel in time; and
the at least one controller has sufficient processing capacity to process the received HF signals from the multiple HF receive beams, so that an image frame rate for 2D and 3D imaging is substantially increased as compared to a rate at which collected HF signals from single HF receive beam directions are received serially in time.

25. The instrument of claim 13, wherein the at least one controller is further configured to select a processing method under constraints that are preset or set by an operator.

26. The instrument of claim 13, wherein the at least one controller is further configured to: estimate wave front aberration corrections; and correct wave front aberrations.

* * * * *